(12) United States Patent
Lehoux et al.

(10) Patent No.: US 9,816,035 B2
(45) Date of Patent: Nov. 14, 2017

(54) CONVERSION OF BIOMASS, ORGANIC WASTE AND CARBON DIOXIDE INTO SYNTHETIC HYDROCARBONS

(71) Applicant: GREENFIELD SPECIALTY ALCOHOLS INC., Toronto (CA)

(72) Inventors: Richard Romeo Lehoux, Windsor (CA); Hisham Mohamed Hafez, London (CA); Ranjit Sehdev, Markham (CA); Dave Salt, Mississauga (CA)

(73) Assignee: GreenField Specialty Alcohols Inc., Toronto (CA)

( * ) Notice: Subject to any disclaimer, the term of this patent is extended or adjusted under 35 U.S.C. 154(b) by 134 days.

(21) Appl. No.: 14/978,893

(22) Filed: Dec. 22, 2015

(65) Prior Publication Data
US 2016/0186072 A1 Jun. 30, 2016

Related U.S. Application Data
(60) Provisional application No. 62/096,146, filed on Dec. 23, 2014.

(51) Int. Cl.
*C10G 2/00* (2006.01)
*C12M 1/107* (2006.01)
(Continued)

(52) U.S. Cl.
CPC ............... *C10G 2/34* (2013.01); *C10G 2/32* (2013.01); *C12M 21/04* (2013.01); *C12M 21/12* (2013.01);
(Continued)

(58) Field of Classification Search
CPC ............ C10G 2/34; C10G 2/32; C12M 23/58; C12M 21/04; C12M 21/12; C12M 43/00; C12P 3/00; C12P 5/023
See application file for complete search history.

(56) References Cited

U.S. PATENT DOCUMENTS

| 7,012,103 B2 | 3/2006 | Espinoza et al. |
| 7,794,690 B2 | 9/2010 | Abatzoglou et al. |

(Continued)

FOREIGN PATENT DOCUMENTS

| DE | 4444745 C1 | 8/1996 |
| DE | 102004054468 A1 | 5/2006 |

(Continued)

OTHER PUBLICATIONS

Sie, S. T. et al., "Fundamentals and selection of advanced Fischer-Tropsch reactors", Applied Catalysis A: General, vol. 186, Issues 1-2, Oct. 4, 1999, pp. 55-70.

(Continued)

*Primary Examiner* — Gautam Prakash
(74) *Attorney, Agent, or Firm* — Borden Ladner Gervais LLP

(57) ABSTRACT

A process and system for producing a synthetic hydrocarbon having a desired H/C ratio is disclosed. Organic material is biochemically digested in a two stage biodigester for separately producing a hydrogen containing biogas substantially free of methane in a first stage and a methane containing biogas in a second stage. The methane containing biogas is reformed in a first reformer to generate hydrogen gas and carbon monoxide gas, which are then combined in a mixer with the hydrogen containing biogas into a syngas in amounts to achieve in the syngas an overall H/C ratio substantially equal to the desired H/C ratio. The syngas is reacted with a catalyst in a second reformer, a Fischer-Tropsch (FT) reactor, to produce the hydrocarbon. Using a two stage biodigester allows for the generation of separate hydrogen and methane streams, a more economical generation of the FT syngas and reduced fouling of the FT catalyst.

5 Claims, 26 Drawing Sheets

(51) Int. Cl.
C12M 1/00 (2006.01)
C12P 3/00 (2006.01)
C12P 5/02 (2006.01)

(52) U.S. Cl.
CPC ............ C12M 23/58 (2013.01); C12M 43/00 (2013.01); C12P 3/00 (2013.01); C12P 5/023 (2013.01); *Y02E 50/343* (2013.01); *Y02P 30/30* (2015.11)

(56) References Cited

U.S. PATENT DOCUMENTS

| | | | |
|---|---|---|---|
| 7,985,710 | B2 | 7/2011 | Wang et al. |
| 8,088,187 | B2 | 1/2012 | Mohedas et al. |
| 8,431,507 | B2 | 4/2013 | Bezemer et al. |
| 8,444,725 | B2 | 5/2013 | Agrawal et al. |
| 8,500,829 | B2 | 8/2013 | Siskin et al. |
| 8,502,003 | B2 | 8/2013 | Siskin et al. |
| 8,952,076 | B2 | 2/2015 | Rytter et al. |
| 8,969,231 | B2 | 3/2015 | Rytter et al. |
| 9,180,436 | B1 | 11/2015 | Espinoza et al. |
| 2008/0115415 | A1 | 5/2008 | Agrawal et al. |
| 2008/0167391 | A1 | 7/2008 | Schrauwen |
| 2009/0247393 | A1 | 10/2009 | Bezemer et al. |
| 2009/0314993 | A1 | 12/2009 | Zhang et al. |
| 2010/0099780 | A1 | 4/2010 | Rytter et al. |
| 2012/0079767 | A1 | 4/2012 | Aplin et al. |
| 2013/0264264 | A1 | 10/2013 | Lehoux et al. |

FOREIGN PATENT DOCUMENTS

| | | | |
|---|---|---|---|
| WO | 03066517 | A1 | 8/2003 |
| WO | 2007108014 | A1 | 9/2007 |
| WO | 2009158028 | A2 | 12/2009 |
| WO | 2011031752 | A2 | 3/2011 |

OTHER PUBLICATIONS

Hawkes, F. R. et al., "Sustainable fermentative hydrogen production: challenges for process optimisation", International Journal of Hydrogen Energy, vol. 27, Issues 11-12, Nov.-Dec. 2002, pp. 1339-1347.

Hafez, Hisham et al., "Biological hydrogen production from corn-syrup waste using a novel system", Energies 2009, vol. 2 (2), Jun. 24, 2009, pp. 445-455.
Hafez, Hisham et al., "Effect of organic loading on a novel hydrogen bioreactor", International Journal of Hydrogen Energy, vol. 35, Issue 1, Jan. 2010, pp. 81-92.
International Application PCT/CA2015/051366, Internal Search Report and Written Opinion dated Mar. 15, 2016.
Levin, David B. et al., "Biohydrogen production: prospects and limitations to practical application", International Journal of Hydrogen Energy, vol. 29, Issue 2, Feb. 2004, pp. 173-185.
O-Thong, Sompong et al., "Evaluation of methods for preparing hydrogen-producing seed inocula under thermophilic condition by process performance and microbial community analysis", Bioresource Technology, vol. 100, Issue 2, Jan. 2009, pp. 909-918.
Show, Kuan-Yeow et al., "Critical assessment of anaerobic processes for continuous biohydrogen production from organic wastewater", International Journal of Hydrogen Energy, vol. 35, Issue 24, Dec. 2010, pp. 13350-13355.
Show, Kuan-Yeow et al, "Production of hydrogen in a granular sludge-based anaerobic continuous stirred tank reactor" International Journal of Hydrogen Energy, vol. 32, Issue 18, Dec. 2007, pp. 4744-4753.
Vavilin, V. A. et al., "Modelling hydrogen partial pressure change as a result of competition between the butyric and propionic groups of acidogenic bacteria", Bioresource Technology, vol. 54, Issue 2, Accepted for Publication Aug. 26, 1995, pp. 171-177.
Wu, Shu-Yii et al., "HRT-dependent hydrogen production and bacterial community structure of mixed anaerobic microflora in suspended, granular and immobilized sludge systems using glucose as the carbon substrate", International Journal of Hydrogen Energy, vol. 33, Issue 5, Mar. 2008, pp. 1542-1549.
Zhang, Zhen-Peng et al., "The role of acid incubation in rapid immobilization of hydrogen-producing culture in anaerobic upflow column reactors", International Journal of Hydrogen Energy, vol. 33, Issue 19, Oct. 2008, pp. 5151-5160.
Zhang, Zhen-Peng et al., "Rapid formation of hydrogen-producing granules in an anaerobic continuous stirred tank-reactor induced by acid incubation", Biotechnology and Bioengineering, www.interscience.wiley.com, Published online Nov. 6, 2006, pp. 1040-1050.
EP 2483371A2 Published as WO2011031752, Aug. 8, 2012, 2 pgs.
International Patent Application No. PCT/CA2015/051366, International Preliminary Report on Patentability dated Mar. 24, 2017.

Cumulative methane yield as L CH₄ per kg of poplar feedstock added (Stage One)

Cumulative methane yield as L CH₄ per kg of corn stover feedstock added (Stage One)

Cumulative methane yield as L CH₄ per kg of soft wood feedstock added (Stage One)

Cumulative methane yield as L CH₄ per kg of poplar feedstock added (stage Two)

Cumulative methane yield as L CH$_4$ per kg of corn stover feedstock added (stage Two)

Cumulative hydrogen yield as LH$_2$ per kg of poplar feedstock added (Stage One)

Cumulative hydrogen yield as LH$_2$ per kg of corn stover feedstock added (Stage One)

Cumulative hydrogen yield as LH₂ per kg of soft wood feedstock added (Stage One)

Cumulative hydrogen yield as L H$_2$ per kg of poplar feedstock added (stage Two)

Cumulative hydrogen yield as L H₂ per kg of corn stover feedstock added (stage Two)

CONVERSION OF BIOMASS, ORGANIC WASTE AND CARBON DIOXIDE INTO SYNTHETIC HYDROCARBONS

FIELD OF THE INVENTION

This application claims priority from Provisional U.S. Patent Application No. 62/096,146, which was filed on Dec. 23, 2014.

The present invention relates generally to the production of non-fossil based synthetic hydrocarbons and in particular to processes and apparatus for converting organic material from varied sources, into synthetic hydrocarbons, for example renewable liquid fuels.

BACKGROUND

It has proven difficult to create an economically sustainable process for large-scale production of renewable liquid fuels from biomass and organic waste. Biological processes are under development but are very complex, since they require constant monitoring and strict control of the process conditions and the balance of organisms and food. Thermochemical conversion processes are also in development, but those processes are subject to catalyst degradation/deactivation over time.

Biological processes for the production of alcohol based liquid fuels (methanol, ethanol, propanol and butanol) from lignocellulosic biomass (as opposed to grain based processes) are numerous but are not commercially viable on a large scale. Biological processes for the generation of drop-in liquid fuels (gasoline, jet and diesel fuels) from biomass usually require a designer/genetically modified microorganism as the basis of the technology, which may not be reliable at industrial scale. Of the conventional grain based biological ethanol fuel processes in operation, most generate biogenic carbon dioxide ($CO_2$) gas as a byproduct. Although this carbon dioxide gas is biogenic and non-fossil, it nevertheless adds to global $CO_2$ emissions. Thus, a non-fossil energy conversion method to recycle the $CO_2$ into a renewable liquid fuel, which would have a positive effect on global greenhouse gas emissions, would be desirable.

Anaerobic digestion is a type of biochemical process in which chemical reactions carried out by various microorganisms, so called biochemical reactions, are used to decompose organic matter in the absence of oxygen. The process of anaerobic digestion is normally used for waste water treatment systems and other watery organic material treatment systems, as long as the solids can be introduced to the system at an acceptable concentration for sustaining the anaerobic digestion. That concentration is less than 2%. The products of biochemical digestion are biogases, which can be used as a clean and renewable form of energy which can be a substitute for conventional sources of energy which may be causing ecological and/or environmental problems and at the same time are depleting at a faster rate.

Various types of pretreatment technologies have been explored to enhance the rate-limiting hydrolysis step in anaerobic digestion, including mechanical, thermal, chemical, and biological pretreatment for liquefaction of certain biomass components. However, the compositional variations between biomass types cause changes in composition and yield of the products of liquefaction since lignin, hemicelluloses, and cellulose react differently during pretreatment.

Woody biomass materials that are by-products from activities such as forest harvesting, products manufacturing, construction, and demolition debris harvesting or management, are referred to as "wood residues". Wood residues can be inexpensive sources of biomass, and they are the most common biomass fuel for heat or power generation. It has been suggested that in the future, fast growing grasses, shrubs and tree hybrids (i.e. energy crops such as miscanthus and switchgrass) could be grown for use in the production of fuels or other products.

Known anaerobic digestion (AD) processes have limited utility for high-solids woody feedstocks and are subject to overgrowth of hydrogentrophic methanogens and acetogens, leading to reduced hydrogen yields and the production of unwanted by-products. Thus, significant dilution and careful adjustment of the feedstock solids to less than 2% solids content is normally required. Moreover, a capital intense reforming process is needed for conversion of the mixed biogas stream produced to syngas, especially for removal of any excess $CO_2$, which has a highly deleterious effect on a gas-to-liquid fuel (GTLF) process.

The Fischer Tropsch (FT) reaction is a known GTLF process for use in converting a syngas containing $H_2$ and CO into synthetic hydrocarbons. Several processes for the generation of FT syngas are known. Thermochemical processes for the conversion of biomass or organic wastes into syngas by thermally gasifying the feedstock are known and can be used to produce both alcohols and drop-in liquid fuels. However, such syngases have a high contaminant load, for example particulates such as char and condensable vapours such as those derived from fast pyrolysis and can also contain non-reactive gases.

The FT process requires the use of a catalyst. Most gas reaction catalysts are highly sensitive to particulate and/or vaporous contaminants entrained in the syngas and become quickly fouled by those contaminants. Any syngas containing such contaminants, must therefore be cleaned, often at significant cost, to achieve the high quality (high purity/cleanness) syngas required for reliable operation of the Fischer Tropsch (FT) reaction. Other contaminants in the syngas, such as non-reactive gases, for example $N_2$, $CO_2$, $CH_4$, $SO_2$ can also be detrimental to the FT process and, depending on the gas, can degrade the catalyst, decrease the catalyst production rate, or affect the desired product produced in the reactor by changing the $H_2/CO$ ratio entering the reactor. Absent any economical source of clean syngas with the proper $H_2/CO$ ratio, these problems render synthetic fuel production with Fischer Tropsch from thermochemically gasified biomass uneconomical and impractical.

The syngas required for the FT reaction can also be created commercially by reforming methane. A synthetic methane production process is known which uses atmospheric $CO_2$ and $H_2$ generated by water electrolysis. This process can be used to create renewable/non-fossil methane if renewable or nuclear electricity is used. However, high electricity costs render this process uneconomical on a large continuous scale, unless excess renewable electricity is available. Yet, the supply of excess renewable electricity is erratic and often unpredictable, making its use in a stand-alone process economically difficult, if not impractical, due to large swings in the amount of energy available.

In a first methane reforming process, the "wet" reforming process (SRM), water is reacted with methane in a catalytic reformer reactor, to carry out the following basic reaction:

$$CH_4 + H_2O = 3H_2 + CO.$$

This results in a 3 to 1 molar ratio of $H_2$ and CO in the syngas.

In a second methane reforming process, the "dry" (DRM) reforming process, $CO_2$ is reacted with $CH_4$ in a catalytic process according to the basic reaction $$CO_2+CH_4=2H_2+2CO.$$

This results in a 1 to 1 molar ratio of $H_2$ and CO in the syngas. The more $CO_2$ is used to replace $H_2O$ in the methane reformer, the more "dry" the process will be, i.e. the less water will be used and the molar ratio between $H_2$ and CO will vary from a low of 1 (completely dry reaction) to a high of 3 (completely wet reaction). The overall reactions which take place at the same time in reforming are as follows:

$$CH_4+H_2O \leftrightarrow CO+3H_2$$

$$\Delta H_{298}^\theta = +206 \text{ kJ} \cdot \text{mol}^{-1}$$

$$CH_4+2H_2O \leftrightarrow CO_2+4H_2$$

$$\Delta H_{298}^\theta = +165 \text{ kJ} \cdot \text{mol}^{-1}$$

$$CO+H_2O \leftrightarrow CO_2+H_2$$

$$\Delta H_{298}^\theta = -41 \text{ kj} \cdot \text{mol}^{-1}$$

$$CH_4+CO_2 \leftrightarrow 2H_2+2CO$$

$$\Delta H_{298}^\theta = +247 \text{ kJ} \cdot \text{mol}^{-1}$$

Although dry ($CO_2$) reforming of methane (DRM) is a well-studied reaction that has both scientific and industrial importance, significant technical hurdles still exist with DRM utilization. The DRM reaction requires high temperatures (about 900 C) and is highly endothermic (20% more than the pure SRM reaction), thereby requiring significant amounts of high grade energy for total reactant conversion. In addition, severe catalyst degradation occurs due to carbon deposition. Since molecular carbon formation is a common problem of the known DRM process, significant amounts of water are always used resulting in a process which is mostly wet, i.e. it is a slightly modified SRM process, not a mostly dry or DRM process. This means that water supplies most of the oxygen for the CO in the syngas. That makes existing processes environmentally costly as it is environmentally beneficial to split a $CO_2$ molecule which would otherwise enter the atmosphere adding to the greenhouse effect rather than splitting $H_2O$, but doing so means 20% more reforming energy will need to be used.

Thus, an improved process for the production of liquid hydrocarbon fuels from non-fossil sources would be desirable.

SUMMARY OF THE INVENTION

It is now an object of the invention to address at least one of the disadvantages of prior systems and methods for the production of synthetic fuels from organic materials, for example renewable organic materials.

This invention focuses on a process and system for the production of non-fossil based synthetic hydrocarbons, from organic material, for example sustainable biomass sources. The synthetic hydrocarbons that can be produced from sustainable biomass sources by the process of the invention are, for example, an array of renewable synthetic fuel products such as transportation fuels and derivatives thereof, such as chemicals, and plastics.

The invention provides a process and system using biochemical/anaerobic digestion of organic material for the separate production of hydrogen and methane biogases to create a clean syngas, preferably separate clean streams of hydrogen containing biogas, methane containing biogas and $CO_2$ syngas. Producing hydrogen biogas and methane biogas separately facilitates their mixing in a desired molar ratio other than the one at which they are produced from the organic material during anaerobic digestion. Creating a separate methane biogas also facilitates methane reforming to CO and $H_2$ for the creation of a clean syngas for FT synthesis.

In particular, the present process uses a two stage anaerobic digestion of organic material for the production of separate streams of hydrogen containing biogas (substantially free of methane) and methane containing biogas. This allows for an improved control of the hydrogen and methane gases and, thus, the methane reforming step, the H/C ratio in the FT syngas and ultimately the H/C ratio in the final synthetic hydrocarbon product. In the step of biochemically digesting, the organic material is subjected to a multiple stage anaerobic digestion including a first stage for producing the hydrogen containing biogas substantially free of methane and at least a second stage for producing the methane containing biogas.

In one exemplary embodiment, the invention provides a process for producing a synthetic hydrocarbon having a desired H/C ratio, comprising the steps of a) biochemically digesting organic material for separately producing a hydrogen containing biogas substantially free of methane and a methane containing biogas, b) reforming the methane containing biogas to generate hydrogen gas and carbon monoxide gas, and c) combining the hydrogen containing biogas, the hydrogen gas, the methane containing biogas and the carbon monoxide gas into a syngas in amounts to achieve in the syngas an overall H/C ratio substantially equal to the desired H/C ratio required to produce the synthetic hydrocarbon; and d) operating a Fischer-Tropsch synthesis by reacting the syngas with a catalyst to produce the synthetic hydrocarbon.

To maximize the range of available organic materials that can be used and the potential use of excess $CO_2$ available, the production of $H_2$ from biomass can be supplemented with $H_2$ derived from water electrolysis, preferably carried out with excess renewable or non-fossil electricity.

Although the Fisher Tropsch (FT) synthesis for the production of synthetic hydrocarbons is known, current thermochemical processes for the generation of a FT syngas require significant amounts of energy. The process of the present application uses biochemical digestion of organic materials for the generation of a clean syngas. This reduces the energy requirements of the syngas generation step, since the energy required for the biochemical process is derived from the biomass itself.

The organic material digested in the process is a hydrocarbon containing material suitable for biochemical (f. ex. anaerobic, microbial and/or bacterial) digestion. Exemplary organic materials include any one of cellulosic materials, lignocellulosic materials, wastes, such as wood processing wastes, agricultural residues, municipal green bin collections, manures, an effluent from a cellulosic material processing plant, an effluent from a paper plant, an effluent from an ethanol-from-biomass process, thin or whole stillage, dry distillers grains, and biodegradable waste waters. For example, the organic material may include a mixture of a biomass and another biodegradable material suitable for anaerobic digestion.

The organic material can be lignocellulosic biomass. If lignocellulosic biomass is to be digested, the step of biochemically digesting preferably includes the further step of subjecting the lignocellulosic biomass to a pretreatment selected from particle size reduction in an extruder, chemical pretreatment, thermal pretreatment, thermochemical pretreatment, steam explosion pretreatment, dual stage or single stage hydrothermal pretreatment for hydrothermal liquefaction and hydrolysis of hemicellulose in the biomass, thermomechanical pretreatment, and combinations thereof.

The preferred pretreatment is single or dual stage hydrothermal pretreatment for hydrothermal liquefaction and partial hydrolysis of hemicellulose in the biomass, prior to anaerobic digestion.

In an exemplary process in accordance with the invention, either one or both of the hydrogen containing biogas and the methane containing biogas can include carbon dioxide. In a variant of that process, the first stage of the anaerobic digestion, the hydrogen biogas production stage, includes the further step of continuously sequestering carbon dioxide for increasing a rate of hydrogen production in the first stage and for generating hydrogen containing biogas substantially free of methane and substantially free of $CO_2$. Having a clean hydrogen gas source available facilitates control of the H/C ratio of the syngas produced, for example for the FT synthesis step.

In the combining step c) of the exemplary process, additional methane gas (free of $CO_2$) may be added into the syngas in an amount to achieve or maintain the overall H/C ratio in the syngas. This can be advantageous if carbon monoxide is added into the syngas from a source other than methane reforming.

In the reforming step b) of the exemplary process, the methane containing biogas is preferably reacted with a catalyst to produce the syngas containing hydrogen and carbon monoxide. The catalyst may be a dry reforming catalyst or a wet reforming catalyst. If a dry reforming catalyst is used, the methane containing biogas, which includes a methane component and a carbon dioxide component, is subjected to the catalyst so that both components are reacted with the dry reforming catalyst for dry reforming the methane into hydrogen and carbon monoxide. A combination of dry and wet reforming may also be used.

In one embodiment, additional carbon dioxide sourced separately from the methane containing biogas is added to the methane containing biogas as hydrogen gas becomes available from any source. The additional carbon dioxide may be derived from a separate process such as a grain based ethanol process, or captured from the atmosphere.

If a wet reforming catalyst is used, the methane containing biogas can be reacted with water in presence of the wet reforming catalyst for wet reforming the methane into hydrogen and carbon monoxide.

In a variant of the reforming step b) the methane containing biogas is first divided into first and second partial streams for separate reforming, whereby the first partial stream is reacted with a dry reforming catalyst and carbon dioxide for dry reforming of the methane and the second partial stream is reacted with water and a wet reforming catalyst for wet reforming of the methane. This variant of the reforming step can be advantageously used to control the overall $H_2/CO$ ratio achieved by the combined dry reforming and wet reforming by adjusting a volume ratio of the first and second partial streams for modifying the volume ratio of hydrogen and carbon monoxide produced.

In the variant of the exemplary process in which carbon dioxide is continuously sequestered during the biochemical digestion step a), additional hydrogen gas, generated by water electrolysis using non fossil excess electricity, can be advantageously used for consuming additional carbon dioxide beyond that which is produced in the biochemical digestion. The carbon dioxide may be sourced, for example, from a corn/grain ethanol plant or other fermentation processes and reacted with the additional hydrogen gas for producing additional carbon monoxide gas and the additional hydrogen gas and carbon monoxide gas can be used for adjustment of the H/C ratio in the FT syngas. The water electrolysis is preferably carried out using excess electricity and/or renewable electricity. Hydrogen and oxygen produced by water electrolysis using excess and/or renewable electricity may also be used for the generation of heat to be supplied to the methane reforming step internally in a process called partial oxidation or POX, if the stoichiometric ratios of C, H and O are otherwise met to provide the desired H/C syngas ratio for the desired FT synthetic hydrocarbon.

As more renewable electricity generation is installed to cover even peak demand, the gap between renewable electricity supply and actual electricity demand in the grid widens during off peak times, resulting in excess renewable electricity. Various approaches for storing this excess electricity exist, but the process in accordance with the invention creates an opportunity to store the excess electricity in the form of liquid renewable fuels. The inventors of the present process have now developed an overall system which combines biological, thermochemical and electrochemical processes into one system which can convert biomass/organic waste/$CO_2$/excess electricity into renewable liquid fuels or other synthetic hydrocarbons.

The creation of a syngas via a combination of dry and/or wet reforming of biogas generated by multiple stage anaerobic digestion (AD) of renewable and waste organic materials allows for the generation of synthetic liquid drop-in fuels, for example diesel, gasoline, and jet fuel as fossil fuel substitutes, using the Fischer-Tropsch (FT) process as the raw biogas contains $CH_4$, $CO_2$ and $H_2$. When the AD is performed in 2 stages for the generation of separate $H_2$ and $CH_4$ gas streams, syngas with the proper H/C ratio, or equivalent molar ratio of $H_2/CO$ can be more economically produced than with conventional methods and reacted over a FT catalyst to form higher molecular weight compounds, including substitutes for conventional gasoline, jet and diesel fuels. $H_2$ and $CH_4$ biogas produced by AD, especially 2 stage AD is substantially free of catalyst fouling contaminants, such as particulates and condensable volatiles. The FT process is theoretically capable of producing liquid hydrocarbons from syngas generated from organic materials in anaerobic digestion. FT liquid fuel products are free of sulfur and therefore allow the use of catalytic control of combustion emissions, especially NOx and SOx, significantly reducing greenhouse gas effects when those fuel products are burned for energy.

Hydrothermal (HT) pretreatment can be used to enhance the rate-limiting hydrolysis step in anaerobic digestion (AD) and this is especially true for organics in solid form such as lignocellulosic or 'woody' biomass. Known HT processes include liquid hot water (LWH) pretreatment and steam explosion pretreatment (STE). The reaction mechanism occurring in HT processing is complex due to the compositional variations between biomass types, which cause changes in composition and yield of the products of liquefaction since lignin, hemicelluloses, and cellulose degrade differently during hydrothermal liquefaction. These challenges have to date prevented the successful commercial use of a single HT pretreatment for the production of feedstocks for AD. The inventors have now developed a HT pretreatment for integrated use with an AD process and pretreatment of various different biomass types.

The process of the present application can integrate a series of processing technologies to provide renewable jet, diesel, naphtha or alcohol based ethanol or methanol fuels, from renewable feedstocks, such as cellulosic feedstocks, corn and other grains and/or a variety of non-food-grade feedstocks and/or food/human/animal wastes. In addition, besides the obvious renewable nature of the fuel products from the proposed process due to the type of feedstocks to be utilized, the process relies on $CO_2$ as one of the main feedstocks for the gas-to-liquid conversion process, especially when it is the by-product from ethanol manufacturing and anaerobic digestion (AD). This significantly improves the carbon footprint and economics of the hydrocarbon products produced with the process of the invention, compared to conventional processes for synthetic hydrocarbon production from organic matter.

In another embodiment, the invention provides a system for producing a synthetic hydrocarbon having a desired H/C ratio. The system includes a two stage biodigester, a first reformer for reforming methane, a mixer for producing syngas and a second reformer for carrying out a Fischer Tropsch (FT) synthesis. The two stage biodigester provides for biochemically digesting organic material in a first stage into a hydrogen containing biogas substantially free of methane and in a second stage into a methane containing biogas. The first reformer provides for reacting the methane containing biogas with a catalyst to produce a carbon monoxide gas and hydrogen gas. The a mixer provides for combining the hydrogen containing biogas, the hydrogen gas and the carbon monoxide gas into a FT syngas in amounts to achieve the desired H/C ratio in the FT syngas. The second reformer provides for operating a Fischer-Tropsch synthesis by reacting the syngas with a catalyst to produce the synthetic hydrocarbon.

Preferably, the two stage biodigester includes a first stage bioreactor including the organic material and anaerobic microorganisms and having an effluent drain, a separator for separating the first effluent exiting the effluent drain of the first bioreactor into separated biomass and a second effluent, a return conduit for recycling a portion of the separated biomass from the separator back into the first bioreactor, a second stage fluidized bed bioreactor receiving the second effluent and a remainder of the separated biomass, and a controller for adjusting a fluid throughput of the first and second bioreactors for decoupling in the first bioreactor the solids retention time from the hydraulic retention time for minimizing growth of hydrogentrophic methanogens in the first bioreactor.

In a variant of the system, the first bioreactor includes a carbon dioxide sequestering arrangement, for example in a headspace of the first bioreactor, for continuously sequestering carbon dioxide waste gas to increase a hydrogen production rate in the first bioreactor and to generate a hydrogen containing biogas substantially free of $CO_2$.

The first reformer preferably includes a catalyst for reforming the methane containing biogas.

In one embodiment of the system, the methane containing biogas includes a methane component and a carbon dioxide component and the catalyst of the first reformer is a dry reforming catalyst for reacting with both components and dry reforming the methane into hydrogen and carbon monoxide. The first reformer can further include a $CO_2$ gas feed for adding $CO_2$ gas to the methane containing biogas.

In another embodiment of the system, the catalyst of the first reformer is a wet reforming catalyst and the first reformer further includes a water input for mixing the methane containing biogas with water for reacting with the wet reforming catalyst for wet reforming the methane into hydrogen and carbon monoxide.

In yet another embodiment, the system further includes an electrolysis unit for receiving excess renewable electricity and generating $H_2$ gas and $O_2$ gas from water using the excess renewable electricity; and a $H_2$ gas drain line for feeding the $H_2$ gas into the mixer for inclusion into the syngas.

In yet a further embodiment, the system further includes a separate $O_2$ addition to the reformer from the electrolysis unit for receiving separate $H_2$ and $O_2$ gas streams to create internal heat energy for the catalytic reaction for the splitting of the $CO_2$ molecule in the reforming reaction, the heat generation necessarily consuming $H_2$ upon producing water.

In one aspect, the biodigester is an integrated bioreactor clarifier system (IBRCS), allowing the use of high-solids feedstocks like cellulosic and lignocellulosic substrates. The first stage of the biodigester then preferably includes a carbon dioxide sequestration arrangement, for sequestering $CO_2$ directly from the reactor headspace to increase hydrogen yield, to reduce the growth of hydrogentrophic methanogens and acetogens, to increase utilization of $CO_2$ and to create a clean hydrogen containing biogas.

DETAILED DESCRIPTION OF EXEMPLARY EMBODIMENTS

Figure 1A:
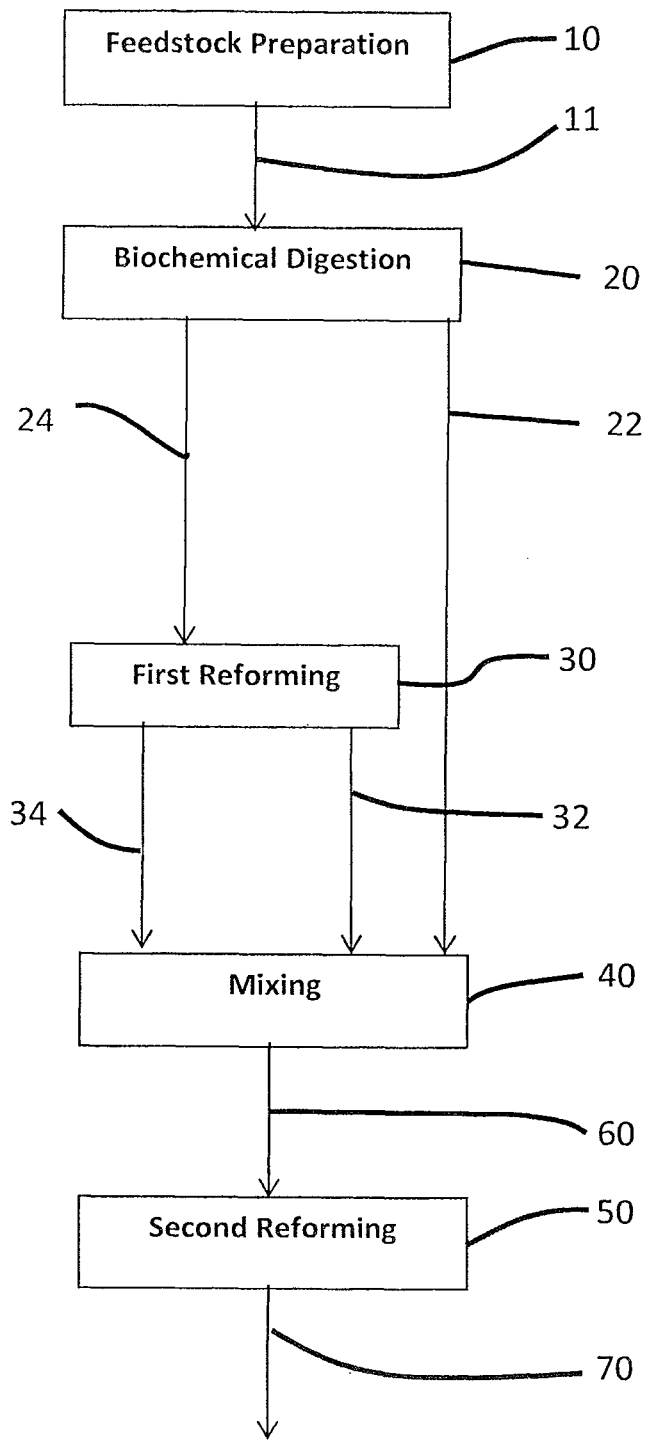
FIG. 1A schematically illustrates the general process in accordance with the present specification.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing an exemplary implementation of the various embodiments described herein.

Before explaining the present invention in detail, it is to be understood that the invention is not limited to the exemplary embodiments contained in the present specification. The invention is capable of other embodiments and of being practiced or carried out in a variety of ways. It is to be understood that the phraseology and terminology employed herein are for the purpose of description and not of limitation.

As used herein, the terms "about" and "approximately" are used in conjunction with ranges of dimensions, concentrations, temperatures, or other physical or chemical properties and characteristics. Use of these terms is meant to cover slight variations that may exist in the upper and lower limits of the values or ranges of properties and characteristics.

As used herein, the term "biochemical digestion" refers to processes for the decomposition of organic material by microorganisms. One type of biochemical digestion discussed in detail in this application is anaerobic digestion in which organic matter is decomposed by biochemical reactions carried out by various anaerobic microorganisms in the absence of oxygen.

Generally, the process of the present application includes the basic steps of a) biochemically digesting organic material in a biochemical digestion process for separately producing a hydrogen containing biogas stream and a methane containing biogas stream, whereby the hydrogen containing biogas is substantially free of methane;

b) reforming the methane containing biogas to generate carbon monoxide gas and hydrogen gas;

c) combining the hydrogen containing biogas, the hydrogen gas and the carbon monoxide gas to generate a syngas having a desired H/C ratio; and d) reforming the syngas operating a Fischer-Tropsch synthesis reacting the carbon monoxide and hydrogen with a catalyst to produce synthetic hydrocarbons having the desired H/C ratio.

The hydrogen containing biogass is preferably also substantially free of carbon dioxide.

As used herein, the term "organic material" refers to any material with carbon and hydrogen in its molecular structure, for example alcohols, ketones, aldehydes, fatty acids, esters, carboxylic acids, ethers, carbohydrates, proteins, lipids, polysaccharides, monosaccharide, cellulose, nucleic acids, etc. Organic material may be present for example, in waste (e.g. agricultural or industrial waste streams; sewage sludge), organic fluid streams, fresh biomass, pretreated biomass, partially digested biomass, etc.

As used herein, the term "hydrogen containing biogas substantially free of methane" refers to a hydrogen containing biogas including at least 95% $H_2$. Preferably the hydrogen containing biogas contains 99% $H_2$ and up to 1% of trace gases such as $H_2S$ and water vapor.

As used herein, the term "substantially free of $CO_2$" refers to a biogas containing less than 5% $CO_2$, preferably less than 1% $CO_2$ and most preferably no $CO_2$.

The term biomass includes lignocellulosic biomass, for example wood based residues, which are classified into three categories: forest residues, urban residues, and mill residues. Although wood-based residues can be and are used as raw material, their conversion to alternative forms (liquid, solid and/or gas) i.e. using hydrothermal pretreatment and anaerobic digestion have the potential to greatly facilitate the use of this biomass as an energy provider, and for the synthesis of value-added chemicals.

Pulp mills all over the world are looking at ways to improve their bottom line through the addition of new value added products and/or new process efficiencies. The process of the present application which can use mill residues as an organic material feedstock for synthetic hydrocarbon production. The present process can also be used to capture biogenic non-fossil $CO_2$ emissions from fermentation based fuel ethanol plants.

As used herein, the term "hydrothermal pretreatment (HT)" refers to known lignocellulosic biomass pretreatment processes using water or steam at elevated temperatures and/or pressures. Exemplary HT processes include Liquid Hot Water pretreatment (LHW) and Steam Explosion pretreatment (STE).

The biochemical digestion process is a two-stage anaerobic digestion process (AD) producing the hydrogen containing biogas in the first stage and the methane containing biogas in the second stage. The hydrogen component in the syngas can include pure bio-hydrogen from the 1st stage of the 2-stage AD system when $CO_2$ sequestration is used in the first stage, or additional hydrogen gas from the electrolysis of water, if required, to optimize and or control the molar ratio of $H_2/CO$ in the syngas, subject to the availability of biomass feedstocks and/or the availability of surplus electrical energy. Depending on the amount of surplus electrical energy available and the composition of the biomass available at the time, the surplus electricity can also supply hydrogen and oxygen as part of the syngas reformer feedstock to reduce the external heat required from other sources, for example combustion of airless dried carbon containing AD residues. Hydrogen produced by excess electricity can also be used on its own or with external $CO_2$ sources as additional feedstock for the second stage of the two stage AD to create additional methane gas. In this second stage, the microbes of the AD process biologically/biochemically create methane from the additional feedstock in a fluidized bed reactor type digester. A clean syngas stream is produced from the hydrogen containing biogas, the hydrogen gas and the carbon monoxide gas at the proper molar ratio for the hydrocarbon products of choice and is then converted to hydrocarbons by operating a Fischer-Tropsch synthesis reaction, reacting the carbon monoxide and hydrogen with a catalyst.

An exemplary waste biorefinery implementation of the present invention is a "bolt-on" system for the refining of waste streams of existing paper mills or grain ethanol plants in order to reduce overall capital costs. The most economical time to perform this bolt-on would be, for example, when specific pieces of equipment in the plants need to be replaced or upgraded such as the DDGS dryers in ethanol plants or the digesters and the black liquor boilers in paper mills. Existing pulp mills may use the system of the invention as a bolt-on facility to an existing pulp mill with the goal to produce drop-in renewable liquid transportation fuels from pre-hydrolysate liquor (PHL), pulp waste waters and forest wood products including forest slash feedstocks, thereby generating a significant new revenue stream for the mill. Similarly, a waste biorefinery application of the invention can also be used as a bolt-on in the corn ethanol industry by utilizing corn stover and stillage as feedstock while eliminating DDGS dryers to produce the drop-in renewable fuels as noted. Other applications of the system of the invention for the processing of organic material containing waste streams of other industries, or for the processing of the waste waters and sludge from a sewage treatment plant, are readily apparent and will not be discussed in detail for the purpose of brevity.

In an exemplary fresh material biorefinery implementation, the process and system of the present application can be used for the processing of fresh biomass and includes the steps of hydrothermal pretreatment and anaerobic digestion (AD) of the biomass and gas-to-liquid conversion of the biogases produced in the AD, in particular hydrogen gas and carbon dioxide. The inventors have also developed processing conditions and parameters for improved biodegradability of the biomass in a downstream AD process, as will be discussed in more detail below.

A combined biorefinery implementation which is a combination of the organic waste biorefinery implementation with the fresh product biorefinery implementation is also possible. Generally, fresh biomass and/or waste materials, such as organic waste materials from ethanol or food production, forestry waste materials, human waste, or other hydrocarbon containing waste materials suitable for bacterial digestion, are used in such a combined biorefinery process. In that process, the fresh biomass and waste materials are combined and pretreated in an extrusion/hydrothermal process to generate organic matter ready for anaerobic digestion. Next is a two-stage anaerobic digestion (AD) process focused on the production of hydrogen containing biogas separate from methane containing biogas and preferably the production of hydrogen containing biogas free of $CO_2$. The hydrogen containing biogas and methane containing biogas are produced in separate stages. Using a co-digestion approach, this AD process provides for the simultaneous conversion of a variety of different feedstocks to renewable hydrogen containing biogas and methane containing biogas. These biogases are then fed to a dry reforming process that utilizes carbon dioxide to produce syngas i.e. hydrogen and carbon monoxide, the main building blocks of any synthetic hydrocarbon or synthetic fuel. The final step is a thermochemical synthesis process that converts the syngas into synthetic hydrocarbons, such as synthetic fuel and other renewable products.

The process of the present application for the first time integrates technologies previously not used in combination, i.e. hydrothermal pretreatment, two-stage anaerobic digestion, dry reforming, and gas-to-liquid fuel thermochemical synthesis using Fischer-Tropsch. This was made possible by specific modifications to one or more of the individual technologies. The resulting overall process thereby addresses practical problems encountered with these processes to date, which previously made their integration impossible or uneconomical.

Comparison to Bioethanol Production from Biomass

The process of the present invention is distinguished in several aspects from conventional biofuel production processes. For example, an ethanol biofuel production process, which uses yeast or other organisms to make ethanol, is susceptible to infection and yield degradation due to the sensitivity of the ethanol producing yeast organisms to substances in the sugar containing feed stream which are inhibitory or toxic to the yeast organisms and/or the hydrolyzing enzymes. These substances include glycerol, organic volatile fatty acids, lignin, furfural and hydroxymethylfurfural (HMF). C5 sugars, namely xylose, inhibit enzyme activity on the solid C6 sugars. Infection can be caused by competing organisms such as bacteria. Thus, bioethanol production requires extensive pre-treatment to produce "clean sugars" for digestion by the yeast, which is costly for non-food feedstocks such as wood, grasses and not practically possible for organic waste streams.

In contrast, in the anaerobic digestion of organic material in accordance with the present process bacterial cultures are used which including a multitude of different organisms that cooperate in digesting all types of sugars, proteins, fats and organic compounds, and other substances such as furfural and HMF, that are highly toxic to yeast, but not toxic to bacteria, at least not at the same concentration. Thus, pretreatment ahead of anaerobic digestion may be limited to providing improved access to the different components of lignocellulosic biomass. Controlling the generation of side products or degradation products may not be necessary, since those products may be digested by one or more of the different organisms in the anaerobic digestion reaction mixture. This, results in a generally less costly pre-treatment process and system, which produces "dirty sugars" (as far as yeasts are concerned) including other organic compounds. Those "dirty sugars" can be readily digested by bacterial cultures used in an AD system, as will be apparent from the examples discussed further below.

Conventional bioethanol processes for non-food feedstocks require separate enzymatic hydrolysis for liquid C5 and solid C6 sugars, which involves high capital expenditure due to large multiple tankage and mixing requirements and high operating costs due to enzyme cost and electricity cost. In contrast, the bacteria used in the present AD process produce their own enzymes for hydrolysis, especially for the digestion of C6 solids and C5 liquid, oligomeric sugars that cannot be digested by yeast. Electrical energy requirements for mixing may also be greatly reduced in a 2-stage AD system as the system can achieve lower retention times and may use an optimized fluidized bed reactor.

In a conventional bioethanol process, biogenic carbon dioxide is generated which is generally released to the atmosphere, while in the anaerobic digestion process of the invention biogenic carbon dioxide generated during anaerobic digestion can be fully reused in the modified flexible reforming process, thereby in effect reducing greenhouse gases. Even biogenic $CO_2$ from sources external to the process may be used in the process of the present application. Biomass degradation can create inhibitors for the hydrolysis and fermentation steps of conventional bioethanol production. Thus, in a conventional bioethanol process, biomass stored prior to processing must be protected from degradation by rot. In contrast, rotting biomass can readily be digested in an anaerobic digestion process without inhibition occurring.

Comparison to Thermochemical Biofuel Production

The process of the present invention is distinguished in several aspects from conventional thermochemical biofuel production processes. For example, a thermochemical biofuel production process requires an extensive pre-treatment system (chopping and drying) in order to achieve optimal thermal conversion of the biomass into syngas. In contrast, the present process, depending on the type of feedstock used, requires no drying and may require only a single stage pre-treatment.

An optimized conventional thermochemical biofuel process requires an "in-direct" heat transfer mechanism (heat exchanger) in order to eliminate dilution of the syngas with nitrogen, or otherwise requires the use oxygen for combustion which is costly, difficult to control and maintain, and generates excess carbon dioxide which is released to the atmosphere. In contrast, the biogases generated in the present process are free of air and/or nitrogen. The digester is preferably run at a slightly positive pressure, and all carbon dioxide produced during AD is preferably captured for potential use in the downstream reforming process.

In a conventional thermochemical biofuel process, the syngas must be cleaned of all particulates at significant expense, since the FT syngas to liquid fuel conversion process utilizes a catalyst which is extremely susceptible to even minor amounts of contamination from all types of sources that include particulates of unreacted biomass, particulates of char, particulates of the minerals that were in the biomass and minor aerosols/liquids/tars of partially reacted biomass that are in the syngas. In contrast, the AD biogases generated in the present process are practically free from particulates, aerosols or tars and only minimal cleaning may be required, mostly for potential Sulphur compounds.

In the conventional thermochemical biofuel process, biomass needs to be stored as dry as possible as all water needs to be boiled off before the thermochemical conversion takes place. This creates unnecessary energy requirements. In contrast, the present AD process requires water so water content is not an issue.

In a conventional thermochemical biofuel process, it is difficult to balance the $H_2/CO$ ratio using only biomass and water as the starting compounds to get a consistent and precise FT reaction to produce the desired hydrocarbon with minimal unreacted syngas as the three main atoms, carbon, hydrogen and oxygen are not completely independent. Furthermore biomass has a significant amount of oxygen contained in it (40% mass basis) and the gasification process creates significant amounts (20% molar basis) of unwanted $CO_2$ which must be removed and is often discarded/emitted to the atmosphere, resulting in 30% to 50% of the carbon in the biomass not being utilized. In contrast, in the process of the present application, practically all of the carbon in the biomass is either used to generate heat for the process or is incorporated into the synthetic fuel.

The two-stage AD process is used for the first time for the generation of FT syngas, the two stage process of the invention generates hydrogen containing biogas substantially free of methane and a separate methane biogas in the second stage, all substantially free of particulates and many other catalyst contaminates. This for the first time makes the integration of the AD and FT processes economically feasible and technically possible. Reduced reforming cost and high throughput capacity can also drastically reduce the capital footprint. The high biogas productivity of a two-stage AD process adds to the economic advantages of the overall process.

In the bio-hydrogen based system of the present application, the hydrogen containing biogas is preferably cleaned with $CO_2$ sequestration. The resulting clean hydrogen containing biogas allows multiple ways for adjusting the molar ratio with an independent supply of clean $H_2$ to trim the ratio prior to the FT reaction, which allows for a continuous and precise control of the syngas H/C ratio. As a result a more consistent mixture of hydrocarbon products with minimal unreacted syngas components can be achieved. Starting the reforming process with a supply of hydrogen rather than a supply of CO has the advantage that the $H_2/CO$ mixture can be adjusted more easily, since both the hydrogen stream and the CO stream can be supplemented from external sources. More importantly, by separating the hydrogen containing biogas from the methane containing biogas in the two-stage AD process, CO production can be controlled separately from $H_2$ production in the AD and in the subsequent flexible reforming steps. Any shortfall in CO and/or $H_2$ can then be supplemented from reformed $CO_2$ and/or through the use of excess electricity, especially excess renewable electricity used for water electrolysis. Since the amount of CO and $H_2$ produced by dry and/or wet reforming of the methane biogas can be tightly controlled, so can the ratio of the CO and $H_2$ in the syngas ($H_2/CO$) by combining the $H_2$ containing biogas and the CO and $H_2$ gases from the reforming step. Although a separate clean $H_2$ stream can be produced using the electro-hydrolysis of water, that approach uses vast amounts of electrical energy and is only economical if excess electricity is available. In contrast, all energy required for generation of the $H_2$ containing biogas in the present process may be derived by the microorganisms from the renewable organic material itself.

In a conventional thermochemical biofuel process, an extensive water clean-up system is required and dirty FT water is usually treated in an AD digestion system to clean the water for discharge to the environment. In contrast, in the present system, dirty FT water is re-directed back into the feedstock for the 2-stage AD for bio-hydrogen production. Thus, clean-up of the FT water is combined with producing clean gas molecules ($H_2$, $CH_4$, $CO_2$) for conversion into clean syngas so that in essence the cleanup of the water off the FT stage for discharge of excess water to the environment is already included in the front end syngas creation system. Of course, performing two functions with one piece of equipment represents the best possible use of capital equipment.

General Process

The general process in accordance with the present specification for converting organic material to synthetic hydrocarbons is schematically illustrated in FIG. 1. The general process includes the steps of feedstock preparation 10 for generating a feedstock 11, biochemical digestion 20 of the feedstock 11 into a hydrogen containing biogas 22 which contains mainly hydrogen ($H_2$) and optionally carbon dioxide ($CO_2$) and is substantially free of methane, and a separate methane containing biogas 24 which contains mainly methane ($CH_4$) and $CO_2$, a flexible reforming step 30 in which the methane biogas 24 is reformed into hydrogen gas 32 and carbon monoxide gas 34, a mixing step 40 in which the pure hydrogen gas 32 and the carbon monoxide gas 34 are combined into a syngas 60 with a desired molar $H_2/CO$ ratio, or an equivalent atomic H/C ratio, which syngas 60 is reformed in a Fisher Tropsch (FT) process into a synthetic hydrocarbon 70 with the desired H/C ratio. The feedstock preparation step 10 may include a process for the pretreatment of biomass, for example lignocellulosic biomass as will be discussed in more detail with reference to FIGS. 1A-1F and 8. Feedstock preparation can also include the sourcing and possible combination of different organic waste streams, with one another or with a biomass stream, as will be discussed in more detail in relation to FIG. 4. The biochemical digestion step 20 preferably includes a two-stage anaerobic digestion as discussed in more detail with reference to FIGS. 2 and 3. The first reforming step 30, the mixing step 40 and the second reforming step 50 are discussed in more detail below with reference to FIGS. 6, 7A, 7B, 7C and 8.

Overall System

Figure 4:
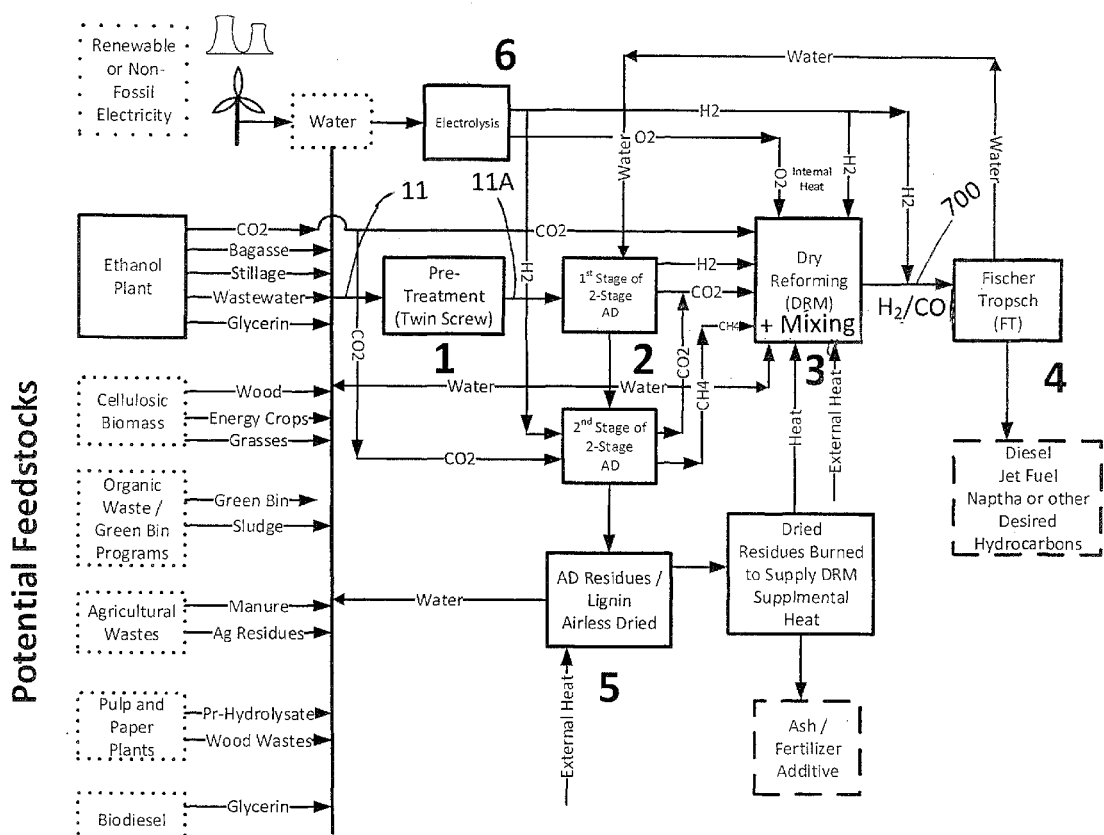
FIG. 4 schematically illustrates an overview of an exemplary integrated process in accordance with the present disclosure.
Figure 5:
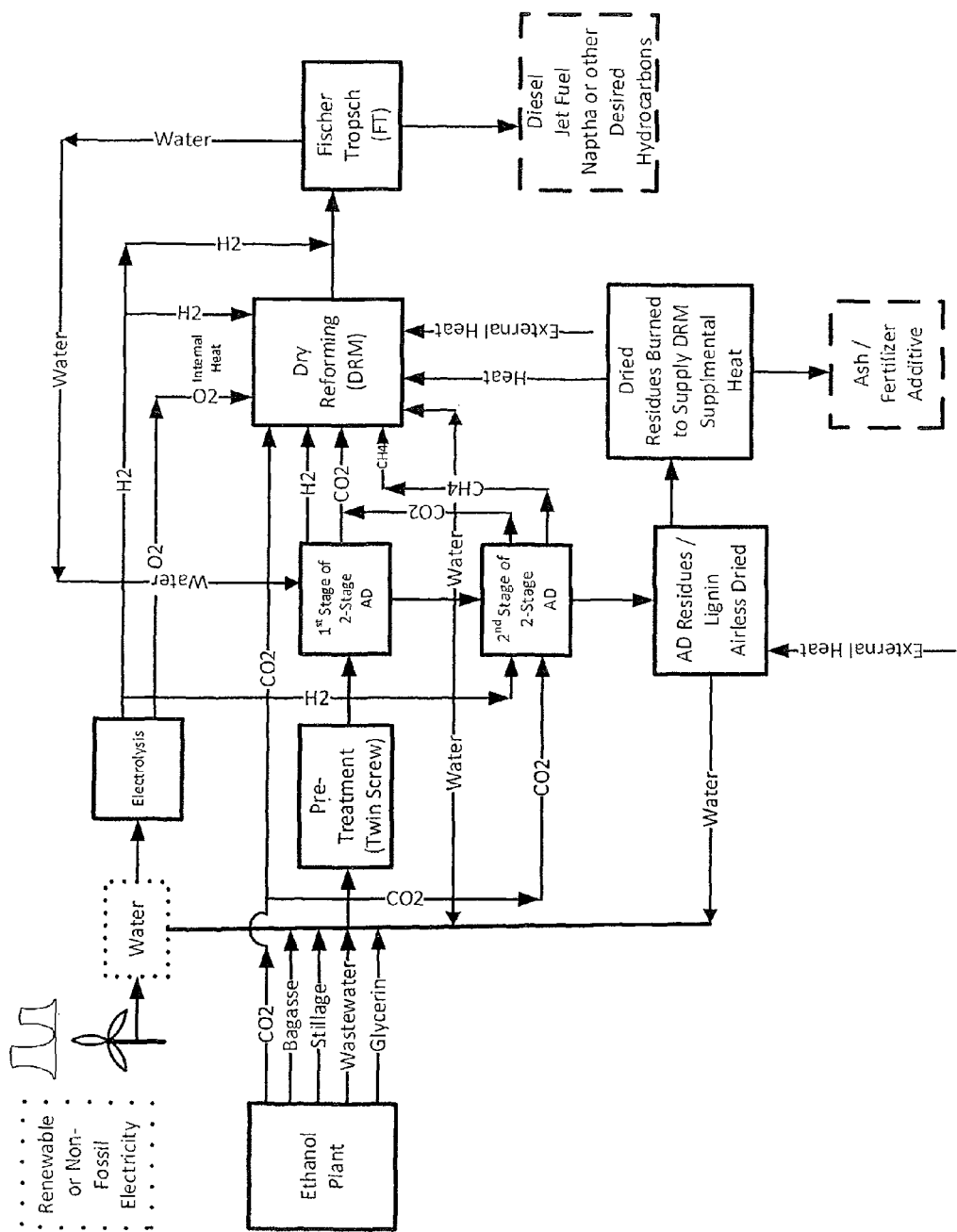
FIG. 5 illustrates an exemplary integration of the process shown in FIG. 1 with an existing ethanol plant.

The overall system of the present invention is discussed in relation to FIGS. 4 and 5 which respectively illustrate the use of the system with different types of organic material feeds. FIG. 4 schematically illustrates a system in accordance of the invention for the production of a synthetic hydrocarbon from organic material containing feedstocks. Potential feedstocks for use in a process in accordance with the invention include waste streams from a grain ethanol plant (bagasse, stillage, wastewater and glycerin), cellulosic biomass (wood, energy crops, grasses), organic wastes (green bin collection waste products; sewage sludge), agricultural wastes (agricultural plant wastes or residues, manure), pulp and paper plant waste streams (wood waste, prehydrolysate), biodiesel (glycerin) and any combinations thereof. Water may be added to adjust feedstock consistency. The feedstock preparation step is carried out in a pretreatment unit 1, preferably a twin screw extruder. Pretreated feedstock 11a is passed for the biochemical digestion step into a two stage AD system 2 including first and second stage AD reactors. As will be discussed in more detail further below, the first stage AD reactor generates the hydrogen containing biogas which is free of methane, but may contain $CO_2$ (or may even be free of $CO_2$, if $CO_2$ sequestration is used and the second stage AD reactor generates the methane containing biogas which contains $CO_2$. The methane containing biogas and the hydrogen containing biogas are passed to a dry reforming and mixing unit 3 together with the associated $CO_2$ for the production of $H_2$ and CO. AD residues and indigestible feedstock components, for example lignin, are passed to an airless spray drying unit 5 which separates the residues into water that can be recycled to the feedstock conditioning and dried residues that may be burned for the generation of supplemental heat for the dry reforming unit 3. External heat may be supplied for ensuring sufficient heat supply to the reforming unit 3. Excess $CO_2$ from an ethanol plant can be supplied to the dry reforming unit 3 and/or to the second stage AD reactor, together with $H_2$ sourced from an electrolysis unit 6 powered by non-fossil electricity, such as excess renewable electricity or nuclear electricity. Although the dry reforming unit 3 generally operates the dry methane reforming process, water may be supplied to the dry reformer unit for simultaneous operation of the wet methane reforming process as needed for the desired $H_2/CO$ mass balance of the syngas 700 produced by the dry reformer 3. Syngas 700 is passed to a Fischer Tropsch (FT) reactor 4 for conversion by Fischer Tropsch synthesis into a desired synthetic, liquid hydrocarbon. Effluent water from the FT reactor 4 may be passed as makeup water to the AD reactor 2, while cooling heat from the FT reactor 4 may be used (not shown) to preheat the input gases for the dry reformer unit 3. Pure hydrogen gas ($H_2$) and oxygen gas ($O_2$) generated in the hydrolysis unit 6 can be passed, if available, to the dry reformer unit 3, while the hydrogen gas can also be used for adjustment of the $H_2/CO$ ratio of the syngas 700.

In the exemplary embodiment illustrated in FIG. 4, the organic material feedstock stream is derived exclusively from a grain ethanol plant, while the system components and their operation and interaction are the same as in the system shown in FIG. 4 and discussed immediately above.

Figure 6:
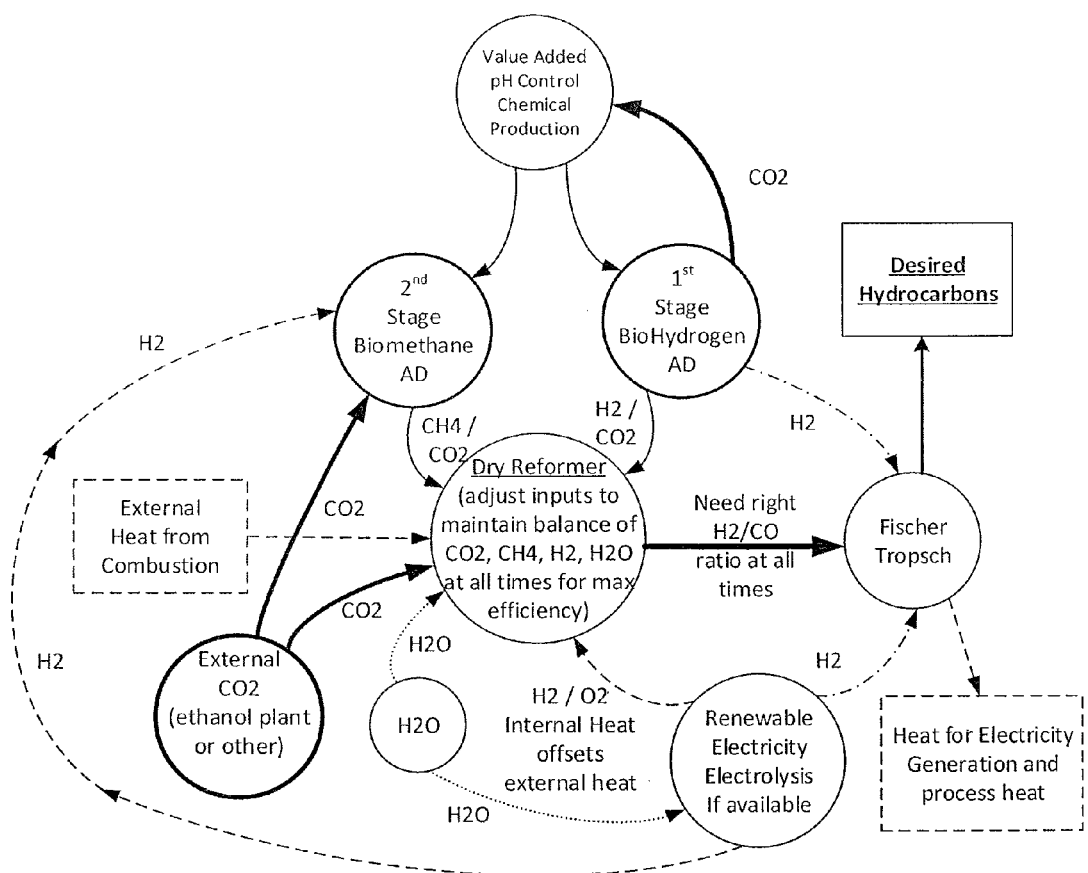
FIG. 6 illustrates the relationship of the different input streams into the first and second reforming steps.
Figure 7A:
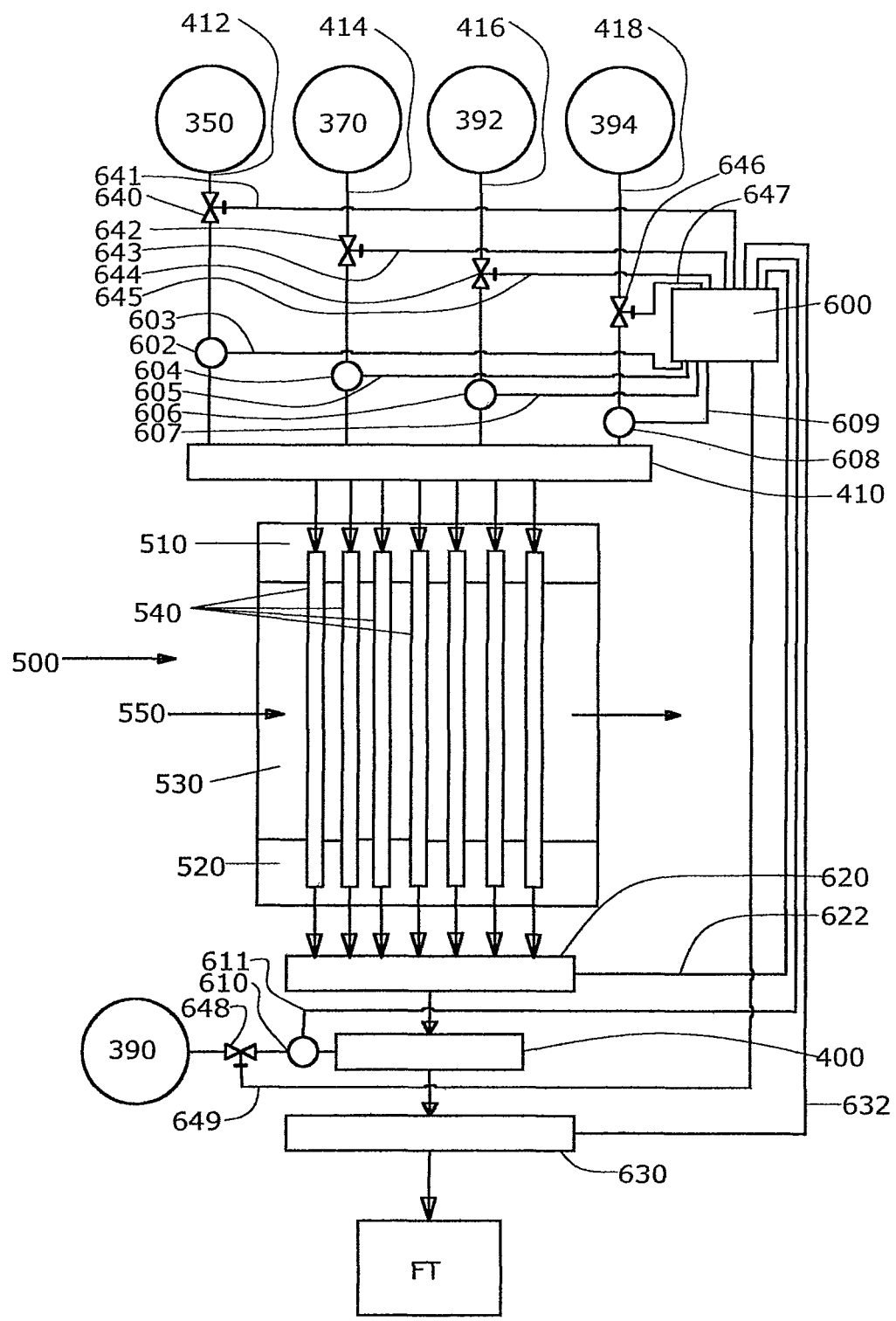
FIG. 7A schematically illustrates in more detail the flexible DRM process.
Figure 7B:
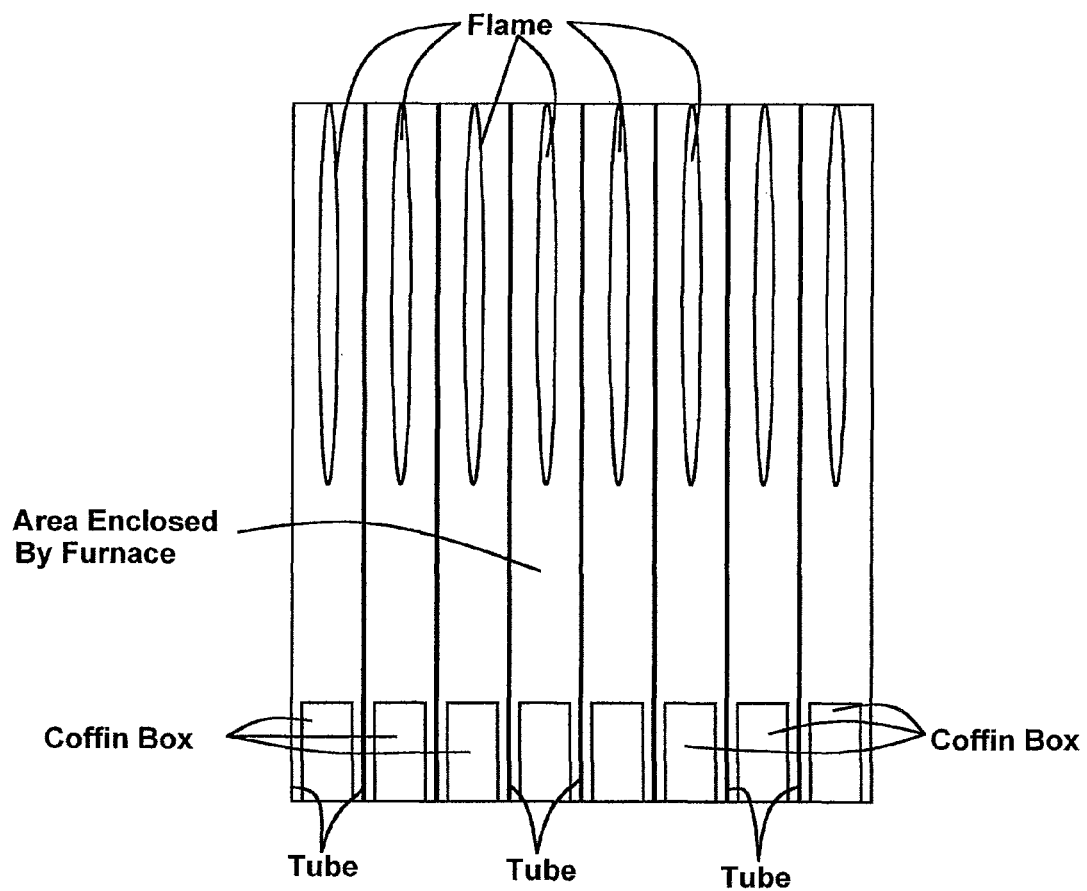
FIG. 7B is a schematic front view of a steam-methane reforming furnace for carrying out the flexible DRM process of FIG. 7A.
Figure 7C:
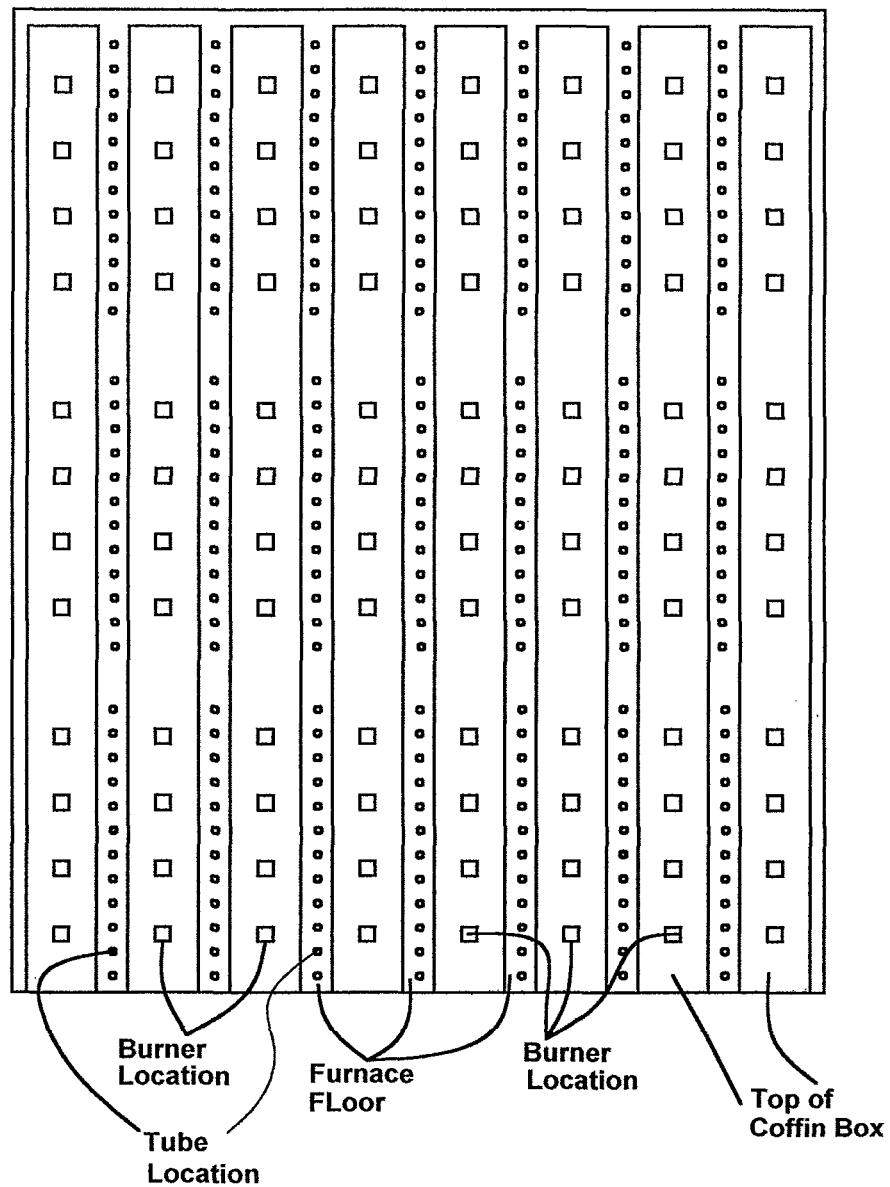
FIG. 7C is a schematic top view of the steam-methane reforming furnace of FIG. 7B.

The individual process streams into the dry reformer unit 3 within a process and system in accordance with the invention and their relationship to each other is schematically illustrated in FIG. 6. The flow of heat into and within the system is also illustrated in FIG. 6.

Biomass Pretreatment

Cellulosic biomass is preferably pretreated to free up the digestible components of the biomass for faster biochemical degradation/anaerobic digestion (AD). This entails at a a particle size reduction of the organic material to be subjected to AD, which size reduction is preferably achieved in an extruder, most preferably a twin screw extruder, since the shear forces and pressure variations in the space between the extruder screw and the barrel, or between the extruder screws themselves are advantageous not only for particle size reduction, but also for cell lysis. A particle size after the extruder of at least 3 to 4 mm in one dimension is preferable.

Cellulosic biomass includes hemicellulose, which is a heteropolymer or matrix polysaccharide present in almost all plant cell walls along with cellulose. While cellulose is crystalline, strong, and resistant to hydrolysis, hemicellulose has a random, amorphous structure with little strength. Hydrolysis of hemicellulose can be relatively easily achieved with acids or enzymes. Hemicellulose contains many different sugar monomers. For instance, besides glucose, hemicellulose can include xylose, mannose, galactose, rhamnose, and arabinose. Xylose is the monomer present in the largest amount. While cellulose is highly desirable as a starting material for enzymatic ethanol production, hemicellulose and its hydrolytic degradation products interfere with the enzymatic hydrolysis of cellulose and the downstream fermentation of glucose from cellulose. Xylose derivatives and degradation products, and acetic acid, (all of which are products of hemicellulose hydrolysis), are inhibitors of glucose fermentation to ethanol using yeast. Fortunately, those degradation products do not affect bacterial decomposition in an anaerobic digestion (AD) unit and can actually be decomposed as well, given the right mixture of bacteria in the decomposition broth. Thus, contrary to the need for very specialized pretreatment protocols to minimize inhibitor generation for enzymatic hydrolysis and "clean sugars" generation in fermentation based biofuel production processes, a much less involved pretreatment is acceptable for an anaerobic digestion based biofuel production process.

The present inventors have found that pretreatment of biomass upstream of AD can be limited almost completely to maximizing the breakdown of any large, polymeric or complex hydrocarbons or hydrocarbon compositions, since any breakdown products produced are most likely digestible by anaerobic bacterial digestion in the AD step. Thus, the biomass is preferably exposed in the pretreatment step to liquid hot water treatment or steam explosion treatment at elevated temperatures and pressures. After a preselected exposure time adjusted to the respective biomass treated, the pretreated biomass is fed directly to the AD process, after appropriate temperature and solids content adjustments as required according to the AD conditions respectively used. If steam pretreatment is used, the pressure is preferably quickly released to achieve explosive decomposition of the biomass into fibrous solids and condensate, both of which are then combined into an organic matter feed stream for the downstream AD process.

The exposing step can be carried out at low severity (low degradation) conditions in which hemicellulose in the biomass is liquefied, but the liquefied hemicellulose and any cellulose in the biomass are not degraded or to only a minor degree (SI of 3.3 to 3.7). In the alternative, the exposing step can be carried out at high severity (high degradation) conditions in which hemicellulose is liquefied and the liquefied hemicellulose and the cellulose are all partially degraded, albeit to varying degrees, irrespective of the potentially negative effect some degradation products may have on a subsequent biochemical digestion (SI of 3.8 to 4.7). Exemplary low degradation conditions are a temperature of 150 to 250° C. a pressure of 50 psig to 560 psig and a preselected pretreatment time of 5 to 15 minutes. Standard steam used in many steam operated process and having a pressure of 150 psig can be advantageously used for the low severity treatment in situations where the system of the invention is integrated with an ethanol production or pulp and paper facility which generally already produce standard steam. Under some circumstances much carbon may be needed to supply heat for the process and exemplary high degradation conditions could be used at temperatures of 250 to 300° C., and pressures of 300 psig to 1,200 psig and a preselected pretreatment time of up to 10 minutes. Preferred, high degradation conditions for the exposing step are a temperature of 230 to 270° C., most preferably 250° C., a pressure of 500 psig to 700 psig, most preferably 600 psig and a treatment time of 1 to 5 minutes, most preferably 1 minute. Regardless whether high or low degradation conditions are used, the pressure is preferably released within less than 1000 milliseconds (ms), preferably within 600 ms, most preferably within 300 ms.

Figure 1B:
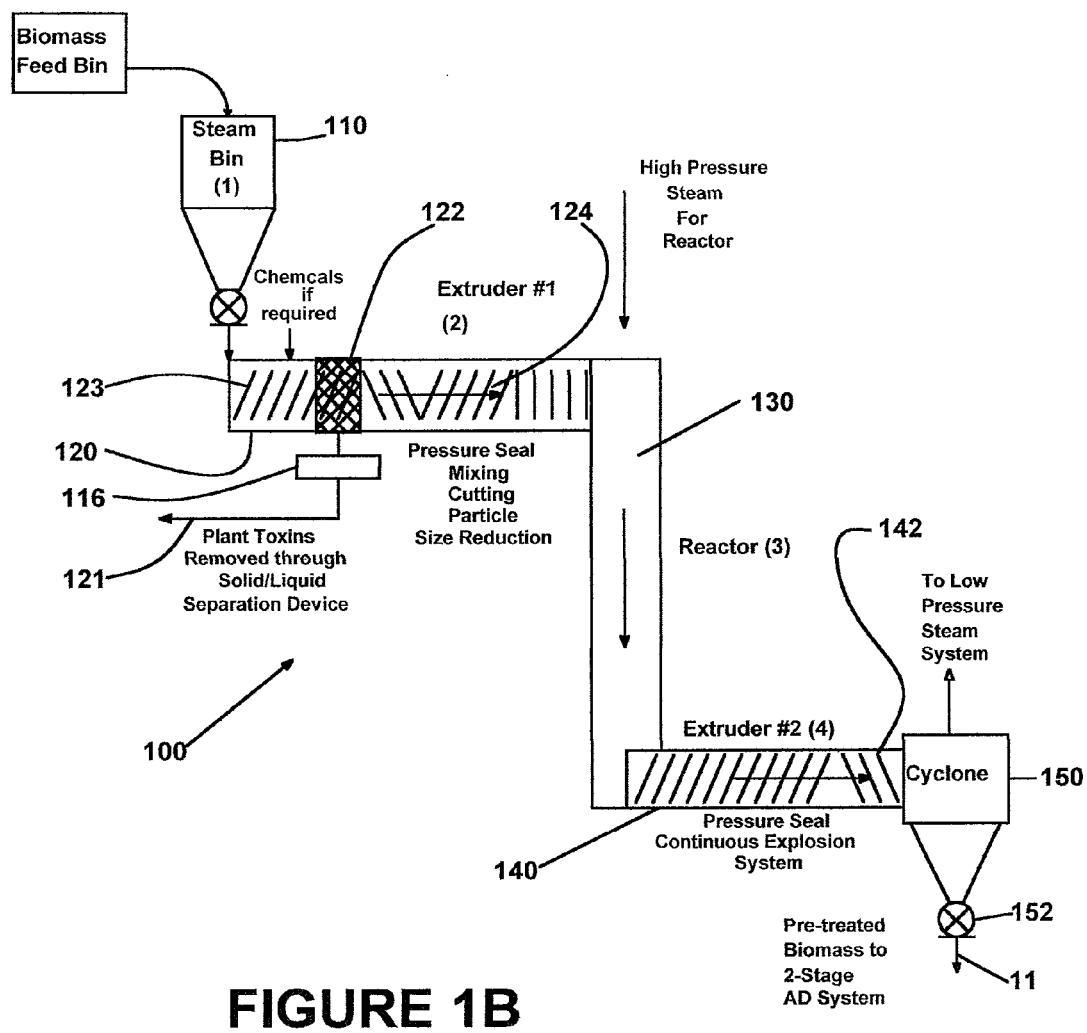
FIG. 1B schematically illustrates a two stage pretreatment process and equipment for the pretreatment of biomass to generate feedstock for the biochemical digestion step of the present process.
Figure 1C:
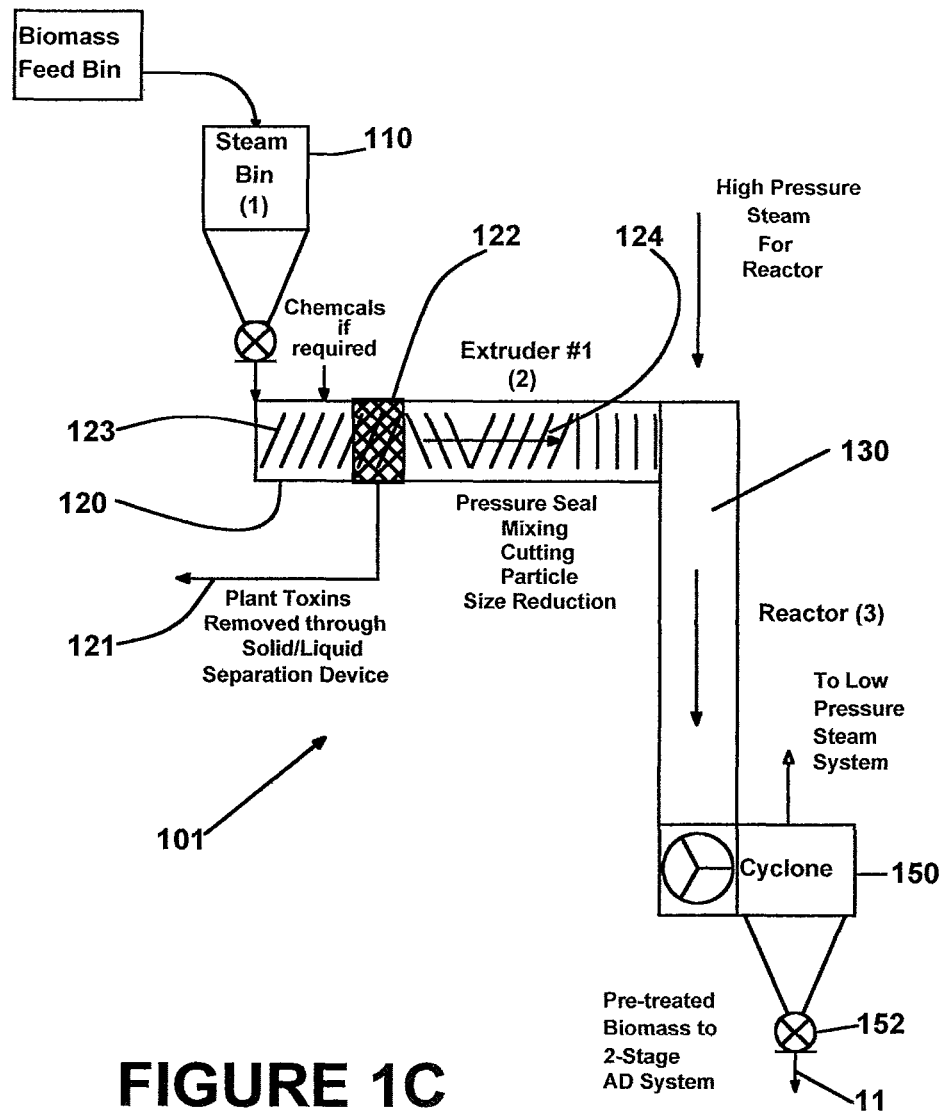
FIG. 1C schematically illustrates a first single stage pretreatment process and equipment for the pretreatment of biomass to generate feedstock for the biochemical digestion step of the present process.
Figure 1D:
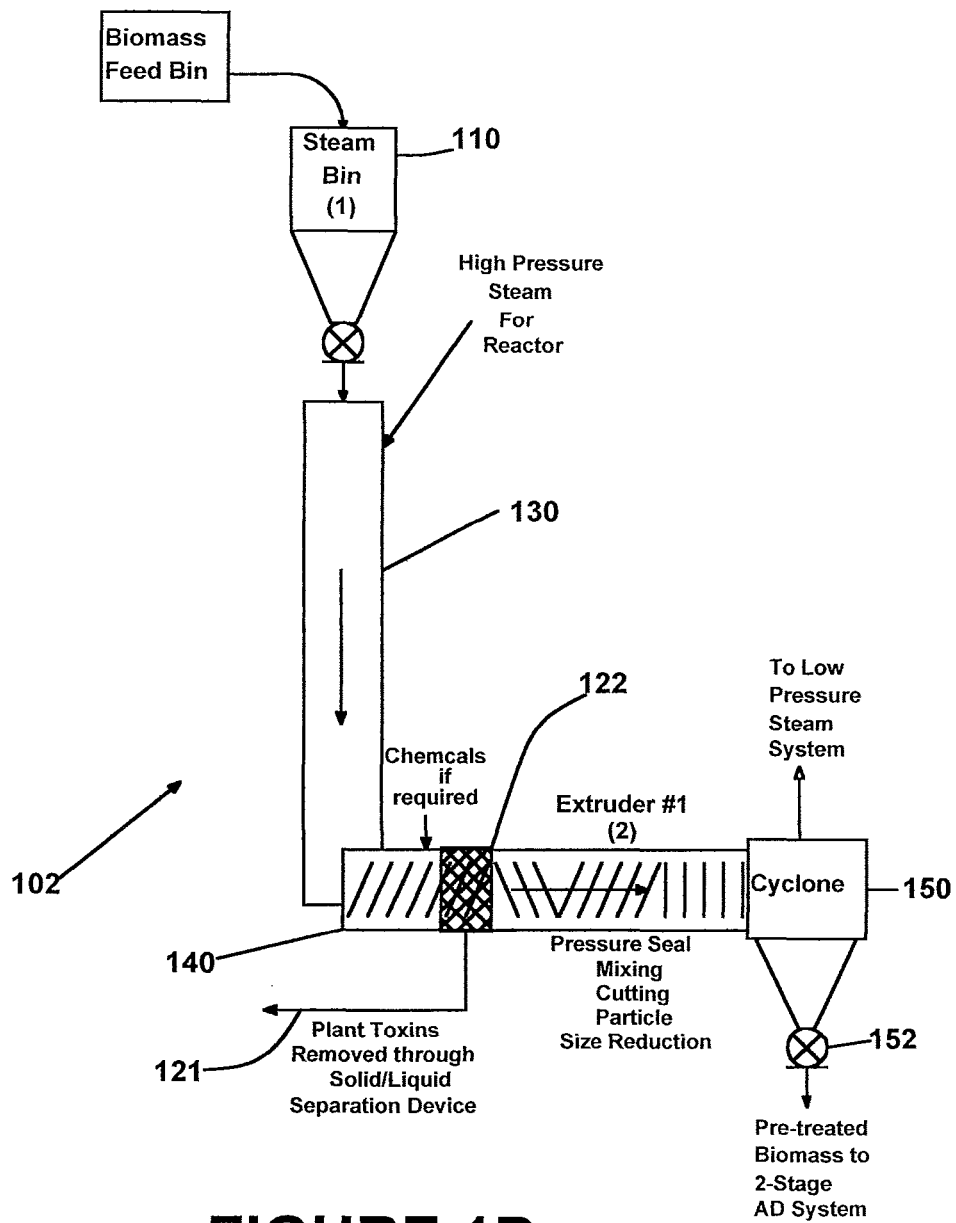
FIG. 1D schematically illustrates a second single stage pretreatment process and equipment for the pretreatment of biomass to generate feedstock for the biochemical digestion step of the present process.
Figure 1E:
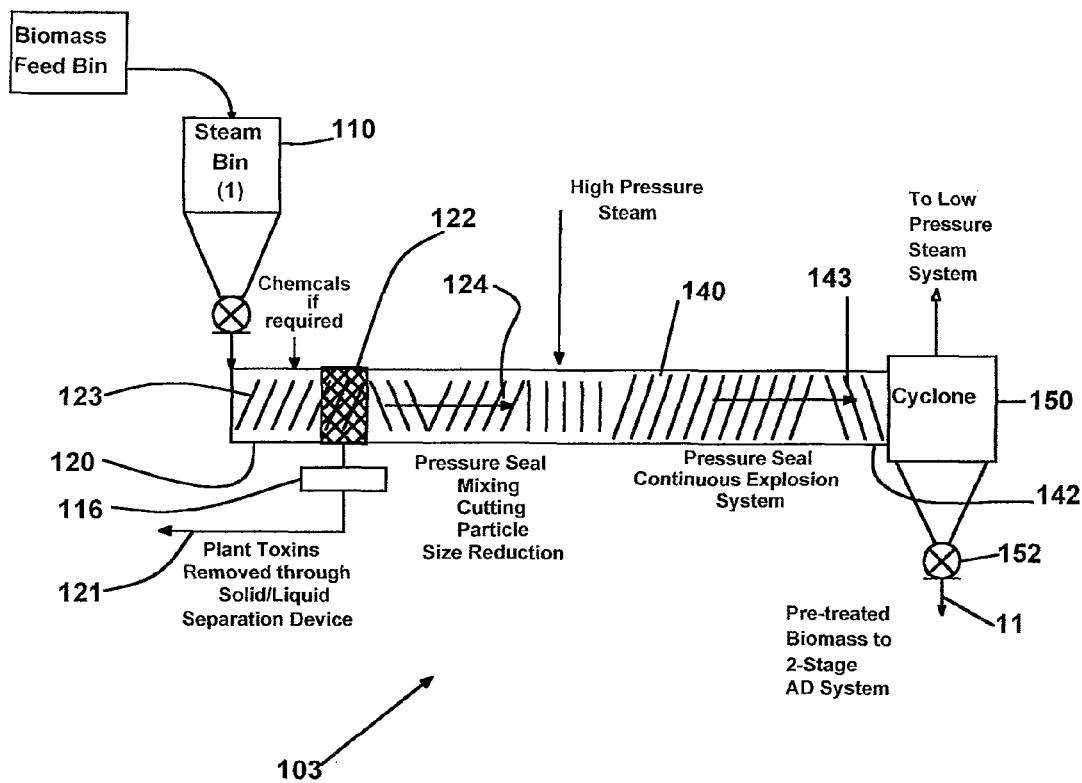
FIG. 1E schematically illustrates a third single stage pretreatment process and equipment for the pretreatment of biomass to generate feedstock for the biochemical digestion step of the present process.
Figure 1F:
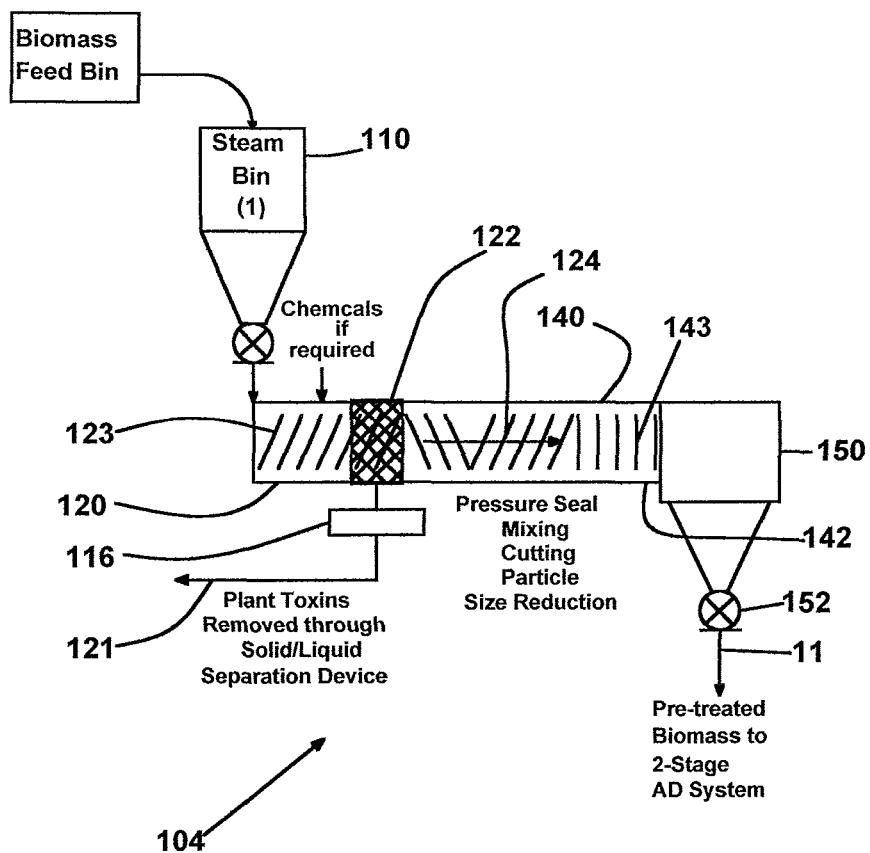
FIG. 1F schematically illustrates the most basic single stage pretreatment process and equipment for the pretreatment of biomass to generate feedstock for the biochemical digestion step of the present process.

In the most basic exemplary pretreatment system 104, a twin screw extruder 120 is used for particle size reduction and cell lysis as shown in FIG. 1F. The illustrated system 104 is used for operating a single step pretreatment process and can consist of only two basic components, an atmospheric steaming bin 110 and the extruder 120 with an optional solid/fluid separation device 122 for the separation of a stream of plant toxins 121. An exemplary device for carrying out this pretreatment is a twin screw extruder with or without an adjustable backpressure section, as described in US2015/0224428, the disclosure of which is incorporated herein in its entirety (available from Greenfield Specialty Alcohols (Ontario)). The treatment pressure can be adjusted by controlling the rotation speed of the extruder screws, by changing the conveyor screw configuration, by adjusting a clearance between the extruder barrel and the extruder screws in a backpressure section, or by creating a flow restriction downstream of the conveyor screws, which flow restriction generates a movable plug of treated material that in turn creates backpressure in the extruder barrel. Such a flow restriction can be a pipe having a restriction or sufficient length to create a sufficient flow restriction for backpressure build-up.

In a second exemplary continuous cellulosic ethanol pre-treatment system 100 for use in a hydrocarbon synthesis process in accordance with the present disclosure as shown in FIG. 1B a step with explosive decompression is added to provide a dual step pretreatment. The illustrated system 100, is used for operating a two-step pretreatment process and can consist of only four basic components, an atmospheric steaming bin 110, a $1^{st}$ extruder 120 with plant toxin/resin removal, pressure seal and particle size reduction capability, a reactor 130 which cooks the biomass with steam at high pressure, and a $2^{nd}$ extruder 140 which seals the reactor pressure while continuously discharging pre-treated biomass in an explosive manner into a cyclone separator 150 which operates at lower pressure and feeds this lower pressure back into the process for low grade heating needs with a rotary valve 152 which discharges the pre-treated biomass into the AD system. The plant toxin removal is achieved with a solid/fluid separation device 122. The feed into the solid/liquid separation device 122 and pressure seal and particle size reduction are achieved with different conveyor screw components 123, 124 in the first extruder 120. Liquid pressure and flashing can be controlled by the use of a pressure controlled flash tank 116 downstream of the solid/fluid separation device 122.

Figure 10:
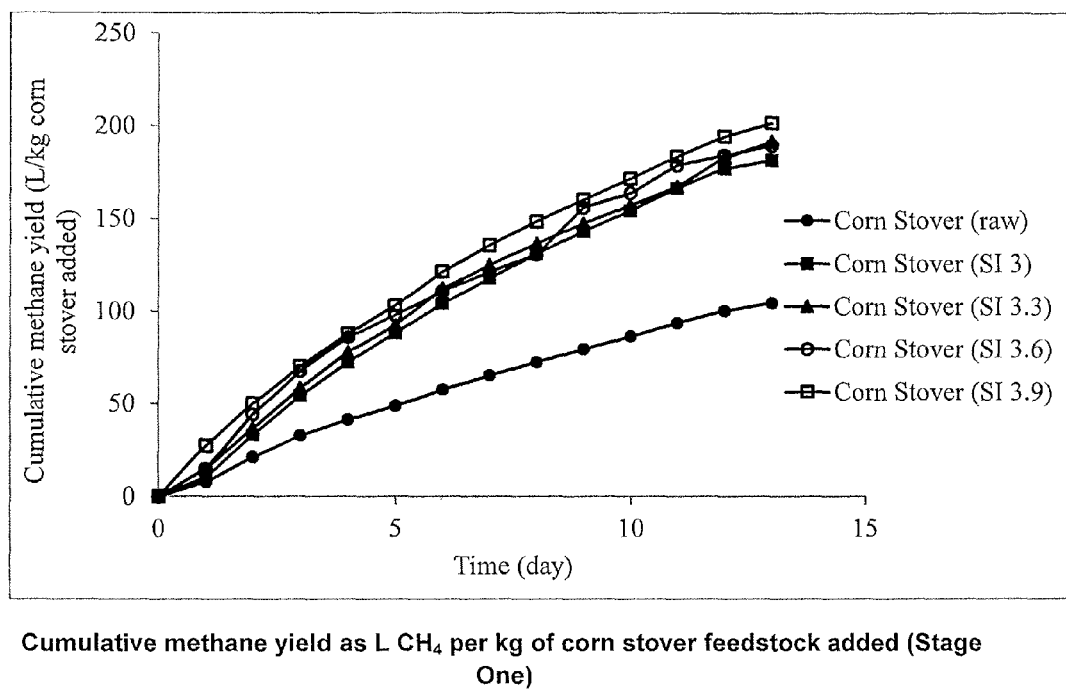
FIG. 10 illustrates cumulative methane yields obtained at Stage One pretreatment conditions for Corn Stover feedstock.

In a third, more simplified pretreatment system 101, used for the operation of a single stage pretreatment process and illustrated in FIG. 10, the second extruder can be omitted and the reactor 130 equipped with a pressure gate which allows for the controlled release of pre-treated biomass under explosive decompression, for example a rotary gate 132. The other components of flash tank 116, cyclone 150 and rotary valve 152 are the same as in the dual stage system 100.

In a fourth, even further simplified single stage system 102 used for the operation of a single stage pretreatment and illustrated in FIG. 1D, the reactor 130 is placed between the steaming bin 110 and the first extruder 120, while the second extruder is omitted. In this single stage system 102, the pre-treated biomass is continuously released from the first extruder in an explosive manner, similar to the biomass release from the second extruder 140 in the dual stage system 100. The other components of flash tank 116, cyclone 150 and rotary valve 152 are the same as in the dual stage system 100.

In a fifth, additionally simplified single stage system 103 used for the operation of a single stage pretreatment and illustrated in FIG. 1E, the reactor 130 is eliminated and the cooking of the biomass occurs within a combined extruder 141 that effectively is a combination of the first and second extruders 120, 140 of the dual stage system 100. In the combined extruder 141, cooking of the biomass occurs after toxins have been removed from the biomass in the solid/fluid separation device 122, if necessary. The solid/fluid separation device can be a twin screw extruder filter (TSE). Cooking in the combined extruder 141 necessarily has to occur at relatively high steam pressures from 600 to 1,000 psi for 60 seconds at 600 psi and down to 20 seconds at the higher pressure of 1000 psi. Discharge from the TSE can be accomplished using a reversing element 143 at the end 142 of the extruder 141 such that individual particles of the biomass decompressively explode in less than 300 ms continuously out the extruder and into the cyclone 150 where flashed steam can be recycled for use as a biomass pre-heat source.

In the dual stage process operated in the dual stage pretreatment system 100, the biomass is preferably chopped or ground prior to the exposure step, most preferably upstream of the steaming bin 110, in order to reduce the required treatment time. Standard size wood chips can be used, if the first extruder 120 is used for particle size reduction. The first extruder 120 is used as a continuous high pressure plug feeder/mixer/grinder for the steamed biomass. The extruder 120 feeds the biomass into the vertical reactor 130. The vertical reactor 130 feeds the biomass into the second extruder 140, preferably a twin screw extruder, more preferably a twin screw extruder with a backpressure section 142 with explosive decompression, from which individual particles of the leftover pre-treated biomass solids expand rapidly.

In the dual stage system 100, various treatment chemicals can be admixed with the biomass in the first extruder 120, depending on the type of feedstock. For example, mineral acids or bases (f. ex. ammonia), can be added for improving biomass hydrolysis and/or solvents can be used for removal of unwanted biomass components, such as lignin. The biomass exiting the steaming bin 110 enters the first extruder 120, as shown in FIG. 1B, and is therein subjected to a zone of higher pressure. Liquid biomass extractives 121 that are toxic to digestion are squeezed out using a solid/fluid separation device 122 in the first extruder 120, preferably a solid/fluid separator unit for an extruder as described in U.S. Pat. No. 8,746,138, PCT Application WO2015/077885, or US Patent Applications US2013-0264264-A1 and US2015/0336031, which are all incorporated herein by reference in their entirety. In the solid/fluid separation device 122, extractives are removed and the cake thickness controlled by the use of various screw elements 123, 124. Permeability, pore size, filter area and pressure rating can be controlled according on the biomass type treated If no extractive removal is desired as the particular biomass feedstock does not include substances toxic to the anaerobic microorganisms used in biochemical digestion step 20, then the extraction step and solid/liquid separation device 122 can be omitted.

The Vertical Reactor 130 is preferably capable of operating with various chemicals at pressures of up to 750 psig and temperatures of up to 267° C., depending on the biomass treated. Residence time in the vertical reactor 130 can be varied from 0.5 minutes to 10 minutes, depending on the biomass treated.

Upon explosive decompression and expansion of the biomass at the output 142 of the $2^{nd}$ extruder 140, the cyclone separator 150, or another separating device is used to collect both the solids and any gases, which are ejected, if desired.

The condensate and solids generated during cooking and at pressure release can be separately captured and processed, but are preferably combined into the feedstock 11 for the downstream biochemical digestion step 20, preferably a two stage AD. The solids stream expelled from the second extruder 140 upon explosive decompression, which is also referred to as prehydrolysate, can be separated from the gaseous reaction products and steam in the cyclone separator 150. The solids collected at the bottom of the separator are preferably transported to the downstream AD process through a rotary valve 152 or other continuous pressure sealing device depending on the operating gas pressure of the cyclone separator 150, which can vary from 0 psig to 15 psig.

At the exit end 142 of the second extruder 140, a dynamic pressure seal is provided to prevent leakage from the vertical reactor 130. The pressure seal can be created by utilizing reverse conveying elements at the end of the extruder conveying screws. The pressure seal is used to ensure that explosive decompression occurs at the exit end 142 of the extruder 140, which completes the pretreatment of the solids and is intended to assist in speeding up digestion by physical defiberization of the pretreated biomass. In the second extruder 140 shown on FIG. 1, the biomass can also be subjected to high pressure mixing/chopping with variable shear/cutting energy for various biomasses to further improve the pre-treatment. The shear/cutting energy is generally varied by adjustment of the rotation speed, or by modifying the configuration of the conveying screws.

Pretreatment Examples

Three different types of exemplary pretreatments were used, 1) particle size reduction through extrusion in a twin screw extruder (TSE; GFSA Inc., Ontario), 2) TSE followed by low severity hydrothermal (HT) pretreatment (Stage One), and 3) TSE followed by Stage One and HT pretreatment at high severity (Stage Two). The exemplary treatment conditions used in Stage One and Stage Two are shown in Table 4 below.

TABLE 4

Pretreatment conditions for Stage One and Stage Two for different feedstocks

| | Feedstock | Temperature (oC) | Pressure (psig) | Reaction time (min:sec) | SI |
|---|---|---|---|---|---|
| Stage One | Poplar | 147.5 | 50 | 40 | 3 |
| | | 147.5 | 50 | 80 | 3.3 |
| | | 147.5 | 50 | 160 | 3.6 |
| | | 147.5 | 50 | 320 | 3.9 |
| | Corn Stover | 147.5 | 50 | 40 | 3 |
| | | 147.5 | 50 | 80 | 3.3 |
| | | 147.5 | 50 | 160 | 3.6 |
| | | 147.5 | 50 | 320 | 3.9 |
| | Soft wood | 147.5 | 50 | 40 | 3 |
| | | 147.5 | 50 | 80 | 3.3 |
| | | 147.5 | 50 | 160 | 3.6 |
| | | 147.5 | 50 | 320 | 3.9 |
| Stage Two | Poplar | 208 | 250 | 0:40 | 3 |
| | | 208 | 250 | 2:07 | 3.5 |
| | | 208 | 250 | 4:14 | 3.8 |
| | | 208 | 250 | 6:42 | 4 |
| | | 208 | 250 | 10:37 | 4.2 |
| | | 208 | 250 | 21:12 | 4.5 |
| | Corn Stover | 208 | 250 | 0:40 | 3 |
| | | 208 | 250 | 2:07 | 3.5 |
| | | 208 | 250 | 4:14 | 3.8 |
| | | 208 | 250 | 6:42 | 4 |
| | | 208 | 250 | 10:37 | 4.2 |
| | | 208 | 250 | 21:12 | 4.5 |

Pretreated samples were subjected to two stage anaerobic digestion in a mesophilic digester, as will be discussed further below. Standard biohydrogen potential (BHP) and biomethane potential (BMP) tests were used to evaluate the digestibility of poplar wood, corn stover, and soft wood. To assess the significance of the use of extrusion and single stage or dual stage HT pretreatment on both hydrogen and methane productivity, BHP and BMP tests were undertaken for the three different pretreatment types of 1) extrusion of biomass samples in TSE, 2) extrusion of biomass samples in TSE followed by single stage HT in a Parr reactor (Stage One, see Table 4), and 3) extrusion of biomass samples in TSE followed by dual stage HT (Stage One and Stage Two, see Table 4). Table 5 below compares average hydrogen and methane yields from samples of poplar wood pretreated with TSE, TSE+single stage HT and TSE+dual stage HT respectively.

TABLE 5

Poplar Wood Yields

| Pretreatment | Hydrogen Yield | Methane Yield |
| --- | --- | --- |
| TSE (Raw) | 1.1 $LH_2$/Kg biomass | 71 $LCH_4$/Kg biomass |
| TSE + Stage one | 2.5 $LH_2$/Kg biomass | 221 $LCH_4$/Kg biomass |
| TSE + Stage One + Stage Two | 14.2 $LH_2$/Kg biomass | 295 $LCH_4$/Kg biomass |

It is readily apparent from Table 5 that, at least for Poplar Wood, dual stage HT provides for yields which are a multiple of those achieved with single stage HT, while single stage HT already multiplies the yields achievable with biomass extrusion only.

BMP after First Stage Pretreatment

The effect of single stage pretreatment on biomass samples of poplar wood, corn stover and soft wood, was tested by measuring the BMP through mesophilic digestion of raw samples (TSE) and samples subjected to single stage pretreatment (TSE+Stage One; see Table 4). The following results were observed:

TABLE 6

Methane Yields in $LCH_4$/kg substrate

| Biomass | Raw | Single Stage | % increase |
| --- | --- | --- | --- |
| Poplar | 71 | 179 | 133 |
| Corn Stover | 105 | 202 | 93 |
| Soft Wood | 65 | 138 | 112 |

BHP after First Stage Pretreatment

The effect of single stage pretreatment on biomass samples of poplar wood, corn stover and soft wood, was tested by measuring the BHP through mesophilic digestion of raw samples (TSE) and samples subjected to single stage pretreatment (TSE+Stage One; see Table 4). The following results were observed:

TABLE 7

Hydrogen Yields in $LH_2$/kg substrate

| Biomass | Raw | Single Stage | % increase |
| --- | --- | --- | --- |
| Poplar | 1.1 | 2.5 | 125 |
| Corn Stover | 1 | 2.4 | 121 |
| Soft Wood | 0.6 | 1.2 | 95 |

BMP after Second Stage Pretreatment

The effect of dual stage pretreatment on the BMP of poplar wood and corn stover samples was tested through mesophilic digestion of raw samples (TSE) and samples subjected to second stage pretreatment (TSE+Stage Two; see Table 4). The following results were observed:

TABLE 8

Methane Yields in $LCH_4$/kg substrate

| Biomass | Raw | Dual Stage | % increase |
| --- | --- | --- | --- |
| Poplar | 71 | 237 | 234 |
| Corn Stover | 105 | 226 | 116 |

BHP after Second Stage Pretreatment

The effect of dual stage pretreatment on the BHP of poplar wood and corn stover samples was tested through mesophilic digestion of raw samples (TSE) and samples subjected to second stage pretreatment (TSE+Stage Two; see Table 4). The following results were observed:

TABLE 9

Hydrogen Yields in $LH_2$/kg substrate

| Biomass | Raw | Dual Stage | % increase |
| --- | --- | --- | --- |
| Poplar | 1.1 | 2.6 | 137 |
| Corn Stover | 1 | 2.6 | 161 |

BMP after Dual Stage Pretreatment

Standard BMP tests were carried out on poplar wood and corn stover samples pretreated with dual stage HT at the conditions set out in Table 4 (TSE+Stage One+Stage Two). The C5 liquids stream (second stage extract), the C6 solids stream (exploded solids of second stage), and a 50/50 mixture of the C5 and C6 streams were tested separately. The following results were obtained:

TABLE 10

Methane Yields in $LCH_4$/gCOD$_{added}$

| Sample Type | Maximum | Minimum | Average |
| --- | --- | --- | --- |
| C5 | 0.199 | 0.124 | 0.163 |
| C6 | 0.179 | 0.119 | 0.139 |
| 50/50 C5/C6 | 0.192 | 0.117 | 0.147 |

TABLE 11

Methane Yields in $LCH_4$/gCOD$_{consumed}$

| Sample Type | Maximum | Minimum | Average |
| --- | --- | --- | --- |
| C5 | 0.467 | 0.337 | 0.393 |
| C6 | 0.398 | 0.274 | 0.362 |
| 50/50 C5/C6 | 0.415 | 0.279 | 0.355 |

TABLE 12

Methane Yields in $LCH_4$/kg substrate

| Sample Type | Maximum | Minimum | Average |
| --- | --- | --- | --- |
| C5 | 30.7 | 7.1 | 16 |
| C6 | 212 | 176 | 185 |
| 50/50 C5/C6 | 52 | 36 | 44 |

BHP after Dual Stage Pretreatment

Standard BHP tests were carried out on poplar wood and corn stover samples pretreated with dual stage HT at the conditions set out in Table 4 (TSE+Stage One+Stage Two). The C5 liquids stream (second stage extract), the C6 solids stream (exploded solids of second stage), and a 50/50 mixture of the C5 and C6 streams were tested separately. The following results were obtained:

TABLE 13

Hydrogen Yields in LH₂/gCOD added

| Sample Type | Maximum | Minimum | Average |
|---|---|---|---|
| C5 | 0.103 | 0.053 | 0.075 |
| C6 | 0.016 | 0.002 | 0.008 |
| 50/50 C5/C6 | 0.031 | 0.012 | 0.018 |

TABLE 14

Hydrogen Yields in LH₂/gCOD consumed

| Sample Type | Maximum | Minimum | Average |
|---|---|---|---|
| C5 | 0.441 | 0.103 | 0.310 |
| C6 | 0.046 | 0.007 | 0.028 |
| 50/50 C5/C6 | 0.244 | 0.027 | 0.125 |

TABLE 15

Hydrogen Yields in LH₂/kg substrate

| Sample Type | Maximum | Minimum | Average |
|---|---|---|---|
| C5 | 13.1 | 2.3 | 7.1 |
| C6 | 14.2 | 3.2 | 7.6 |
| 50/50 C5/C6 | 10.5 | 2.8 | 5.1 |

As is apparent from the results in Tables 6-9, both single stage pretreatment and dual stage pretreatment significantly increased the BHP and BMP of biomass samples tested, whereby the BHP and BMP of samples subjected to dual stage HT was again significantly higher than that of samples subjected to either first stage HT or second stage HT (Tables 10-15). Thus, although acceptable BHP and BMP are observed after TSE pretreatment, improved results should be obtained with either first stage HT or second stage HT and the most advantageous results should be achieved with dual stage HT. Although some COD is expected to be lost during Stage One and Stage Two pretreatment, its effect is considered minimal in view of the high increase in BHP and BMP with both Stage One and Stage Two HT.

Figure 9:
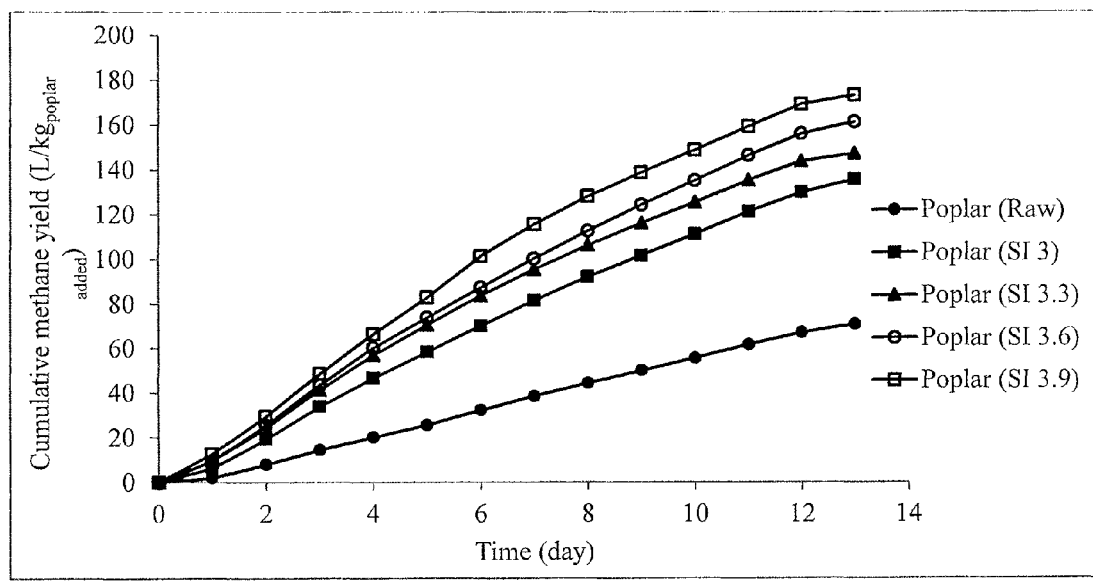
FIG. 9 illustrates cumulative methane yields obtained at Stage One pretreatment conditions for Poplar feedstock.
Figure 11:
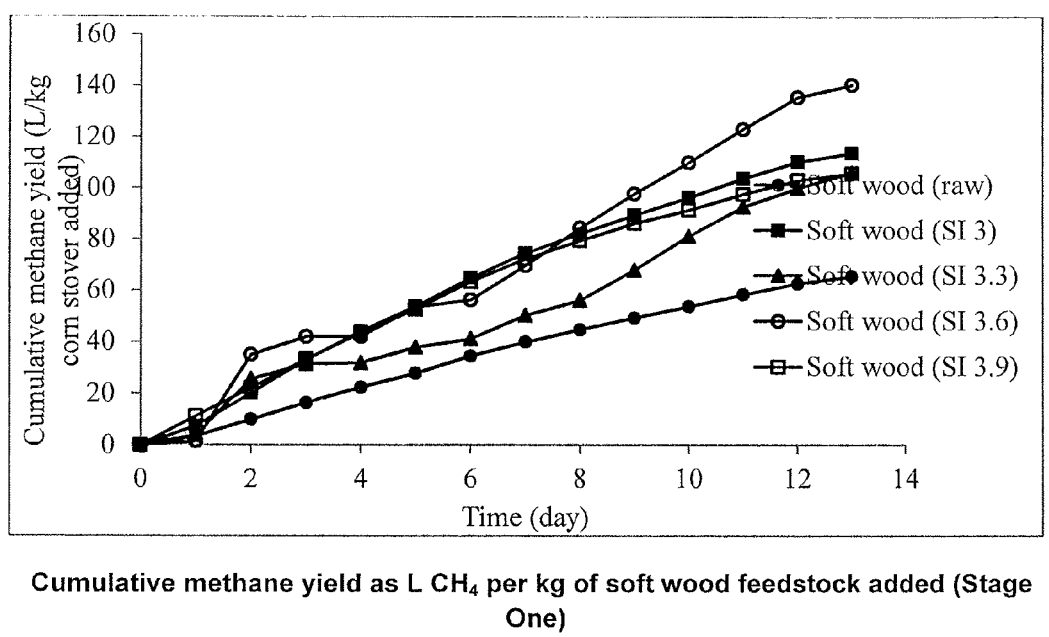
FIG. 11 illustrates cumulative methane yields obtained at Stage One pretreatment conditions for Soft Wood feedstock.
Figure 12:
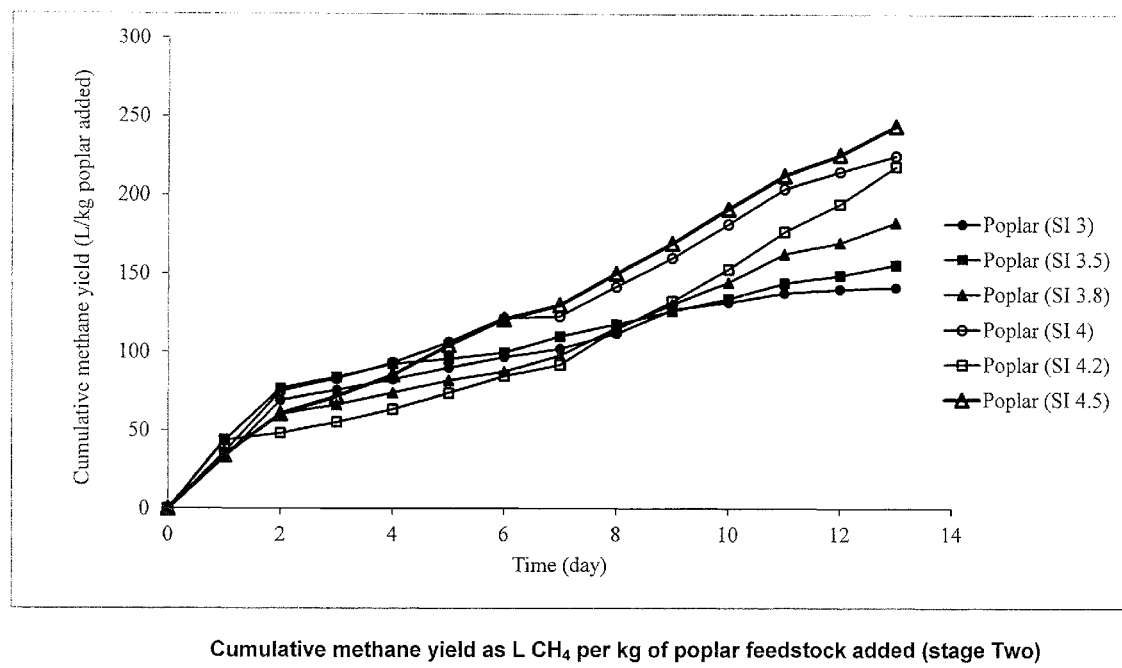
FIG. 12 illustrates cumulative methane yields obtained at Stage Two pretreatment conditions for Poplar feedstock.
Figure 13:
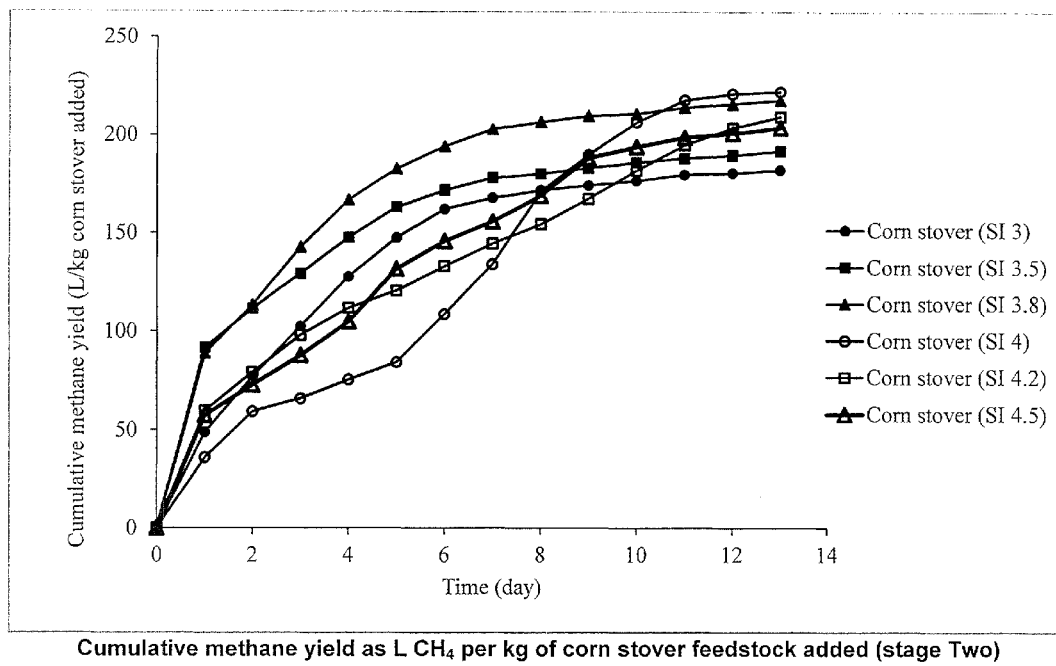
FIG. 13 illustrates cumulative methane yields obtained at Stage Two pretreatment conditions for Corn Stover feedstock.
Figure 14:
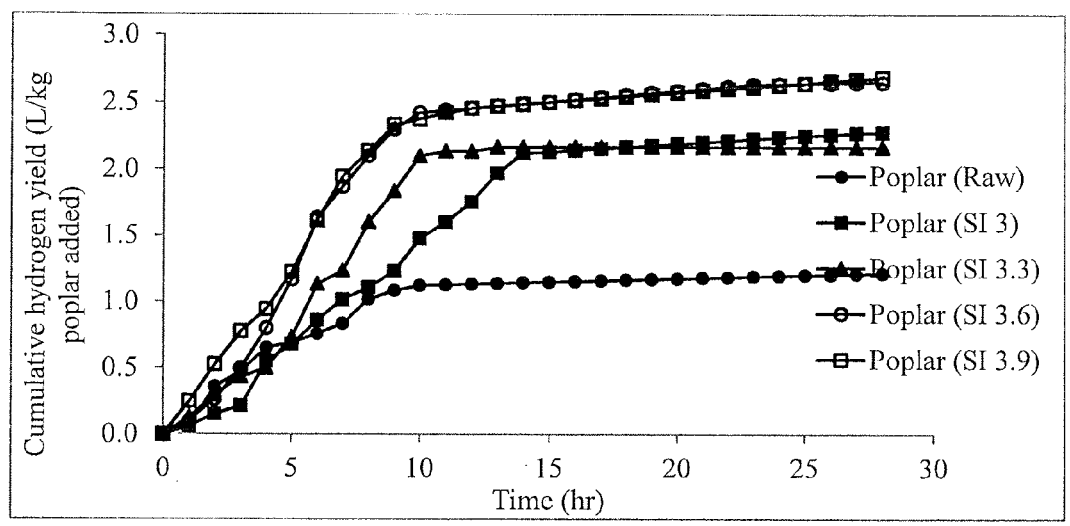
FIG. 14 illustrates cumulative hydrogen yields obtained at Stage One pretreatment conditions for Poplar feedstock.
Figure 15:
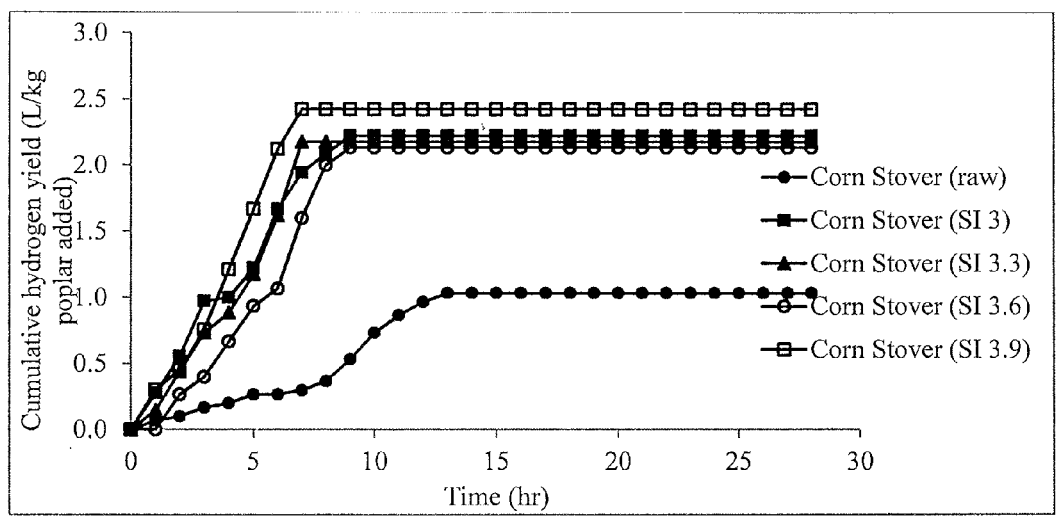
FIG. 15 illustrates cumulative hydrogen yields obtained at Stage One pretreatment conditions for Corn Stover feedstock.
Figure 16:
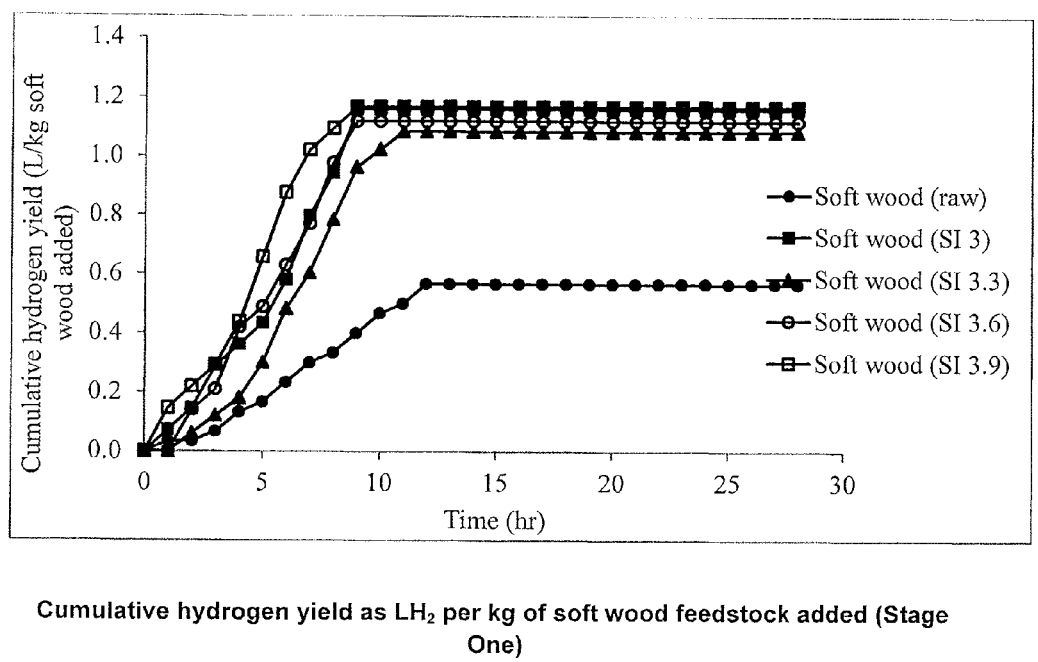
FIG. 16 illustrates cumulative hydrogen yields obtained at Stage One pretreatment conditions for Soft Wood feedstock.
Figure 17:
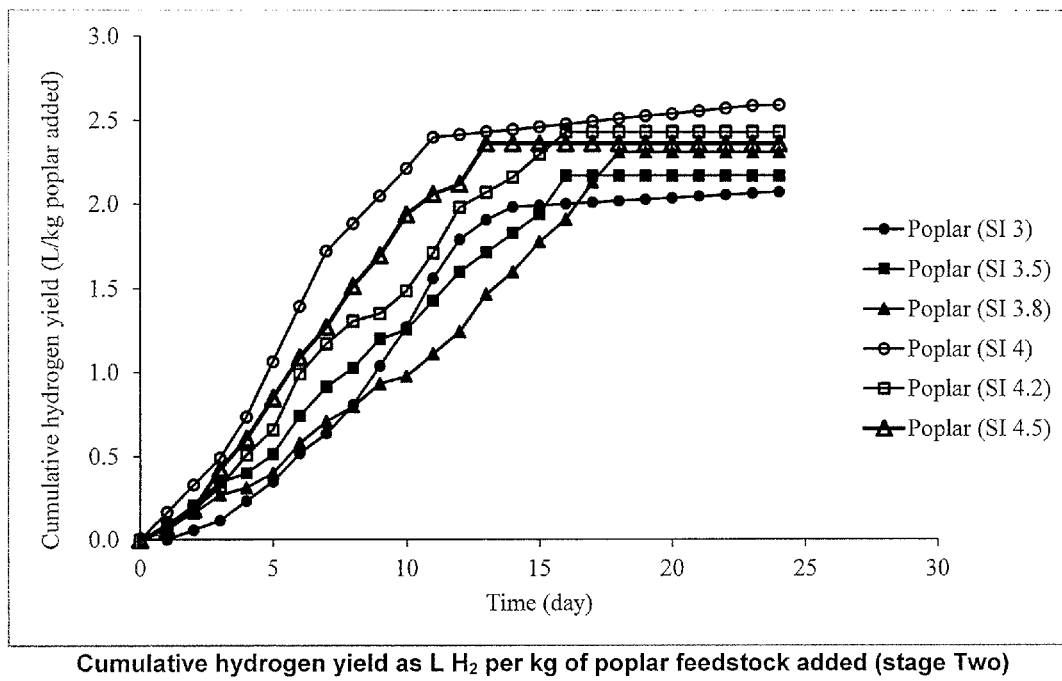
FIG. 17 illustrates cumulative hydrogen yields obtained at Stage Two pretreatment conditions for Poplar feedstock.
Figure 18:
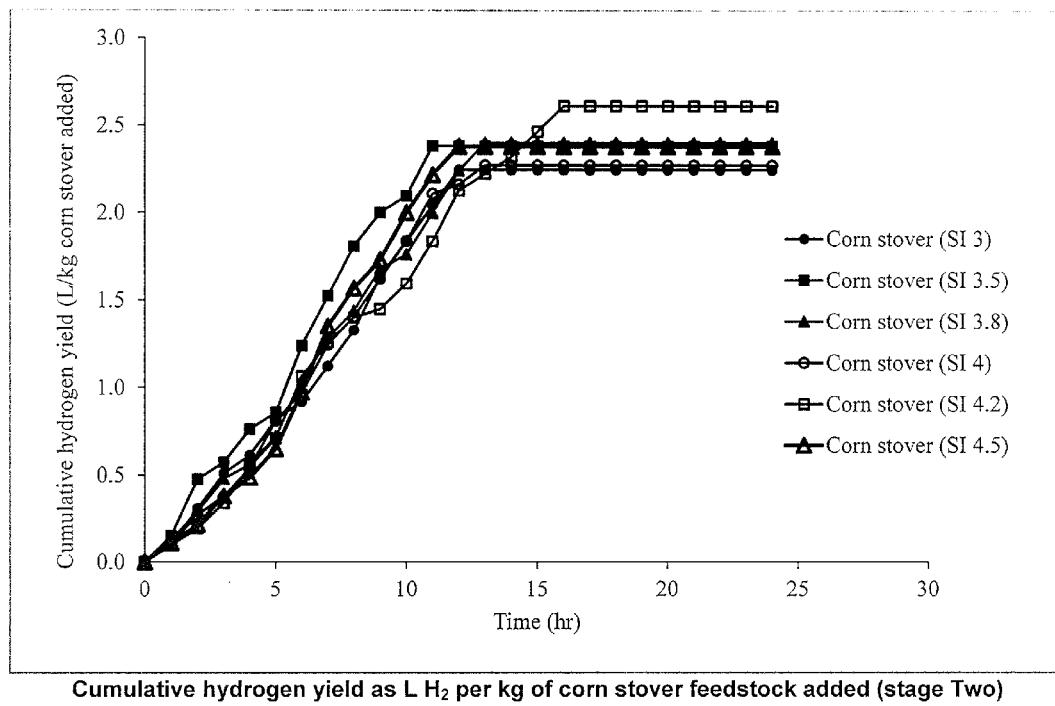
FIG. 18 illustrates cumulative hydrogen yields obtained at Stage Two pretreatment conditions for Corn Stover feedstock.

Cumulative methane yields expressed in liters methane per kg of feedstock added (LCH4/kg) obtained at the Stage One treatment conditions according to Table 4 and for different feedstocks (Poplar, Corn Stover, Soft Wood) are illustrated in FIGS. 9-11 and those obtained at Stage Two treatment conditions according to Table 4 and for Poplar and Corn Stover are illustrated in FIGS. 12 and 13. Cumulative hydrogen yields expressed in liters hydrogen per kg of feedstock added (LH2/kg) obtained at the Stage One treatment conditions according to Table 4 and for different feedstocks (Poplar, Corn Stover, Soft Wood) are illustrated in FIGS. 14-16 and those obtained at Stage Two treatment conditions according to Table 4 and for Poplar and Corn Stover are illustrated in FIGS. 17 and 18.

Biochemical Digestion

Generally, the biochemical digestion step is an anaerobic digestion step using a method and integrated system for the production of biohydrogen by dark fermentation and preferably other chemicals such as carbonate, ethanol, butanol, acetic acid, propionic acid, and butyric acid from organic material, in a completely mixed bioreactor, preferably in a continuously stirred reactor (CSTR). A downstream gravity settler may be integrated into the system after the completely mixed bioreactor.

As used herein, the term "completely mixed bioreactor" means a vessel including a mechanism for agitating the contents of the vessel (e.g. by hydraulic agitation, mechanical agitation, etc.), generally microorganisms in suspension in a growth media, (e.g. a growth media comprised of nutrients such as organic carbon compounds, nitrogen-containing compounds, phosphorous-containing compounds, and trace mineral solutions, etc.). A continuously stirred reactor (CSTR) is an example of a completely mixed bioreactor.

As used herein, the term "microorganisms" means microorganisms capable of fermenting organic material under anaerobic (not micro aerobic) conditions to produce hydrogen or methane, carbon dioxide, and a variety of organic acids and alcohols. Species of microorganisms within this term may include, for example, one or more *Clostridium* species such as *C. butyricum, C. beijerinckii, C. acetobutyricum* and *C. bifermentants, Enterobacter* species such as *Enterobacter aerogenes, Bacillus* species such as *megaterium, thuringiensis*, and other anaerobic bacteria (e.g. *Rhodobacter sphaeroides*). In general, any known anaerobic microorganisms capable of anaerobic digestion of organic material can be used in isolation or as a mixture. Specific mixtures of microorganisms designed to maximize the decomposition of selected feedstocks may also be used.

The two most common pathways for dark fermentative $H_2$ production from glucose are the acetate and butyrate pathways (Equations 1 and 2), which limit the theoretical $H_2$ yield to between 2 and 4 moles of $H_2$ per mole of glucose. Both reactions are thermodynamically favourable (i.e. negative $\Delta G$ values) and the higher the acetate to butyrate ratio, the higher the $H_2$ yield. Thus, controlling the metabolism of the culture towards acetate formation is a key factor to achieve high $H_2$ yields [Sompong O-Thong, Poonsuk Prasertsan, Nils-Kare Birkeland (2009), Evaluation of methods for preparing hydrogen-producing seed inocula under thermophilic condition by process performance and microbial community analysis. (Bioresource Technology 2009; 100: 909-918)]. Also, in order to maximize $H_2$ yield, the metabolism should be directed away from alcohols (ethanol, butanol) and reduced acids (lactate) towards volatile fatty acids (VFA) production [David B. Levin, Lawrence Pitt, Murray Love (2004), Biohydrogen production: prospects and limitations to practical application. (International Journal of Hydrogen Energy 2004; 29: 173-185)]. However, propionate production decreases the $H_2$ yield since it is a $H_2$ consuming pathway (Equation 3).

a. $C_6H_{12}O_6 + 2H_2O \rightarrow 2CH_3COOH + 2CO_2 + 4H_2$
$\Delta G_R° = -196.4$ KJ     (1)

b. $C_6H_{12}O_6 \rightarrow CH_3(CH_2)_2COOH + 2CO_2 + 2H_2$  $\Delta G_R° = -224.2$ KJ     (2)

c. $C_6H_{12}O_6 + 2H_2 \rightarrow 2CH_3CH_2COOH + 2H_2O$  $\Delta G_R° = -279.3$ KJ     (3)

Exemplary Two Stage AD Process

Figure 2:
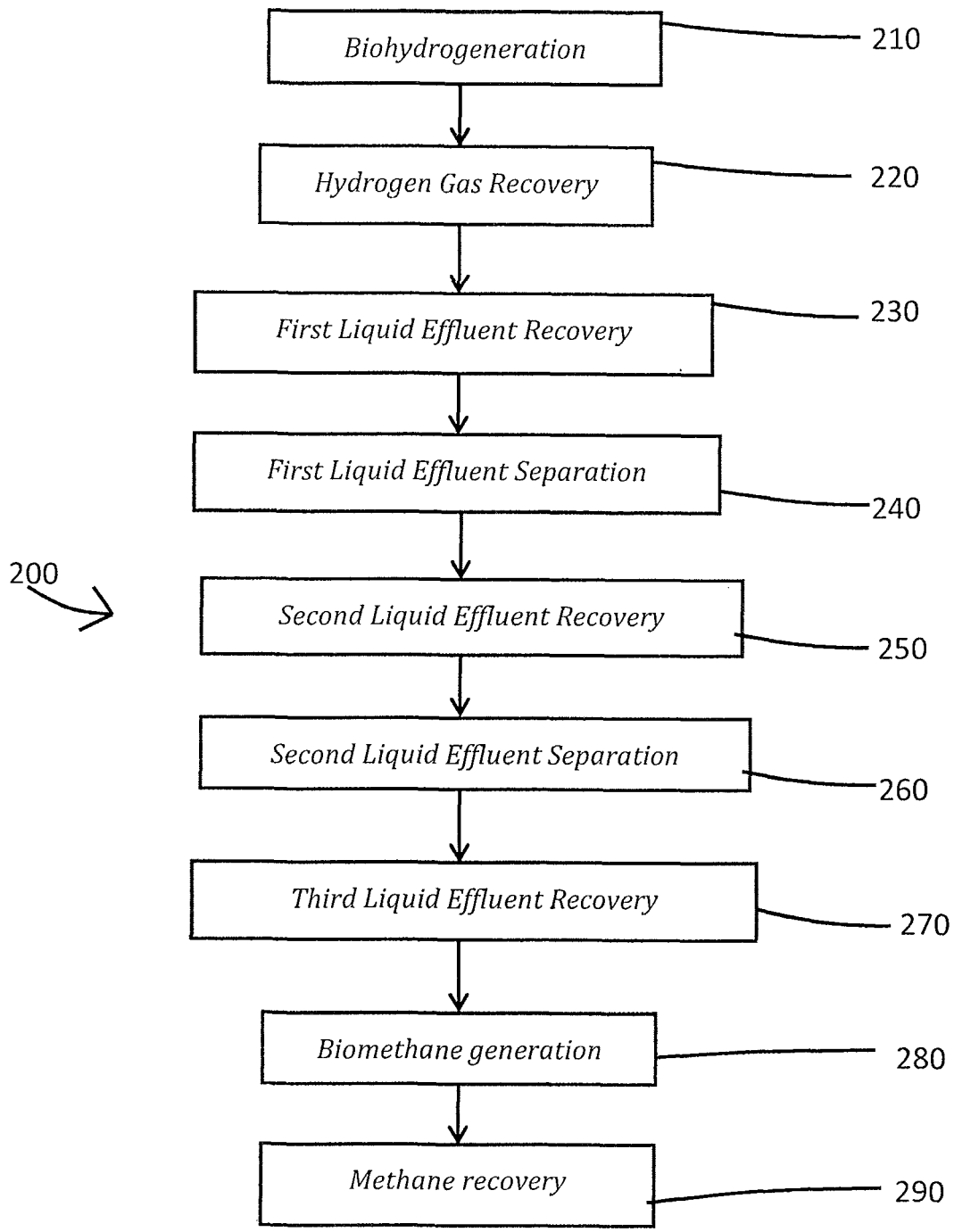
FIG. 2 schematically illustrates a two stage AD embodiment of the biochemical digestion step of the present process.

FIG. 2 is a flow diagram of a process 200 for producing hydrogen gas, carbon dioxide, volatile fatty acids, and alcohols from organic biomass. The most basic process 200 includes a biohydrogenation step 210, a $CO_2$ sequestration step 215, a hydrogen gas recovery step 220, a first liquid effluent recovery step 230, and a first liquid effluent separation step 240. In a variant of the process, which results in the production of methane and additional $CO_2$, the process further includes a second liquid effluent separation step 250, a third liquid effluent recovery step 260, a biomethane generation step 270, and a methane recovery step 280. The steps 210, 220, 230, 240, 250, 260, 270, 280 may be carried out in a continuous fashion where some or all of the steps 210, 220, 230, 240, 250, 260, 270, 280 are being performed simultaneously and continuously, in contrast with a batch approach where the steps 210, 220, 230, 240, 250, 260, 270, 280 would be carried out sequentially.

In the biohydrogenation step 210, organic material and microorganisms are provided into a completely mixed bioreactor (e.g. the completely mixed bioreactor 22 of FIG. 3) for breaking down the organic material into products including $H_2$, $CO_2$, volatile fatty acids, and alcohols. In the $CO_2$ sequestration step, $CO_2$ is captured in a headspace of the bioreactor by converting it into carbonate or bicarbonate either directly within the headspace or in a volume connected directly to the headspace into which gases from the reactor are directed for treatment and from which they are recycled back to the reactor. Both will be referred to in this specification as "headspace". In the hydrogen containing biogas recovery step 220, at least a portion of the $H_2$ containing biogas is recovered from the completely mixed bioreactor under vacuum. The hydrogen containing biogas contains mainly $H_2$, but may also contain up to 1% of trace gases such as $H_2S$ and water vapor. In the first liquid effluent recovery step 230, at least a portion of a first liquid effluent is recovered from the completely mixed bioreactor, the first liquid effluent including at least a portion of the microorganisms, the volatile fatty acids, and the alcohols.

In the $CO_2$ sequestration step, the carbonate or bicarbonate is accumulated in the headspace or in piping directly connected to the headspace and discontinuously removed from the headspace. $CO_2$ is captured by reaction with a solid hydroxide, preferably a metal hydroxide, more preferably an alkali metal hydroxide, most preferably KOH. The KOH is preferably in the form of 100% KOH pellets. Using $CO_2$ sequestration in the headspace has multiple advantages. $CO_2$ sequestration within the reactor headspace produces a substantially $CO_2$ free $H_2$ stream. By performing $CO_2$ capture directly within the reactor headspace, the amount of $CO_2$ captured can be raised to about 100% of the $CO_2$ produced in the reactor. Moreover, continuously completely removing the $CO_2$ gas from the headspace has the further side effect that the $H_2$ production is increased. This is likely due to a complete suppression of propionate formation. Thus, not only are significantly improved $H_2$ yields attained, but at the same time a virtually $CO_2$ free $H_2$ stream is available directly from the reactor, obviating any further separation of the $CO_2$ and $H_2$ gases downstream from the reactor and allowing separate removal of $H_2$ and $CO_2$ from the reactor.

In the first liquid effluent separation step 240, at least a portion of the first liquid effluent is fed into a gravity settler (e.g. the gravity settler 24 of FIG. 3) for separating at least a portion of the first liquid effluent into a first biomass including at least a portion of the microorganisms and a second liquid effluent including at least a portion of the volatile fatty acids, the alcohols and the microorganisms. Although other separators, such as membrane separators are known, they are capital intensive and much harder to operate. In the second liquid effluent separation step 250, at least a portion of the second liquid effluent is fed to a separation module (e.g. the separation module 30 of FIG. 3) for separating at least a portion of the second liquid effluent into a second biomass including at least a portion of the microorganisms and a third liquid effluent including at least a portion of the volatile fatty acids and the alcohols. At least a portion of the third liquid effluent is recovered in the third liquid effluent recovery step 260.

The first liquid effluent separation step 240 may include recirculating at least a portion of the first biomass to the completely mixed bioreactor to maintain a concentration of microorganisms in the completely mixed reactor at a preselected value.

In the biomethane generation step 270, at least a portion of the first biomass, or the second biomass, or both, is recovered and provided to a biomethane generator (e.g. the biomethane generator 40 of FIG. 3) for producing $CH_4$ and $CO_2$. At least a portion of the $CH_4$ and $CO_2$ is recovered in the methane containing biogas recovery step 280. In the methane containing biogas recovery step 220, at least a portion of the methane containing biogas which includes $CH_4$ and $CO_2$ gas is recovered from the completely mixed bioreactor under vacuum. The methane containing biogas contains mainly $CH_4$ and $CO_2$, but may also contain up to 1% of trace gases such as $H_2S$ and water vapour.

The second liquid effluent separation step 250 may include application of a variety of separation processes, for example membrane solvent separation.

The pH range may be controlled in the completely mixed bioreactor during the biohydrogenation step 210. For example, the pH range may be kept within a range of 3 to 6.8 depending on the desired end products. Preferably, the pH is maintained at about 5.5 for a maximum $H_2$ production rate, using for example $NaHCO_3$ as buffer. Other useful pH adjustment compounds may include, for example, soda ash, sodium bicarbonate, sodium hydroxide, calcium hydroxide, magnesium hydroxide, nitric acid, hydrochloric acid, etc.

The pH range may be controlled in the biomethane generator during the biomethane generation step 270. For example, the pH range may be kept within a range of 6.8 to 7.8 depending on the desired end products. Preferably, the pH is maintained at about 7.2 for a maximum methane production rate. The pH can be controlled using for example $NaHCO_3$ as buffer. Other useful pH adjustment compounds may include, for example, soda ash, sodium bicarbonate, sodium hydroxide, calcium hydroxide, magnesium hydroxide, nitric acid, hydrochloric acid, etc.

The temperature may be controlled in the completely mixed bioreactor during the biohydrogeneration step 210. For example, the temperature may be kept within a range of about 20° C. to about 45° C. for a mesophilic digestion operation and within a range of about 45 and 70° C. for a thermophilic digestion operation.

The temperature may also be controlled in the biomethane generator during the biomethane generation step 270. For example, the temperature may be kept within a range of about 20° C. to about 45° C. for a mesophilic digestion operation and within a range of about 45 and 70° C. for a thermophilic digestion operation.

The microorganisms useful for application in the system of the present application include *Clostridium* species, such as *C. butyricum, C. beijerinckii, C. acetobutyricum* and *C. bifermentants, Enterobacter* species, such as *Enterobacter aerogenes, Bacillus* species such as *B. megaterium, B. thuringiensis*, and *R. sphaeroides*. In general, any known anaerobic microorganisms capable of anaerobic digestion of organic material can be used in isolation or as a mixture. Specific mixtures of microorganisms designed to maximize the decomposition of selected feedstocks can also be used.

Exemplary AD System

Figure 3:
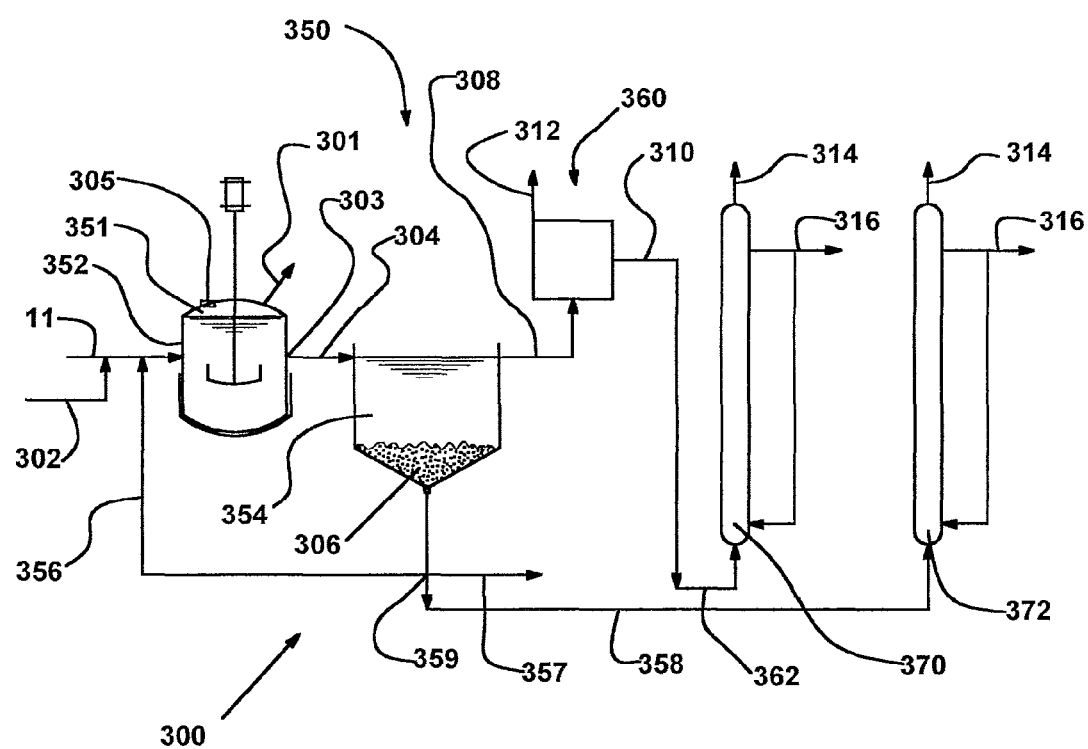
FIG. 3 schematically illustrates a system for operating the process of FIG. 2.

FIG. 3 is a schematic of an exemplary two-stage AD system 300 for producing hydrogen containing biogas, carbon dioxide, methane containing biogas, volatile fatty acids, and alcohols from organic material. Further products produced by the system 300 may include acetone, ethanol, butanol, acetic acid, propionic acid, and butyric acid. The system 300 includes a biohydrogenerator 350, a separation module 360, and a biomethane generator 370.

The biohydrogenerator 350 includes a completely mixed bioreactor 352 having an inlet for receiving organic material feedstock 11 into the completely mixed bioreactor 352. Microorganisms are added to the completely mixed bioreactor 352 to anaerobically break down the organic material feedstock 11, producing mainly $H_2$ and $CO_2$. The reactor 352 further includes a gas outlet 301 for $H_2$ gas 302 and a liquid outlet 303 for a first liquid effluent 304. The first liquid effluent 304 generally includes, for example, microorganisms, volatile fatty acids (e.g. acetic acid, butyric acid, etc.), alcohols (e.g. ethanol, butanol, etc.), acetone, etc. A $CO_2$ trap 305 is preferably included in the headspace 351 of the bioreactor 352 for $CO_2$ sequestration in the first AD stage, which trap includes a hydroxide in solid form, preferably an alkali metal hydroxide such as KOH, most preferably 100% KOH pellets. The $CO_2$ trap 305 is preferably removable from the bioreactor during operation of the biohydrogenerator. Most preferably, the bioreactor 352 includes two or more $CO_2$ traps, which can be individually and independently removed from the bioreactor and replaced one at a time (not shown) in a staggered manner to ensure continuous sequestration even during the replacement operation. The $CO_2$ trap may be a wire mesh basket for containing the KOH pellets, or any other commercially available container which can be supported in the headspace and provides sufficient access of the $CO_2$ gas in the headspace to the KOH for maximizing the $CO_2$ sequestration rate.

The biohydrogenerator 350 further includes a gravity settler 354 downstream of the completely mixed bioreactor 352 and in fluid communication with the completely mixed bioreactor 352 for receiving the first liquid effluent 304 from the completely mixed bioreactor 352. Any commercially available gravity settler equipment can be used, but gravity settlers generally used in waste water treatment systems are advantageous. In the gravity settler 354, the first liquid effluent 304 settles into a first biomass 306 and a second liquid effluent 308. The second liquid effluent 308 may include, for example, microorganisms, volatile fatty acids (e.g. acetic acid, propionic acid, butyric acid, etc.), alcohols (e.g. ethanol, butanol, etc.), acetone, etc.

A biohydrogenerator conduit 356 including appropriate conveying equipment, for example a centrifugal pump (Goulds; not shown) provides fluid communication from the bottom of the gravity settler 354 to the completely mixed bioreactor 352 for recirculation of at least part of the first biomass 306 from the gravity settler 354 to the completely mixed bioreactor 352. The gravity settler 354 further includes an output conduit 357 from the bottom of the gravity settler 354 to allow discharging and disposal of at least part of the first biomass 306. A first biomethane generator conduit 358 including appropriate conveying equipment, for example a centrifugal pump (Goulds; not shown) provides fluid communication from the bottom of the gravity settler to the biomethane generator 370 for transfer of at least part of the first biomass 306 from the gravity settler 354 to the biomethane generator 370. A valve 359, for example a rotary selection valve [Fisher] allows selection of flow through one or more of the biohydrogenerator conduit 356, the output conduit 357, and the first biomethane generator conduit 358. The concentration of microorganisms in the biohydrogenerator is controlled by setting the flow of the recirculation pump and the amount of solids discharged from the bottom of the gravity settler either to residue or to the second stage biomethane generator. The flow rates on recycle and discharge from the bottom of the gravity settler are decided based on the desired microorganisms retention time (solids retention time) in the process. An optional separation module 360 is in fluid communication with the gravity settler 354 for receiving the second liquid effluent 308. In the absence of the separation module 360, the second liquid effluent 308 and the discharged biomass from output conduit 357 are combined for further treatment or disposal. In the optional separation module 360, the second liquid effluent 308 is separated into a second biomass 310 and a third liquid effluent 312 by application of a separation process. The third liquid effluent 312 generally includes, for example, volatile fatty acids (e.g. acetic acid, propionic acid, butyric acid, etc.), alcohols (e.g. ethanol, butanol, etc.), acetone, etc. Thus, the separation module 360 is used for separate and specific removal of only the volatile fatty acids (e.g. acetic acid, propionic acid, butyric acid, etc.), alcohols (e.g. ethanol, butanol, etc.), acetone, etc. from the AD system. A second biomethane generator conduit 362 including appropriate conveying equipment, for example a centrifugal pump (Goulds; not shown) provides fluid communication from the separation module 360 to the biomethane generator 370 for circulating the second biomass 310 from the separation module 360 to the biomethane generator 370.

The biomethane generator 370 is downstream of, and in fluid communication with, the gravity settler 354, or the separation module 360, or both. The biomethane generator 370 may receive biomass from the biohydrogenerator 350, the separation module 360, or both. In the biomethane generator, the biomass is broken down into methane biogas 314 including $CH_4$ and $CO_2$, and a liquid waste 316 containing residual organics and microorganisms. An on-line gas analyzer such as Nova Analytical 920 Series biogas analyzer can be installed in order to measure the concentrations of $CH_4$ and $CO_2$, and the series 970 to $H_2$ gas concentration.

The biomethane generator 370 may include a first biomethane generator vessel 372, a second biomethane generator vessel 374, or both. The first biomethane generator vessel 372 is in fluid communication with the first biomethane generator conduit 358 for receiving the first biomass 306 from the gravity settler 354. The second biomethane generator vessel 374 is in fluid communication with the second biomethane generator conduit 362 for receiving the second biomass 310 from the separation module 360, if the latter is included in the system. If no separation module 360 is used, the second biomethane generator vessel 374 can also be omitted.

The system 300 may include a temperature controller (Rockwell PLC; not shown) for controlling the temperature in the completely mixed bioreactor 352, in the biomethane generator 370, or both. A typical temperature range in which the temperature of the contents of both the completely mixed bioreactor 352 and biomethane generator 370 is maintained between about 25° C. and about 37° C. for mesophilic operation and from 55 C. to 70 C. for thermophilic operation.

The system 300 may include a dispenser (Progressing Cavity Pump or Moineau pump; not shown) for dispensing into the completely mixed bioreactor 352 nutrients for the microorganisms which may be missing from the biomass, and/or pH adjustment compounds. The nutrients may include, for example, nitrogen containing compounds, phosphorous containing compounds, trace metals including iron, manganese, magnesium, calcium, cobalt, zinc, nickel, copper, etc. The pH adjustment compounds may include, for example, soda ash, sodium bicarbonate, sodium hydroxide, calcium hydroxide, magnesium hydroxide, nitric acid, hydrochloric acid, etc. The feedstock 11 may include organic material from multiple sources, including the pretreatment system 100 shown in FIG. 1A, or the system 300 may include a supplemental feed line 302 for feeding additional organic material other than the feedstock 11, for example waste materials, such as lignocellulosic waste materials from ethanol production, forestry waste materials, human waste, or other hydrocarbon containing waste materials suitable for bacterial digestion.

Exemplary Two Stage AD Operation

The system 300 may be applied to practice an embodiment of the process 500. In that embodiment the organic material feedstock 11 enters the completely mixed bioreactor 352 and is broken down microbiologically by hydrogen producing microorganisms, resulting in a hydrogen containing biogas including $H_2$ gas and $CO_2$ gas, and the first liquid effluent 304. The $CO_2$ gas is preferably sequestered by providing a hydroxide in a $CO_2$ trap in the headspace of the bioreactor 352 and captured as carbonate in the trap. This provides a $H_2$ stream 302 substantially free of $CO_2$, which $H_2$ stream 302 is continuously removed from the completely mixed bioreactor 352 either due to pressure generated in the completely mixed bioreactor 352 The first liquid effluent 304 flows to the gravity settler 354. The carbonate captured in the $CO_2$ trap remains in the $CO_2$ trap and is discontinuously removed from the headspace of the bioreactor 352. The $CO_2$ trap may thereby be suspended directly in the reactor headspace or in a separate volume connected to the headspace and through which gases above the liquid phase in the continuously mixed bioreactor 352 are continuously circulated. Two, selectively disconnectible separate volumes may be provided to facilitate removal of the bicarbonate without having to interrupt the biohydrogeneration process.

In the gravity settler 354, at least a portion of the microorganisms settle to the bottom of the gravity settler 354, resulting in the first biomass 306 and the second liquid effluent 308. The first biomass 306 may be recirculated at least in part to the completely mixed bioreactor 352, provided to the biomethane generator 370, sent to residue, or any combination thereof based on the concentration of microorganisms and solids in the bioreactor 352. Concentration of microorganisms and suspended solids are determined by laboratory techniques on a weekly basis. The second liquid effluent 308 flows into the separation module 360, if included.

In the optional separation module 360, at least a portion of the second liquid effluent 308 settles out into a second biomass 310, leaving as the remainder a third liquid effluent 312. The third liquid effluent 312 is emitted from the separation module 360 and recovered. The second biomass 310 may be provided to the biomethane generator 370. Providing the second biomass 310 to the completely mixed bioreactor is also possible, but not necessary in the presence of a recycle stream from the gravity settler 354.

The first biomass 306 is provided to the first biomethane generator vessel 372 through the first biomethane generator conduit 358. The second biomass 310 is provided to the second biomethane generator vessel 374 through the second biomethane generator conduit 364. In the biomethane generator 370, the first biomass 306, the second biomass 310, or both, are broken down microbiologically, resulting in production of the $CH_4$ and $CO_2$ containing methane containing biogas 314. The methane containing biogas 314 is emitted from the biomethane generator 370 due to pressure generated in the completely mixed bioreactor 352. If $CH_4$ and $CO_2$ are separately emitted from the biomethane generator 370, 372, they are combined into the methane containing biogas 314. The liquid waste 316 is discharged from the biomethane generator 370, recirculated into the biomethane generator 370, or both.

AD Examples

During testing, an increase in the acetate concentration by an average of 45%, a decrease in the butyrate concentration to an average of 51% of its original concentration, and a complete elimination of the propionate production was observed with $CO_2$ sequestration. Moreover, the hydrogen production rates under two different organic loading rates were 63 L H2/d (at 9 g/L of glucose) and 132 LH2/d (at 17 g/L of glucose) which resulted in almost 100% pure hydrogen, or substantially clean hydrogen gas.

Two integrated biohydrogen reactor clarifier systems (IBRCSs) consisting of a CSTR (7 L working volume), followed by a gravity settler (8 L volume) were operated in parallel at two different organic loading rates (OLR). For further details on the system design, refer to Hafez et al. [2009] (2) incorporated herein by reference, and FIG. 3. The gravity settler is used for decoupling Solids Retention Time (SRT) from Hydraulic Retention Time (HRT) in order to minimize and preferably suppress methane production in the CSTR. A part of the biomass separated out in the gravity settler is returned to the CSTR, while another part is transferred to a biomethane generator for methane generation separate from hydrogen generation. The biohydrogenerator was operated for 100 days at 37° C. (FIG. 3). OLR-1 and OLR-2 were 25.7 and 51.4 gCOD/L-d, respectively. A cylindrical $CO_2$ trap (0.25 L volume) with a porous bottom was introduced to the system and fixed in the reactor cover (GreenField Ethanol). Each OLR was operated in two conditions in series: 18 days without $CO_2$ sequestration (−KOH) followed by 17 days with $CO_2$ sequestration (+KOH) by adding KOH pellets (60 g) in the $CO_2$ trap fixed in the headspace. The system effluent was monitored every two days for total chemical oxygen demand (TCOD), soluble COD, volatile fatty acids (VFA), ethanol, lactate, glucose, volatile suspended solids (VSS), total suspended solids (TSS) and daily for biogas composition including hydrogen, methane and nitrogen. Samples were filtered through a 0.45 micron filter paper (Whatman, 7141-104, Japan) prior to measurement of VFAs, ethanol, lactate, and glucose.

Anaerobic digester sludge (ADS) was collected from St. Mary's wastewater treatment plant (St. Mary's, Ontario, Canada) and preheated at 70° C. for 30 min to be used as the seed. Glucose was used as the substrate with two different concentrations of 8 g/L (OLR-1) and 16 g/L (OLR-2). The feed contained sufficient inorganics at the following concentrations (mg/L): $CaCl_2$, 140; $MgCl_2.6H_2O$, 160; $MgSO_4.7H_2O$, 160; $Na_2CO_3$, 200; $KHCO_3$, 200; $K_2HPO_4$, 15; urea, 1500; $H_3PO_4$, 845; and trace mineral solution with composition as follows (mg/L): $FeCl_2.4H_2O$, 2000; $H_3BO_3$, 50; $ZnCl_2$, 50; $CuCl_2$, 30; $MnCl_2.4H_2O$, 500; $(NH_4)_6Mo_7O_{24}$, 50; $CoCl_2.6H_2O$, 50; $NiCl_2$, 50; ethylenediaminetetraacetate (EDTA), 0.5; and concentrated HCl, 1170. Buffer used in the feed was $NaHCO_3$ at concentrations of 3 and 5 g/L for systems operating at OLR-1 and OLR-2, respectively. A pH of 5.2 was maintained during the experiment using $NaHCO_3$ solution at a concentration of 168 g/L.

The volume of biogas produced was measured using a wet-tip gas meter (Rebel wet-tip gas meter company, Nashville, Tenn., USA), while the biogas composition was determined using a gas chromatograph (Model 310, SRI instruments, Torrance, Calif.) with a thermal conductivity detector (TCD) of temperature 90° C. and a molecular sieve column (Molesieve 5A, mesh 80/100, 6 ft*⅛ in) of temperature 105° C. Argon was used as the carrier gas at a flow rate of 30 mL/min. The volatile fatty acids (VFAs) concentrations were analyzed using a gas chromatograph (Varian 8500, Varian Inc., Toronto, Canada) with a flame ionization detector (FID) of temperature 250° C. equipped with a fused silica column (30 m*0.32 mm) of temperature 110° C. Helium was used as the carrier gas at a flow rate of 5 mL/min. The total and volatile suspended solids (TSS, VSS) were measured according to the standard methods [APHA 1995]. Glucose was analyzed with a Genzyme Diagnostics P.E.I. Inc. PE Canada glucose kit. HACH methods and testing kits (HACH Odyssey DR/2500) were used to measure the total and soluble chemical oxygen demands (TCOD, SCOD).

$H_2$ content reached 57.3±4% and 64.9±3% at OLR-1 and OLR-2, respectively without KOH, increasing rapidly to 100% in both cases after application of KOH in the headspace. The headspace biogas composition is dictated not only by the liquid phase $CO_2$ and $H_2$ production rates but also by the mass transfer from liquid to gas.

$H_2$ production rates increased from 57 to 70 L $H_2$/d and from 118 to 146 L $H_2$/d, in both OLR-1 and OLR-2, respectively with the use of KOH $CO_2$ sequestration. After 12 days a steady state performance was reached, with an average fluctuation in production rates of 3.4% and 8.7% in both OLR-1 and OLR-2, respectively. $H_2$ production rates based on liters of reaction liquid in the reactor (commonly referred to as reactor volume) before applying KOH were 8.2±0.5 and 16.9±1.0 L/L-d and increased to 10±0.4 and 20.9±1.1 L/L-d for both OLR-1 and OLR-2, respectively with the use of KOH $CO_2$ sequestration. Thus, removing $CO_2$ from the headspace leads to an increase in the $H_2$ production rate and results in the production of a pure $H_2$ stream virtually devoid of $CO_2$.

Figure 19:
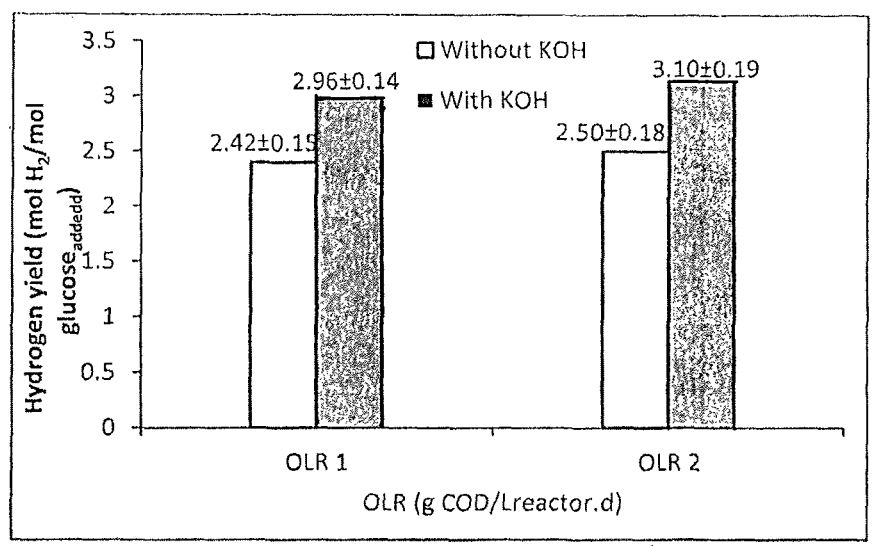
FIG. 19 illustrates hydrogen production yield in the first stage of the two stage AD with and without $CO_2$ sequestration.

The increase in the $H_2$ yield is attributed to shifting reactions 1 and 2 forward due to $CO_2$ sequestration according to the Le Chatelier principle [Sawyer et al., 2003](1). However, only an increase of 23% was observed since $H_2$ yields using the IBRCS before applying $CO_2$ sequestration are already high (2.42±0.15 and 2.50±0.18 mol/mol). With a maximum theoretical $H_2$ yield of 4 mol/mol, maximum practical yield of 3.4 mol/mol taking the biomass yield into consideration, and maximum achieved yield of 3 mol/mol [Hafez et al., 2010](3), the 23% increase in the yield due to sequestering $CO_2$ resulted in an overall yield of 91.2% of the practical yield. The impact of $CO_2$ sequestration on the $H_2$ yield would be more drastic at the low $H_2$ yields achieved by other systems using glucose as the substrate and anaerobic digested sludge as the seed, such as 1.8 mol/mol in a CSTR [Zhang et al., 2007(4); Show et al., 2007(5)], 1.57 mol/mol in an agitated granular sludge bed reactor [Wu et al., 2008](6), and 1.83 mol/mol in an AFBR [Zhang et al., 2008 (11); Show et al., 2010 (10)]. FIG. 19 illustrates hydrogen production yield with and without $CO_2$ sequestration.

It is noteworthy that there were three major changes in the effluent VFA concentrations after sequestering $CO_2$; an increase in the acetate concentration by an average of 45%, a decrease in the butyrate concentration to an average of 51% of its original concentration, and a complete elimination of the propionate concentration. High $H_2$ yields have been associated with acetate and butyrate as fermentation products [Hawkes et al., 2002 (7)]. Acetate and butyrate pathways limit the $H_2$ yield to the range of 2 to 4 moles of $H_2$ per 1 mole of glucose (Equation 1 and 2). On the other hand, low $H_2$ yields have been associated with propionate production [Hawkes et al., 2002]. The propionate pathway is a $H_2$ consuming reaction, which affects the yields negatively (Equation 3), so production of propionate should preferably be avoided [Vavilin 1995 (8)].

Reactor pH was maintained at 5.2±0.2 during the experiment using a buffer solution of 168 g/L NaHCO3. Buffer concentrations of 3 and 5 g NaHCO3/L in the feed were kept constant for both OLR-1 and OLR-2, respectively. It is noteworthy that using KOH in the headspace for $CO_2$ sequestration decreased the $NaHCO_3$ buffer consumption by the pH controller to only 16% of its consumption before adding the KOH, while overall $NaHCO_3$ buffer consumption i.e. feed and reactor pH control system decreased by 58%. Table 4 shows buffer concentrations used in the feed and consumed by the pH controller to maintain a constant pH of 5.2±0.2 during $H_2$ production.

Theoretical KOH consumption of 117 and 174 g/d for OLR-1 and OLR-2, respectively were calculated based on the experimental $CO_2$ production rates and a theoretical KOH consumption of 1.27 g KOH/g $CO_2$ (Equation 4). However, the experimental KOH consumption rates were observed to be 136 and 196 g/d for OLR-1 and OLR-2, respectively with an increase of 14% and 11% over the theoretical rates.

$$KOH+CO_2 \rightarrow KHCO_3 \quad (4)$$

Overall alkalinity consumption including both NaHCO3 and KOH was calculated to be 173 and 256 mgCaCO3/d with KOH application for both OLR-1 and OLR-2, respectively. In addition, the $KHCO_3$ produced can be recycled and used as a buffer, which will reduce the overall buffer consumption.

TABLE 16

Buffer and KOH requirements

| | | NaHCO3 added  | | | | | | Total |
| | | | | pH controller | | | | g |
| | | | Feed | | Soln. conc. | | | NaHCO3/ g glucose |
| | | pH | g/L | g/d | mL/d | g/L | g/d | g/d | feed |
|---|---|---|---|---|---|---|---|---|---|
| OLR-1 | −KOH | 5.2 ± 0.2 | 3 | 63 | 825 | 168 | 139 | 202 | 1.2 |
| | + KOH | 5.2 ± 0.2 | 3 | 63 | 140 | 168 | 24 | 87 | 0.52 |
| OLR-2 | −KOH | 5.2 ± 0.2 | 5 | 105 | 1320 | 168 | 222 | 327 | 1.0 |
| | + KOH | 5.2 ± 0.2 | 5 | 105 | 190 | 168 | 32 | 137 | 0.41 |

As is apparent from the exemplary embodiments of the process of this disclosure, removal of $CO_2$ from the headspace shifted the $H_2$ producing pathways forward, increasing $H_2$ yields by 23% to 3.1 mol/mol and $H_2$ production rates by 23.5%. Sequestering $CO_2$ affected the rates of $H_2$ production as well as the delta G of the thermodynamically unfavorable pathway that consumes propionate and produces $H_2$ and acetate. Effluent acetate concentration increased by 45% after applying KOH in the headspace, while butyrate concentration decreased to 51% of its value without sequestering $CO_2$. $CO_2$ sequestration changes the propionate consumption pathway to be thermodynamically favourable, producing more acetate and $H_2$. Although buffer consumption for pH control after $CO_2$ sequestration was reduced to 42% of its original rate before $CO_2$ removal, overall alkalinity consumption considering the trap KOH was exhausted, increased by 36% to 44%.

Dry Reforming

The dry reforming process used in the process of the present application for gas to liquid (GTL) conversion is significantly different from currently known syngas reforming processes, as higher concentrations of $CO_2$ and lower concentrations of $H_2O$ are used and the inputs into the reactor can be from up to 5 different sources and vary in composition as noted in FIGS. 6 and 7, making this reformer very flexible. The main reason the reactor is different is due to the catalyst within the reactor tubes (a $CO_2$ reforming catalyst as opposed to a steam methane catalyst, for example such as the catalyst disclosed in patent application US 20090314993 A1) and a slightly higher operating temperature, from 600 C for steam methane reformer (SRM) and from 700 to 900 C for DRM reformer. The rest of the DRM reformer is basically the same as the Linde Group Selas top fired steam methane (SMR) reformer series. In order for the process to run effectively and efficiently the molar ratios of the H, C and O atoms must line up properly such that the reactions as determined by the Gibbs free energy of the various $CO_2$, $CH_4$, $H_2$ and $H_2O$ molecules which contain these atoms must be in the ratio which creates a reaction with less than 5% $CH_4$ and 6% $CO_2$ in the syngas. The operating conditions for the reformer can be from 700 to 1,000° C. most preferably 900° C. and pressures from 1 to 20 barg, most preferably 5 barg. Tables 1, 2 and 3 show the variations in reformer outputs for 11 various input scenarios. The differences in reformer output for the 5 potential input sources of the invention where there is less than 5% $CH_4$ and 6% $CO_2$ in the output gas stream, indicates a high reformer/overall conversion efficiency where a required H2/CO output ratio is 1.67 are scenarios 5,6,7,8 and 11.

Depending on the resources available, one end of the possible operating spectrum is where a ratio of close to 1 to 1 between $CH_4$ and $CO_2$ molecules is used with practically no $H_2O$ added to the reformer as per scenario 10 in Tables 1,2 and 3 which is considered complete dry reforming. Maximum $CO_2$ is utilized in this operating scenario while low external reformer energy is used but the $H_2$/CO ratio of these molecules in the output gas is 1:1. This is not suitable to produce hydrocarbon molecules and additional $H_2$ molecules must be added into the output gas downstream in order to increase the desired ratio to make the desired hydrocarbons in the FT step of the process downstream of the reformer or dry reformer (DRM). In order to keep the hydrocarbon product green, scenario 10 requires significant $H_2$ from water electrolysis using green/non-fossil electricity sources and this most likely will not happen 100% of the time in most countries, so other operating scenarios will also occur during normal day to day operation of the invention.

Scenarios 9 and 10 are an indication of where the molar ratio of the gas exiting the reformer does not equal the $H_2$/CO molar ratio of 1.67 as all the other scenarios do. As these two conditions result in a $H_2$/CO ratio less than 1.5, there is a need to create hydrogen and inject it into the process stream downstream of the reformer. Scenario 9 shows an extreme condition where renewable electricity is available in such large amounts that besides being able to create $H_2$ for injection downstream of the reformer to increase the ratio from 1.30 to the desired level, additional $H_2$ and $O_2$ generated from electrolysis is available and is used as an internal heat source within the reformer to limit the need for external heat energy to the reformer, thereby reducing the amount of external energy required in the dry reforming case of scenario 10 to only 53% of the energy required without the availability of hydrolysis $H_2$ and $O_2$ generated from excess electricity. Scenarios 1 to 8 and scenario 11 all have a desired 1.67 $H_2$/CO ratio in the reformer gas output, which is used to create jet fuel as the main hydrocarbon product.

Scenario 7 is expected to be the average operating condition when operating on mostly cellulosic biomass and utilizing $CO_2$ sequestration in the $1^{st}$ stage of the AD system and/or supplementing H2 concentration by generating H2 from water using green electricity but production is 16% lower and the amount of $CO_2$ utilized is 25% lower than in the maximum $CO_2$ utilization scenario 10.

Scenario 11 is an example of utilizing a feedstock with no carbohydrates and no biohydrogen production where 48% less $CO_2$ can be consumed and 19% less output is achieved.

Scenario 1 is an example of what happens if no $CO_2$ is sequestered in the biohydrogen $1^{st}$ stage of the 2-stage AD system and no external $CO_2$ is consumed which results in 45% less $CO_2$ consumption and 10% less output. Similarly scenario 5 maximizes $CO_2$ utilization of scenario 1 conditions by importing $CO_2$ from an external source, which results in 4% more $CO_2$ used, but a decrease in output of 10%.

Scenarios 2,3,4,8 and 9 all have additional inputs to the reformer of $H_2$ and $O_2$ to various degrees of biogas concentrations resulting in feedstock compositional variations and reduce the external energy required for the reforming reactor by as much as 47% for 8 mole percent of $O_2$ addition in the reformer.

Scenario 6 is an example of poor feedstock, poor digestion efficiency in the AD system and results in the maximum amount of $H_2O$ used.

TABLE 17

| | | Raw & saturated Biogas mol % | | | | Input to reformer % mole | | | |
|---|---|---|---|---|---|---|---|---|---|
| | | H2 | CH4 | CO2 | H2O | H2 | CH4 | CO2 | H2O | O2 |
| Scenario | 1 | 9.5 | 51.6 | 33 | 5.9 | 7.45 | 40.45 | 25.85 | 26.25 | 0 |
| Scenario | 2 | 9.5 | 51.6 | 33 | 5.9 | 6.97 | 38.38 | 24.42 | 25.6 | 4.5 |
| Scenario | 3 | 18.85 | 47 | 28.2 | 5.95 | 16.13 | 40.33 | 24.2 | 14.63 | 4.7 |
| Scenario | 4 | 9.5 | 51.6 | 33 | 5.9 | 6.73 | 36.5 | 23.35 | 25.43 | 8 |
| Scenario | 5 | 9.5 | 51.6 | 33 | 5.9 | 6.67 | 36.15 | 26.7 | 30.47 | 0 |
| Scenario | 6 | 4.95 | 47.07 | 42.37 | 5.61 | 3.21 | 30.52 | 27.47 | 38.79 | 0 |
| Scenario | 7 | 18.85 | 47 | 28.2 | 5.95 | 16.83 | 42.03 | 35.2 | 5.95 | 0 |
| Scenario | 8 | | | | | 8 | 35 | 26 | 28 | 3 |
| Scenario | 9 | | | | | 25 | 31 | 34 | 2 | 8 |
| Scenario | 10 | 0 | 47 | 47 | 6 | | 47 | 47 | 6 | |
| Scenario | 11 | 0 | 61.56 | 32.44 | 6 | 0 | 46.24 | 24.35 | 29.41 | 0 |
| | | | | | | | | 28.96 | 21.14 average | |

TABLE 18

| | | Reformer Output | | | | | |
|---|---|---|---|---|---|---|---|
| | | % mole | | | | H2/CO ratio | Heat duty of Reformer, mmbtu/hr |
| | | H2 | CH4 | CO2 | H2O | CO | | |
| Scenario | 1 | 55 | 2 | 3 | 6 | 33 | 1.67 | 47 |
| Scenario | 2 | 53 | 1 | 4 | 9 | 32 | 1.67 | 39 |
| Scenario | 3 | 56 | 3 | 2 | 5 | 33 | 1.67 | 32 |
| Scenario | 4 | 51 | 1 | 6 | 13 | 30 | 1.67 | 30 |
| Scenario | 5 | 53 | 1 | 4 | 10 | 32 | 1.67 | 49 |
| Scenario | 6 | 52 | 1 | 5 | 11 | 31 | 1.67 | 45 |
| Scenario | 7 | 53 | 1 | 4 | 10 | 32 | 1.67 | 46 |
| Scenario | 8 | 52 | 1 | 5 | 11 | 31 | 1.66 | 46 |
| Scenario | 9 | 47 | 1 | 6 | 9 | 36 | 1.30 | 29 |
| Scenario | 10 | 45 | 3 | 3 | 4 | 46 | 1.00 | 44 |
| Scenario | 11 | 56 | 3 | 2 | 5 | 34 | 1.67 | 51 |

TABLE 19

| | | Reformer Output | | | | | External | | |
|---|---|---|---|---|---|---|---|---|---|
| | | Quantity of Syngas, NM³/hr | NM3 syngas/ mmbtu | btu/NM3 of syngas | Relative External Reformer Energy Required | Relative Reformer Output | Relative CO2 Consumption | Energy Used in Reformer comparision per CO2 % | Relative Amount of Water Used |
| Scenario | 1 | 15507 | 332 | 3016 | 97% | 90% | 55% | 177% | 438% |
| Scenario | 2 | 15217 | 392 | 2552 | 82% | 92% | 52% | 158% | 427% |
| Scenario | 3 | 13780 | 427 | 2344 | 75% | 102% | 51% | 147% | 244% |
| Scenario | 4 | 15963 | 528 | 1895 | 61% | 88% | 50% | 123% | 424% |
| Scenario | 5 | 17233 | 350 | 2858 | 92% | 81% | 57% | 162% | 508% |
| Scenario | 6 | 15621 | 346 | 2894 | 93% | 90% | 58% | 159% | 647% |
| Scenario | 7 | 16595 | 361 | 2766 | 89% | 84% | 75% | 119% | 99% |
| Scenario | 8 | 18584 | 402 | 2486 | 80% | 75% | 55% | 145% | 467% |
| Scenario | 9 | 17438 | 605 | 1654 | 53% | 80% | 72% | 74% | 33% |
| Scenario | 10 | 14014 | 322 | 3105 | 100% | 100% | 100% | 100% | 100% |
| Scenario | 11 | 17338 | 341 | 2931 | 94% | 81% | 52% | 182% | 490% |
| | | 16117.25 | 400.43 | 2591.07 average | | | | | |

The inventors have surprisingly discovered that the GTL conversion process (reformer plus FT) can be run substantially positive and the additional energy used to produce the electricity required for the entire overall process. Moreover, carbon formation and catalyst degradation via carbon deposition during the reforming process has been addressed through the proper control of the inputs and selection of appropriate basic support or promoters with minimal use of noble metals such as Pt, Rh, ruthenium (Ru), and palladium (Pd).

From a standpoint of sustainability, ethanol producers all over the world are working on expanding their line of products including utilization of non-food-grade feedstocks, i.e. cellulosic and forestry feedstocks. The inventors have now developed a novel concept for the manufacture of synthetic hydrocarbons as shown in the process layout presented in FIG. 4. In order to accomplish the goal of renewable drop-in liquid fuels as illustrated in FIG. 4, second-generation feedstocks are blended in the first step of the inventive process and pre-treated to create a good feedstock for a 2-stage AD system as presented in FIG. 1. In general, any organic material containing feedstock can be used. However, the higher the biodegradability of the organic material in the feedstock, the better the feedstock for the AD system. In the two-stage AD system, hydrogen containing biogas is produced in the first stage and methane containing biogas in the second stage. This in turn makes an abundant source of clean syngas components (hydrogen, methane and carbon dioxide) which can be used for the mixing of a syngas for conversion to liquid fuels using the Fischer Tropsch (FT) process as a foundation after reforming into a clean syngas with controlled $H_2/CO$ ratios by utilizing a flexible reforming process as presented in FIG. 7. Moreover, given the ability of the 2-stage AD system to produce pure $H_2$ gas and the abundance of waste $CO_2$ in existing corn ethanol plants, given enough biomass feedstock and green electricity, it is possible to completely consume all of the ethanol plant's $CO_2$ produced as a result of corn fermentation.

In the modified/flexible dry reforming (DRM) process of the invention the FT process is supplied with the feedstocks not from hydrocarbon sources, but exclusively from renewable sources. The carbon and oxygen for the CO component of the FT syngas can most completely be derived from $CO_2$, if a renewable electricity source is available, thereby virtually eliminating the need for added water as the oxygen source. If no electrolysis is available, 75% of the oxygen in the CO can come from $CO_2$ using 2-stage AD and operating $CO_2$ sequestration in the $1^{st}$ biohydrogen generation stage. By using a 2-stage AD process and renewable electricity to power electrolysis to create the FT feedstock gas process, the hydrocarbon products are completely renewable, rather than non-renewable sources as in conventional setups. Finally, and very importantly, by generating all feedstocks for the FT process separate from and upstream of the FT process (rather than running the water-gas shift reaction in the FT reactor), the ratio of $H_2/CO$ in the syngas can be exactly controlled. Although a variety of syngas compositions can be used, the exact control of the feedstock ratio is critical for control of the chain length in the FT reactor output products and prevention of carbon formation. For cobalt-based catalysts the optimal $H_2/CO$ ratio is around 1.5-2.1, depending on the product desired, with increase on hydrocarbon length occurring as the ratio increases. In summary, the overall process of the invention is more economical, environmentally acceptable, uses 100% green resources and does not have the inherent problems of catalyst degradation and bio instability of current biofuel processes.

FT Reforming

The Fischer-Tropsch process involves a series of chemical reactions that produce a variety of hydrocarbons, ideally having the formula ($C_nH_{(2n+2)}$)). The more useful reactions produce alkanes as follows:

$(2n+1) H_2 + n\ CO \rightarrow C_nH_{(2n+2)} + n\ H_2O$ where n is typically 10-20.

Most of the alkanes produced tend to be straight-chain, suitable as diesel, jet or gasoline fuels. In addition to alkane formation, competing reactions give small amounts of alkenes, as well as alcohols and other oxygenated hydrocarbons. In order to obtain a level of purity which allows use of the alkanes products as ASTM grade drop-in fuel products, a distillation step may be necessary downstream of the FT process.

In conventional Fischer-Tropsch plants such as Sasol II and Sasol III operating in Africa which are associated with coal or related solid sources of carbon, the solid fuel must first be converted into gaseous feedstocks, i.e., CO, $H_2$, and alkanes, which make up the synthesis gas ("Syngas"). Syngas obtained from coal gasification tends to have a $H_2/CO$ ratio of ~0.7 compared to the ideal ratio of ~1.5 to 2. A similar problem exists with wood gasification as significant amounts of water are required in the gasification process in order to achieve a suitable $H_2/CO$ molar ratio for a conventional FT process. Most coal-based Fischer-Tropsch plants rely on the feed coal to supply all the energy requirements of the syngas producing process while renewable carbon source such as wood would be used for a renewable process.

The hydrogen and carbon monoxide feedstock for the FT process can be derived from hydrocarbons by thermochemical (gasification) treatment. Several processing steps are involved in obtaining the gaseous reactants required for FT catalysis. For example the Tree to Tank "TIGAS" woody biomass gasification to gasoline process developed by GTI, Haldor Topsoe and Carbona is projected to require over 3,000 tons per day of dry wood, costing over $700 million to produce 57 million gallons of gasoline. First, gasifier reactant gases must thoroughly cleaned using expensive and complex cleaning systems to remove all contaminates to prevent poisoning of the catalysts by sulfur containing impurities, tars and chars, non-reactive gases, and cleaned of suspended particulates to prevent fouling of the catalysts. The process is therefore capital intensive and complex creating major doubt on cleaning reliability, making premature catalyst replacement highly likely and practically unavoidable. These problems are addressed with the process of the invention wherein the carbon monoxide feedstock, as well as the $H_2$ feedstock, are both produced from renewable resources and in sufficiently pure/clean form to allow use of the feedstock without processing for particulates removal or desulfurization and without degrading the catalyst. Lab tests have shown 3,000 hours of continuous operation of the catalyst without significant loss of performance. The CO is mostly generated by using dry reforming of $CO_2$ with some additional CO sourced from the Reverse Water-Gas Shift (RWGS) reaction of water as required, depending on the overall resources available.

Several reactions are normally employed to adjust the $H_2/CO$ ratio. Most important is the water gas shift reaction, which provides a source of hydrogen at the expense of the carbon monoxide feedstock:

$H_2O + CO \rightarrow H_2 + CO_2$

That of course diminishes the amount of feedstock and produces undesirable $CO_2$. For Fischer-Tropsch plants that use methane as the feedstock, another important reaction is steam/water (wet) reforming, which converts methane and water into CO and $H_2$:

$H_2O + CH_4 \rightarrow CO + 3\ H_2$

Then there is the dry ($CO_2$) reforming reaction:

$CO_2 + CH_4 \rightarrow 2\ CO + 2\ H_2$

Both of these reforming reactions are endothermic, requiring similar amounts of energy to produce the gases which can be used as a feedstock for FT syngas but maximizing the dry reforming of $CO_2$ provides recycle of the carbon back into the desired hydrocarbon product. In the case of producing renewable liquids fuels with the present process, the carbon gets to be recycled right back into the existing transportation system, reducing the overall greenhouse gas emissions at the same time.

Conventionally, the Fischer-Tropsch process is operated in the temperature range of 150-300° C. (302-572° F.). Higher temperatures lead to faster reactions and higher conversion rates but also tend to favor methane production. Rather than increasing the reaction temperature to achieve higher conversion rates, the temperature is usually maintained at the low to middle part of the range, while the operating pressure is increased to achieve higher conversion rates and the formation of long-chained alkanes. The typical pressures range from one to several tens of atmospheres. While higher pressures may be favorable, the benefits may not justify the additional costs of high-pressure equipment.

In the present process, the Reverse Water-Gas Shift Reaction (RWGS) is partially used along with dry reforming in the flexible reformer to generate a gas consisting of mostly CO and $H_2$ minimizing the unwanted gases such as $CO_2$ and $CH_4$ and elemental carbon particles all of which degrade the FT reaction that is required downstream of the flexible reformer. This is done by continually controlling the molar ratios of $CO_2$, $CH_4$, and $H_2O$ gases which are feed to the reformer by manipulating the feedstocks going to the 2-stage AD process, by adjusting the 2-stage digestion efficiency and by adjusting the amounts of external $CO_2$ injected to optimize the molar ratios for optimum flexible reformer operation. Moreover, control of the $H_2/CO$ ratio of the syngas going to the FT reaction is much facilitated by utilizing the pure $H_2$ stream from the 1$^{st}$ stage of the 2-stage AD process. Furthermore if additional $H_2$ is available from another renewable source electrolyze water, this allows for the consumption of additional $CO_2$ from external sources. This enables the constant and ongoing molar balancing of the CO and $H_2$ streams independent of any single reaction dynamics, making the control of the FT process, and in particular the chain length of the resulting hydrocarbons produced, especially reliable.

Available resources are continually measured and the process is adjusted by varying the flows of the various inputs by using an online gas analyzer multiplexed for the various inputs and outputs which measure $CO_2$, $CH_4$, CO, $H_2$ and $H_2O$ along with pressure and temperature of the reactor to continually adjust the inputs to reformer in order to maintain less than 5% $CH_4$ and less than 6% $CO_2$ in the reformer output. This is accomplished by using a predictive chemical model based on Gibbs free energy of the various potential inputs to automatically provide the basic/estimated set points for the inputs and then trim the set points by actual measurement of the flexible reformer outputs molar concentrations as depicted in FIG. 7. This can be done by combining commercially available model predictive control software such as that supplied through Pavilion Technologies of the Rockwell Automation Company and commercially available Gibbs free energy process modelling software such as Chemcad, Aspen Plus or HYSYS. Then the $H_2/CO$ ratio in the reformer output gas is finely tuned by actual measurement and addition of pure $H_2$ downstream of the flexible reformer to create the desired syngas. At all times these controls provides the best combination of the resources available at that moment in time based on carbon footprint, energy conversion, efficiency and production rate Balancing the output streams from the two stage AD process 20, and the optional water electrolysis process 90 to the proper input ratio required for the dry reforming process 30 is preferably achieved by closely monitoring and controlling the AD process 20 and the dry reforming process 30. However, due to the separation of $H_2$ biogas production from the $CH_4$ biogass production in the two stage AD process 20, excess $H_2$ from water electrolysis carried out with excess electricity can be injected together with $CO_2$ into the second stage of the AD process for balancing of the overall system.

An exemplary system setup for the syngas generation/mixing process 40 and the reforming process 30 is illustrated in FIG. 7. This Figure shows a schematic representation of the modified dry reformer or flexible reformer used in a process and system in accordance with the present description. The system includes a reforming reactor 500, a feedgas mixing chamber 410 connected to an input chamber 510 of the reforming reactor 500, a reformer output analyzer 620 connected to a reformer output chamber 520, a syngas mixer 400 downstream of the output analyzer 620, a syngas analyzer 630 downstream of the syngas mixer 400 and a process controller 600 connected to various gas stream analysis and flow control components. Hydrogen containing biogas originating from the $1^{st}$ stage of the AD process, the biohydrogenerator 350, methane containing biogas originating from the $2^{nd}$ stage of the AD process, the biomethane generator 370, external $CO_2$ originating from an external source 392, for example an ethanol plant and external water 394 are fed to the feedgas mixing chamber 410. The ratio of the respective feed streams in the input mixer 410 is controlled by the process controller 600 and in-line gas analyzers and flow control valves. The output analyzer 620 is connected to the process controller 600 through reformer output line 622 and feeds a data stream to the process controller 600 that is representative of the relative molar ratios of CO and $H_2$ exiting the reformer output chamber 520. If the $H_2$ content is too low, controller 600 adjusts the feedgas streams into the feedgas mixing chamber as will be discussed below. Optionally, the system can be provided with a supplemental $H_2$ input generated from excess electricity and/or renewable electricity in the water electrolysis unit 390. The $CO/H_2$ ratio of the reformer gas output from chamber 520 is continuously fine tuned to the desired syngas ratio for the downstream Fisher Tropsch reformer FT, by way of the hydrogen flow analyzer 610 and the inline flow control valve 611 connected to the controller 600. If the unit 390 is present, $H_2$ gas is fed to the syngas mixer 400, otherwise, part of the hydrogen containing biogas stream from the biohydrogenerator 350 is used (not shown). The composition of the final syngas entering the FT reactor is monitored by way of the syngas analyzer 630. Due to interactions between the components of the syngas, the syngas component ratio may vary and the syngas analyzer 630 provides a feedback loop for final fine adjustment of the syngas ratio by way of the controller 600 and the control valve 610.

The input mixer receives the hydrogen containing biogas, the methane containing biogas, optional external $CO_2$ and optional external water through feed lines 412, 414, 416 and 418 respectively. The feed lines include flow monitoring and flow control units such as an Ametek Thermox hydrocarbon analyzer connected to the central control module 600 (Rockwell Plant PaX). The control module 600 processes the input from the monitoring units and transits operating signals to the flow control units for adjusting the respective flow to achieve the desired feedgas ratios in the input mixer. In-line flow analyzers 602, 604, 606 and 608 such as Ametek Thermox series in feed lines 412, 414, 416 and 418 respectively provide data representative of the molar flow through the respectively monitored feed line. Analyzers 602, 604, 606 and 608 are electronically connected to the control module 600 by data lines 603, 605, 607 and 609 respectively. Feed lines 412, 414, 416 and 418 include flow control valves 640, 642, 644 and 646 (Fischer) respectively, that are connected to the control module 600 through control lines 641, 643, 645 and 647 respectively. The control module 600 uses advanced modeling based on predictive control such as Pavilion Technologies to operate the control units to adjust the molar ratio of the respective feeds in the feed lines into the input mixer 410. In one embodiment, the control module is also used for adjusting the biomass feedstocks, AD efficiency parameters, 1st stage $CO_2$ sequestration and supplemental $CO_2$ addition and downstream pure hydrogen addition based on the analyzer outputs and the model operated by the control unit.

Reactant gas flow from various sources into the reforming reactor 500 is therefore controlled based on a calculated ratio/requirement depending on the theoretical feedstocks input as compared with the molar concentration output measurements of the various analyzers as computed with a real time running process model executed in the control module 600. The inputs are then adjusted to actual measured molar concentrations obtained in all phases and the Pavilion Technologies Predictive model is adjusted to better model the actual results. The molar concentration of the reformer input and output gases is continuously measured in real time and feedgas flows through feed lines 412, 414, 416 and 418 adjusted to match process model theoretical input requirements.

Reforming reactor 500 is a flexible reformer including a furnace box 530 and multiple reaction tubes 540 of HK-40 alloy as manufactured by Kubota Metal Corporation extending through the furnace box. The reaction tubes 540 are fluidly connected to the input chamber 510 and output chamber 520 for the flow of reaction gases. The reaction tubes 540 include the DRM catalyst (U.S. Pat. No. 7,794,690 or U.S. Pat. No. 7,985,710). Reaction heat 550 is supplied to the furnace box 530 by a burner flame or molten salts which function as heat transfer media that flows around the reaction tubes 540.

Figure 8:
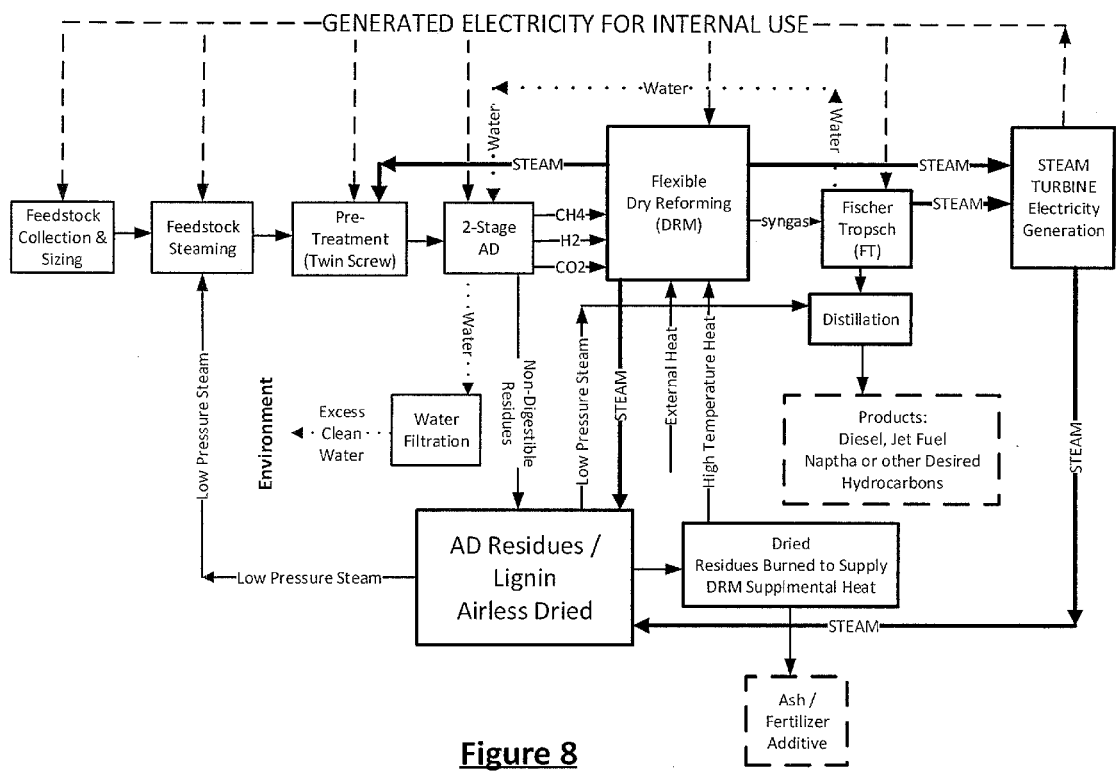
FIG. 8 is a schematic diagram of one embodiment of an integrated gas-to-liquid hydrocarbon process in accordance with the present description.

As illustrated in FIG. 8, which is a schematic representation of a gas to liquid fuel process in accordance with the present disclosure integrated with feedstock preparation, feedstock is collected and sized using standard pulp and paper equipment as manufactured by Valmet, steamed for dissolution of soluble feedstock components and removal of air, subjected to thermochemical pretreatment as discussed above, preferably in a twin screw extruder, and then fed into the 2-stage AD process discussed above in relation to FIGS. 4 and 5. Biogases generated in the AD process are feed to the reforming reactor 500 as discussed above in relation to FIG. 7 and the resulting syngas is fed to the FT reactor for synthesis of the desired hydrocarbons. The desired hydrocarbons are distilled from the product stream of the FT reactor. External heat is supplied to the reforming reactor 500 to operate the DRM reforming process. Process water generated in the reforming reactor 500 is separated as steam, which can be used in the pretreatment step of the process or fed to a steam turbine 800 for the generation of process electricity. Steam generated in the FT reactor can also be directed to the steam turbine 800.

FT Reactor Unit

In the Fischer-Tropsch process, carbon monoxide and hydrogen are passed over a catalyst for convertion into a mixture of organic molecules containing carbon and hydrogen. Various metals, including but not limited to iron, cobalt, nickel, and ruthenium, alone and in conjunction with other metals, can serve as Fischer-Tropsch catalysts. Cobalt is particularly useful as a catalyst for converting natural gas to heavy hydrocarbons suitable for the production of diesel fuel. Iron has the advantage of being readily available and relatively inexpensive but also has the disadvantage of greater water-gas shift activity. Ruthenium is highly active but quite expensive. Consequently, although ruthenium is not the economically preferred catalyst for commercial Fischer-Tropsch production, it is often used in low concentrations as a promoter with one of the other catalytic metals.

Various types of reactors have been used to carry out Fischer Tropsch reactions, including packed bed (also termed fixed bed) reactors and gas-agitated multiphase reactors, as well as tube reactors. Sie and Krishna (Applied Catalysis A: General 1999, 186, p. 55), incorporated herein by reference in its entirety, give a history of the development of various Fischer Tropsch reactors. Different types of Fischer Tropsch reactors and catalysts are disclosed in U.S. Pat. Nos. 7,012,103, 8,431,507, 8,952,076, 8,969,231, 9,180,436, US20080167391, US20090247393 and US20100099780. U.S. Pat. No. 7,012,103 discloses a fixed-bed Fischer Tropsch reactor system that achieves high overall conversion and volume productivity through the optimization of inlet temperatures, coolant temperature, length of catalyst bed, and heat transfer area and coefficient. Catalyst loading may be varied along the length of the reactor so as to further optimize reactor operation.

Many different types of Fisher Tropsch reactors (FTR) are known to the art skilled person and different FTRs can be used for conversion of the syngas 700 mixed in the output mixer 620 in accordance with the invention. The type of FTR chosen and FT process operated therein depends on the desired production volume and syngas volume available. The selection of an appropriate FTR and FT process for production of the desired synthetic hydrocarbon will be within the skill of the person skilled in the art and will not be discussed in great detail herein. In the system of the present application, the FTR used is a fixed bed reactor including a fixed catalyst bed defining a reaction zone, a reactant inlet, a product outlet, and a cooling system in thermal contact with the catalyst bed. The reactor may be a multi-tubular reactor including at least 100 tubular units containing a catalyst in a reaction zone, each tubular unit having a height between 2 and 5 meters and being in thermal contact with a cooling fluid for maintaining a desired FT reaction temperature. A feed stream consisting of the syngas 700 is supplied to the reaction zone at a linear gas superficial velocity of about 60 cm/s and converted to the desired hydrocarbons on the catalyst. The catalyst may be loaded into the reactor such that the catalyst loading or the catalyst intrinsic activity may vary along the length of the reactor.

The difference in the radially-averaged temperature between two points that are axially spaced along the reactor must be kept to a maximum, whereby the maximum temperature difference depends on the catalyst material used, If the catalyst is cobalt, the maximum temperature difference is preferably less than 15° C. and may be less than 10° C. The syngas stream 700 can be intermittently replaced with a stream comprising hydrogen for a period of time, a temperature and pressure sufficient to regenerate the catalyst. The FTR is preferably sized to achieve a desired volume of production. For fixed bed reactors, economies of scale tend to favor the use of long (tall) reactors. Because the Fischer Tropsch reaction is exothermic, however, a thermal gradient tends to form along the length of the reactor, with the temperature increasing with distance from the reactor inlet. For most Fischer Tropsch catalyst systems each ten degree rise in temperature increases the reaction rate approximately 60%, which in turn results in the generation of additional heat. To absorb the heat generated by the reaction and offset the rise in temperature, a cooling liquid is typically circulated through the reactor. Thus, for a given reactor system having a known amount of catalyst with a certain specific activity and known coolant temperature, the maximum flow rate of reactants through the reactor is limited by the need to maintain the catalyst below a predetermined maximum catalyst temperature at all points along the length of the catalyst bed and the need to avoid thermal runaway which can result in catalyst deactivation and possible damage to the physical integrity of the reactor system. Multi tubular reactors provide superior operating characteristics in this regard.

In an exemplary embodiment of the present system, a tubular fixed bed Fischer Tropsch reactor will be used which includes a fixed catalyst bed supported in a reactor housing that includes a syngas inlet and a product outlet. The reaction fluid flows through a plurality of tubular inlet and outlet units, whereby each unit contains catalyst. The exemplary reactor will include at least 100 tubular units with an internal diameter greater than 2 centimeters and a height between 2 and 5 meters. The reactor will further include a cooling system in close thermal contact with the catalyst bed. The tubular units are surrounded by a cooling fluid, which is contained by the reactor housing and is either circulate for external cooling or continuously supplied (for example water). In this setup, the FT reaction occurs inside the tubular units, while the coolant is outside the tubes, but any other suitable configuration such as are known in the art will suffice. Upon contacting the catalyst, the syngas is converted into liquid products. The liquid products exit the bottom of the reactor. The rate of reaction, and thus the rate of heat generation, at each point in the catalyst bed depends on the temperature and pressure at that point, on the gas and liquid composition at that point, on the catalyst intrinsic activity and selectivity, and on the feed rate of the reactants. The equations for calculating the heat generated by the reaction, the heat absorbed by the coolant, and the reaction rate as a function of catalyst type (e.g. iron or cobalt based Fischer-Tropsch catalysts), load, and temperature are well known in the art. It should be understood than whenever catalyst load or catalyst concentration is mentioned herein, it is also equivalent to catalyst intrinsic activity. That is, a catalyst may be diluted with inert material to lower the overall catalyst activity per reactor volume or the catalyst may be undiluted but its intrinsic activity increased or decreased, such as by varying the catalyst loading, thereby achieving a similar effect. Thus, the system can be modeled, allowing calculation of the temperature at each point along the length of the reactor and the overall conversion for the reactor. The overall productivity is the integral of the productivity along the length of the reactor, as is well known in the art.

Excess water generated in the FT reactor can be recycled to the AD process, while excess water filtered out in the AD process or removed from the AD process residues can be filtered and released to the environment.

Undigestible residue and sludge from the 2-stage AD process can be disposed, but is advantageously used for energy recovery. The residues, and optionally lignin removed in the steaming step of the feedstock pretreatment, are preferably subjected to airless drying and the dried residues subsequently combusted to generate process heat to be used in other steps of the overall process, especially the reforming step 30, as illustrated in FIGS. 4 and 5. Steam exiting the steam turbine can be used for the airless drying. The steam generated in the reformer, or at least part of it, can also be used directly in the airless drying of the AD process residues. Low pressure steam exiting the airless drying process can be recycled to the feedstock steaming step and/or the FT products distillation step. The combustion energy derived from the combustion of the dried residues is preferably used for heating the DRM reformer. Ash generated in the combustion can be used in fertilizer production.

REFERENCES:

1. Claire N. Sawyer, Perry L. McCarty, Gene F. Parkin. Chemistry for Environmental Engineering and Science (5$^{th}$ edition). McGraw-Hill Companies, Inc. 2003
2. Hisham Hafez, George Nakhla, Hesham El Naggar. Biological hydrogen production from corn-syrup waste using a novel system. Energies 2009; 2: 445-455
3. Hisham Hafez, George Nakhla, M. Hesham El. Naggar, Elsayed Elbeshbishy, Bita Baghchehsaraee. Effect of organic loading on a novel hydrogen bioreactor. International Journal of Hydrogen Energy 2010; 35: 81-92
4. Zhen-Peng Zhang, Kuan-Yeow Show, Joo-Hwa Tay, David Tee Liang, Duu-Jong Lee, Wen-Ju Jiang. Rapid formation of hydrogen-producing granules in an anaerobic continuous stirred tank reactor induced by acid incubation. Biotechnology and Bioengineering 2007; 96: 1040-1050
5. Kuan-Yeow Show, Zhen-Peng Zhang, Joo-Hwa Tay, David Tee Liang, Duu-Jong Lee, Wen-Ju Jiang. Production of hydrogen in a granular sludge-based anaerobic continuous stirred tank reactor. International Journal of Hydrogen Energy 2007; 32: 4744-4753
6. Shu-Yii Wu, Chun-Hsiung Hung, Chiu-Yue Lin, Ping-Jei Lin, Kuo-Shing Lee, Chi-Num Lin, Fang-Yuan Chang, Jo-Shu Chang. HRT-dependent hydrogen production and bacterial community structure of mixed anaerobic microflora in suspended, granular and immobilized sludge systems using glucose as the carbon substrate. International Journal of Hydrogen Energy 2008; 33: 1542-1549
7. F. R. Hawkes, R. Dinsdale, D. L. Hawkes, I. Hussy. Sustainable fermentative hydrogen production: challenges for process optimisation. International Journal of Hydrogen Energy 2002; 27: 1339-1347
8. V. A. Vavilin, S. V. Rytow, L. Ya Lokshina. Modelling hydrogen partial pressure change as a result of competition between the butyric and propionic groups of acidogenic bacteria. Bioresource Technology 1995; 54: 171-177.
9. Sie and Krishna (Applied Catalysis A: General 1999, 186, p. 55)
10. Show, K.; Zhang, K.; Tay, J.; Liang, D. T.; Lee, D.; Ren, N.; Wang, A. Critical assessment of anaerobic processes for continuous biohydrogen production from organic wastewater. Int. J. Hydrogen Energy. 2010, 35 (24), 13350-13355; DOI 10.1016/j.ijhydene.2009.11.110.
11. Zhang, Z.; Show, K.; Tay, J.; Liang, D. T.; Lee, D.; Su, A. The role of acid incubation in rapid immobilization of hydrogen-producing culture in anaerobic upflow column reactors. Int. J. Hydrogen Energy. 2008, 33 (19), 5151-5160; DOI 10.1016/j.ijhydene.2008.05.016.

What is claimed is:

1. A system for producing a synthetic hydrocarbon having a desired H/C ratio, comprising
   a two stage biodigester for biochemically digesting organic material in a first stage into a hydrogen containing biogas substantially free of methane and in a second stage into a methane containing biogas; the first bioreactor containing the organic material and anaerobic microorganisms and having an effluent drain, a separator for separating a first effluent exiting the effluent drain of the first bioreactor into separated biomass and a second effluent, a return conduit for recycling a portion of the separated biomass from the separator back into the first bioreactor, the second stage bioreactor receiving the second effluent and a remainder of the separated biomass, a controller for adjusting a fluid throughput of the first and second bioreactors for decoupling in the first bioreactor the solids retention time from the hydraulic retention time for minimizing growth of hydrogentrophic methanogens in the first bioreactor, and a carbon dioxide sequestering arrangement in the first bioreactor for continuously sequestering carbon dioxide waste gas from the headspace of the first bioreactor for producing a hydrogen containing biogas substantially free of $CO_2$ and increasing a hydrogen production rate in the first bioreactor;
   a first reformer for reacting the methane containing biogas with a catalyst to produce a carbon monoxide gas and hydrogen gas and including a splitter for dividing the methane containing biogas into first and second methane streams, a dry reforming catalyst for reacting with the first methane stream and a wet reforming catalyst for reacting with the second methane stream, the splitter including a controller for adjusting a volume ratio of the first and second methane streams for controlling the overall carbon monoxide / hydrogen ratio achieved by the first reformer;
   a mixer for combining the hydrogen containing biogas substantially free of $CO_2$, the hydrogen gas and the carbon monoxide gas into a syngas in amounts to achieve the desired H/C ratio in the syngas; and
   a second reformer for operating a Fischer-Tropsch synthesis by reacting the syngas with a catalyst to produce the synthetic hydrocarbon.

2. The system of claim 1, wherein the first reformer includes a catalyst for reforming the methane containing biogas into carbon monoxide gas and hydrogen gas; and optionally a $CO_2$ gas feed for adding $CO_2$ gas to the methane containing biogas.

3. The system of claim 1, wherein the methane containing biogas includes a methane component and a carbon dioxide component and the catalyst is a dry reforming catalyst for reacting with both components and dry reforming the methane into hydrogen gas and carbon monoxide gas.

4. The system of claim 2, wherein the catalyst is a wet reforming catalyst and the first reformer includes a water input for mixing the methane containing biogas with water for reacting with the wet reforming catalyst for wet reforming the methane into hydrogen and carbon monoxide.

5. The system of claim 1, further comprising an electro hydrolysis unit for receiving excess renewable electricity and generating $H_2$ gas and $O_2$ gas from water using the excess renewable electricity; and a $H_2$ gas drain line for feeding the $H_2$ gas into the mixer for inclusion into the syngas, and a heat generator connected to the electro hydrolysis unit for receiving a portion of the $H_2$ gas and the $O_2$ gas and to the second reformer for transfer of heat energy, the heat generator including a catalyst for reaction with the $H_2$ gas and $O_2$ gas received, to exothermically produce water and generate heat for transfer to the second reformer.

* * * * *